United States Patent
Habashita et al.

(10) Patent No.: US 8,039,674 B2
(45) Date of Patent: *Oct. 18, 2011

(54) COMPOUND HAVING S1P RECEPTOR BINDING POTENCY AND USE THEREOF

(75) Inventors: Hiromu Habashita, Mishima-gun (JP); Shinji Nakade, Tsukuba (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 884 days.

This patent is subject to a terminal disclaimer.

(21) Appl. No.: 11/630,658

(22) PCT Filed: Jun. 22, 2005

(86) PCT No.: PCT/JP2005/011872
§ 371 (c)(1), (2), (4) Date: Feb. 7, 2007

(87) PCT Pub. No.: WO2006/001463
PCT Pub. Date: Jan. 5, 2006

(65) Prior Publication Data
US 2008/0207584 A1    Aug. 28, 2008

(30) Foreign Application Priority Data
Jun. 23, 2004  (JP) .................... P. 2004-185651

(51) Int. Cl.
  *C07C 211/00*  (2006.01)
  *C09B 11/02*   (2006.01)
  *A01N 47/10*   (2006.01)
  *A61K 31/27*   (2006.01)
(52) U.S. Cl. .................... 564/428; 564/316; 514/480
(58) Field of Classification Search .................... None
See application file for complete search history.

(56) References Cited

U.S. PATENT DOCUMENTS 4,148,897 A    4/1979    Oka et al.
2007/0167425 A1*  7/2007  Nakade et al. .......... 514/210.17

FOREIGN PATENT DOCUMENTS

| EP | 0 400 495 A1 | 12/1990 |
|----|---|---|
| EP | 1 270 545 A1 | 1/2003 |
| EP | 1 283 039 A1 | 2/2003 |
| EP | 1 334 732 A1 | 8/2003 |
| WO | WO 98/38156 A1 | 9/1998 |
| WO | 01/38325 A1 | 5/2001 |
| WO | WO 02/092068 A1 | 11/2002 |
| WO | 03/062248 A2 | 7/2003 |
| WO | 03/062252 A1 | 7/2003 |
| WO | WO 03/055521 A1 | 7/2003 |
| WO | WO 2004/096752 A1 | 11/2004 |
| WO | WO 2004/096757 A1 | 11/2004 |
| WO | WO 2005/020882 A2 | 3/2005 |
| WO | WO2005020882 | * 3/2005 |

OTHER PUBLICATIONS

Morissette, S. et al. Advanced Drug Delivery Reviews 56 (2004) 275-300.*
Lens et al. British Journal of Nursing 17 (2008) 300-305 (abstract).*
Vippagunta et al. Advanced Drug Delivery Reviews 48 (2001) 3-26.*
Testa, B. Biochemical Pharmacology 68 (2004) 2097-2106.*
Stella, V. Expert Opin Ther. Patents (2004) 14(3) 277-280.*
Wolff M. Burger's Medicinal Chemistry and Drug Discovery $5^{th}$ Edition 1995, 975-977.*
Sumalainen et al. American Journal of Pathology 2005 166(3), 773-781.*
Ettmeyer, P. Journal of Medicinal Chemistry 47(10) 2004, 2393-2404.*
Divers et al. Cutis. 73(4) 2004, 257-262 (abstract).*
Sausville et al. Cancer Research 66, 2004, 3351-3354.*
Johnson et al. British Journal of Cancer 2001, 84(10) 1424-1431 (abstract).*
P. Pevarello, et al.; "Synthesis and Anticonvulsant Activity of a New Class of 2-[(Arylalkyl)amino]alkanamide Derivatives"; Journal of Medicinal and Pharmaceutical Chemistry, American Chemical Society, Easton, US; vol. 41, 1998, pp. 579-590, XP0090740418.

* cited by examiner

*Primary Examiner* — Daniel Sullivan
*Assistant Examiner* — Clinton Brooks
(74) *Attorney, Agent, or Firm* — Sughrue Mion, PLLC

(57) ABSTRACT

Provided are: a compound represented by formula (I):

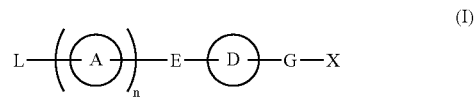

(wherein ring A and ring D each represent a cyclic group which may have a substituent(s); E and G each represent a bond or a spacer having 1 to 8 atoms in its main chain; L represents a hydrogen atom or a substituent; X represents amino which may have a substituent(s), or a heterocyclic group which contains at least one nitrogen atom and which may have a substituent(s); n represents 0 to 3, in which when n is 2 or more, a plurality of ring A's may be the same or different from one another); a salt thereof; an N-oxide form thereof; a solvate thereof, a prodrug thereof; and a medicament which includes those. The compound represented by formula (I) is capable of binding S1P receptors (in particular, EDG-1 and/or EDG-6), and useful for preventing and/or treating rejection in transplantation, autoimmune diseases, allergic diseases, etc.

6 Claims, No Drawings

COMPOUND HAVING S1P RECEPTOR BINDING POTENCY AND USE THEREOF

TECHNICAL FIELD

The present invention relates to a compound capable of binding sphingosine-1-phosphate receptor which is useful as a medicament and a medicament containing the same as an active ingredient.

In particular, the present invention relates to:
(1) a compound represented by formula (I):

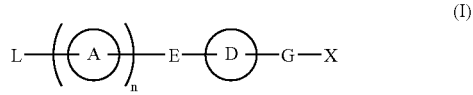

wherein, all symbols have the same meanings as described below;
a salt thereof, an N-oxide form thereof, a solvate thereof, or a prodrug thereof; and
(2) a medicament containing the compound represented by formula (I), a salt thereof, an N-oxide form thereof, a solvate thereof, or a prodrug thereof as an active ingredient.

BACKGROUND ART

Sphingosine-1-phosphate (hereinafter, abbreviated as "S1P") represented by formula (A) is a lipid that is synthesized by the intracellular metabolic turnover of sphingolipids or the extracellular action of secretory sphingosine kinase. It is pointed out that S1P acts as an intercellular and intracellular messenger (*Biochem. Pharm.*, 58, 201 (1999))

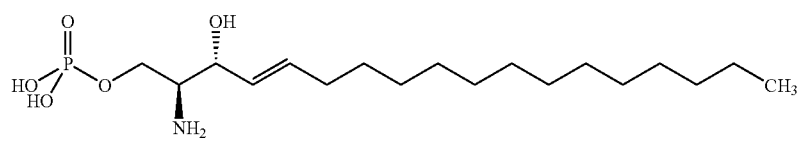

As receptors of S1P, EDG-1 which is a G-protein coupled receptor and its analogous molecules, EDG-3, EDG-5, EDG-6 and EDG-8 (also called $S1P_1$, $S1P_3$, $S1P_2$, $S1P_4$, and $S1P_5$, respectively) are known. They are called EDG family together with EDG-2, EDG-4 and EDG-7 which are receptors of lysophosphatidic acid (LPA). S1P receptors binds to S1P and deliver signals into cells via G-protein coupled with the receptors. Gs, Gi, Gq and $G_{12/13}$ etc. are known as G-proteins to which S1P receptor can couple, and it is considered that the receptor is involved in responses such as increase of cell proliferation, suppression of cell proliferation, induction of cell chemotaxis, and inhibition of cell chemotaxis.

As biological action of S1P, inhibition of migration of smooth muscle cells or cancer cells, platelet aggregation, induction of cell chemotaxis, inhibition of cell chemotaxis and the like are known in vitro experiments, and as the results of in vivo experiments, it is known that S1P shows effects of controlling blood pressure, promoting angiogenesis, reducing renal blood flow, inhibiting lung fibrosis, promoting the lymphocyte homing into lymphatic organs, and the like. It is considered that those various physiological effects are mediated by S1P receptors existing in cell membrane. However, it has been scarcely clarified excluding some cases which subtypes of S1P receptors mediate these effects in practice.

Recently, from the study for EDG-1 knock-out mice, it is strongly indicated that S1P induced angiogenesis via EDG-1 (*J Clin. Invest.*, 106, 951 (2000)). Therefore, it is suggested that an EDG-1 agonist is used as an agent for treating diseases caused by anangioplasia. For example, it is used as an agent for prevention and/or treatment of peripheral arterial disease such as arteriosclerosis obliterans, thromboangiitis obliterans, Buerger's disease, or diabetic neuropathy; varicose vein such as hemorrhoid, anal fissure, or anal fistula; dissecting aneurysm of the aorta, sepsis, inflammatory disease such as angiitis, nephritis, or pneumonia, various edematous disease involved in ischemia of various organ and increase of the blood permeability, for example, cerebral infarction, myocardial infarction, angina, congestive heart failure, pleuritis, DIC (disseminated intravascular coagulation), or multiple organ failure. In addition, angioplasty is closely related to osteogenesis, so the EDG-1 agonist can also be used as a treating agent for abnormal bone metabolism such as osteoporosis. In addition, from the study for the knock-out mice, it is also indicated that there is a possibility that EDG-1 inhibited migration of a vascular smooth muscle. Therefore, the EDG-1 agonist can also be used as an agent for prevention and/or treatment of arteriosclerosis. In addition, the EDG-1 agonist can also be used as an agent for enhancing wound healing of cornea, skin, digestive organs, or the like, or, for example, as an agent for prevention and/or treatment of bedsore, burn, ulcerative colitis, Crohn's disease, or the like. Further, the EDG-1 agonist can also be used as a preoperative, postoperative, and/or prognostic activator for blood vessel accompanying transplantation of various organs, for example, as an adhesion activator of transplanted organs such as heart transplantation, renal transplantation, dermal transplantation or liver transplantation.

In addition, the S1P is known to be effective to mouse bleomycin-elicited pulmonary fibrosis (see, WO 01/03739). Therefore, the S1P agonist can be used as an agent for prevention and/or treatment of diseases caused by fibrosis of various organs, for example, fibrosis including pulmonary fibrosis, liver fibrosis, and the like, interstitial pneumonitis, chronic pepatitis, liver cirrhosis, chronic renal insufficiency, and renal glomerular sclerosis.

In addition, it was reported that the S1P acts to promote secretion of insulin from a pancriatic β cell via EDG-3, and that the S1P inhibits glucagon-dependent insulin secretion via EDG-1 (see, for example, *Endocrine Journal*, 47(3), 261, (2000) and Diabetes, 52, 1986, (2003)). Thus, an EDG-1 agonist may be used as an agent for prevention and/or treatment of diabetes, in particular, as a glucose metabolism-improving agent, an insulin secretion-promoting agent, or a pancriatic cell-protecting agent.

On the other hand, EDG-6 is localized and strongly expressed in cells and organs of the lymphatic and hematopoietic systems including spleen, leukocytes, lymph gland, thymus, bone marrow, lung and the like, which suggests the possibility that the EDG-6 is closely related to the effects of S1P in the course of inflammation or in the immune system (*Biochem. Biophys. Res. Commun.*, 268, 583 (2000)).

Moreover, it is known that the EDG-6 polypeptide or its homologue is involved in immunomodulation, antiinflammation and the like in a similar manner as EDG-1, which brings about the potential usability of those substances in treating autoimmune diseases (e.g., systemic lupus erythematosus, rheumatoid arthritis, myasthenia gravis and the like), allergic diseases (e.g., atopic dermatitis and the like), asthma, inflammatory diseases, infection, ulcer, lymphoma, malignant tumor (e.g., cancer and the like), leukemia, arteriosclerosis, multiple organ failure, diseases associated with lymphocyte infiltration into a tissue (e.g., reperfusion injury after ischemia, and the like), and the like.

From these findings, a drug which acts on EDG-1 and/or EDG-6 is thought to be useful as an agent for prevention and/or treatment of: a peripheral arterial disease such as arteriosclerosis obliterans, thromboangiitis obliterans, Buerger's disease, or diabetic neuropathy; varicose vein such as hemorrhoid, anal fissure, or anal fistula; dissecting aneurysm of the aorta; sepsis; an inflammatory disease such as angiitis, nephritis, or pneumonia; various edematous disease involved in ischemia of various organs and increase of the blood permeability, for example, cerebral stroke, ischemia-reperfusion injury, cerebral infarction, myocardial infarction, angina, congestive heart failure, pleuritis, DIC, or multiple organ failure; bedsore; burn; trauma injury; inflammatory bowel disease; genetic disease; osteoporosis; arteriosclerosis; fibrosis including pulmonary fibrosis, liver fibrosis, and the like; interstitial pneumotitis; chronic hepatitis; liver cirrhosis; chronic renal insufficiency; renal glomerular sclerosis; diabetes; rejection in transplantation; rejection of a transplanted organ; graft versus host disease; an autoimmune disease (e.g., systemic lupus erythematosus, rheumatoid arthritis, multiple sclerosis, psoriasis, ulcerative colitis, Crohn's disease, myasthenia gravis, autoimmune diabetes, and the like); an allergic disease (e.g., atopic dermatitis, pollen disease, food allergy, and the like); asthma; infectious disease; ulcer; lymphoma; malignant tumor (e.g., cancer and the like); leukemia; a disease associated with lymphocyte infiltration into a tissue; and the like. In addition, those drugs are thought to be useful as a preoperative, postoperative, and/or prognostic activator for blood vessel accompanying transplantation of various organs, tissues, and/or cells, for example, as an adhesion activator of transplanted organs such as heart transplantation, renal transplantation, dermal transplantation or liver transplantation.

Recently, it was reported that an EDG-1 agonist which selectively binds to EDG-1 as compared with EDG-3 at least 20 folds was effective for immune disorder (see, WO 03/061567).

On the other hand, it is disclosed that a carboxylic acid derivative represented by formula (Z):

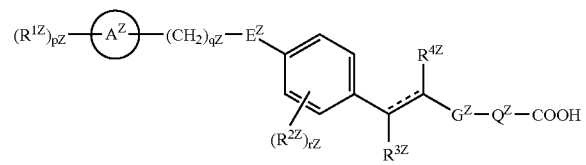

(Z)

wherein $R^{1Z}$ represents C1-8 alkyl, C1-8 alkoxy, a halogen atom, nitro, or trifluoromethyl; ring $A^Z$ represents a C5-7 monocyclic carbocyclic group or a 5- to 7-membered monocyclic heterocyclic group containing one or two nitrogen atoms, one oxygen atom and/or one sulfur atom; $E^Z$ represents $-CH_2-$, $-O-$, $-S-$ or $-NR^{6Z}-$, in which $R^{6Z}$ represents a hydrogen atom or C1-8 alkyl; $R^{2Z}$ represents C1-8 alkyl, C1-8 alkoxy, a halogen atom, nitro or trifluoromethyl; $R^{3Z}$ represents a hydrogen atom or C1-8 alkyl; $R^{4Z}$ represents a hydrogen atom or C1-8 alkyl, or $R^{2Z}$ and $R^{4Z}$ may be taken together to form $-CH_2CH_2-$ or $-CH=CH-$; $G^Z$ represents $-CONR^{7Z}-$, $-NR^{7Z}CO-$, $-SO_2NR^{7Z}-$, $-NR^{7Z}SO_2-$, $-CH_2NR^{7Z}-$ or $-NR^{7Z}CH_2-$, in which $R^{7Z}$ represents a hydrogen atom, C1-8 alkyl or the like; $Q^Z$ represents C1-4 alkylene or the like; $p^Z$ represents 0 or an integer of 1 to 5; $q^Z$ represents an integer of 4 to 6; $r^Z$ represents 0 or an integer of 1 to 4; and ⋯ represents a single bond or a double bond, a prodrug thereof, or a non-toxic salt thereof is useful as an EDG-1 agonist (see WO 02/092068).

Moreover, it is disclosed that a compound represented by formula (Y):

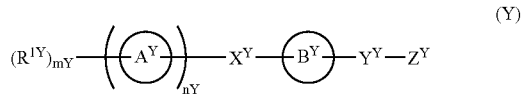

(Y)

wherein ring $A^Y$ represents a cyclic group; ring $B^Y$ represents a cyclic group which may further have a substituent(s); $X^Y$ represents a bond or a spacer having 1 to 8 atoms in its main chain in which one atom in the spacer may be taken together with a substituent on ring $B^Y$ to form a ring group which may have a substituent(s); $Y^Y$ represents a bond or a spacer having 1 to 10 atoms in its main chain in which one atom in the spacer may be taken together with a substituent on ring $B^Y$ to form a ring group which may have a substituent(s); $Z^Y$ represents an acidic group which may be protected; nY represents 0 or 1, wherein when nY is 0, mY represents 1 and $R^{1Y}$ represents a hydrogen atom or a substituent, and when nY is 1, mY is 0 or an integer of 1 to 7 and $R^{1Y}$ represents a substituent in which when mY is 2 or more, a plurality of $R^{1Y}$s are the same or different from each other, a salt thereof, a solvate thereof, or a prodrug thereof has an S1P receptor binding ability (see WO 2005/020882).

Moreover, it is disclosed that a compound represented by formula (S):

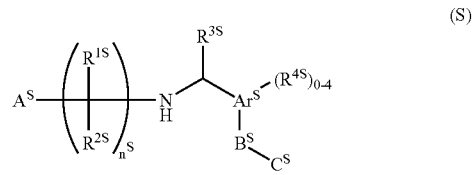

(S)

wherein $Ar^S$ represents phenyl or naphthyl; $A^S$ represents carboxy, or the like; $n^s$ represents 2, 3 or 4; $R^{1S}$ and $R^{2S}$ each independently represents a hydrogen atom, a halogen atom, hydroxy, carboxy, C1-6 alkyl which may be substituted by 1 to 3 halogen atoms, or phenyl which may be substituted by 1 to 3 halogen atoms; $R^{3S}$ represents a hydrogen atom or C1-4 alkyl which may be substituted by 1 to 3 hydroxy or halogen atoms; $R^{4S}$s each independently represents hydroxy, a halogen atom, carboxy, or the like; $C^S$ represents C1-8 alkyl, C1-8 alkoxy, phenyl, or the like or $C^S$ is nil; and $B^S$ represents phenyl, C5-16 alkyl, or the like (only necessary parts of the definitions of the symbols are extracted);

a pharmaceutically acceptable salt thereof and a hydrate thereof, and a compound represented by formula (T):

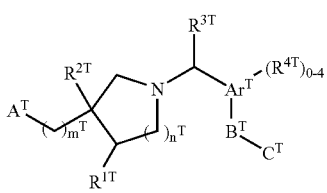
(T)

wherein $Ar^T$ represents phenyl or naphthyl; $A^T$ represents carboxy, or the like; $m^T$ represents 0 or 1; $n^T$ represents 0 or 1; $R^{1T}$ and $R^{2T}$ each independently represents a hydrogen atom, a halogen atom, hydroxy, carboxy, C1-4 alkyl or phenyl which may be substituted by a halogen atom, or the like; $R^{3T}$ represents a hydrogen atom, C1-4 alkyl which may be substituted by hydroxy or a halogen atom, or the like; $R^{4T}$s each independently represents a halogen atom, C1-4 alkyl, C1-3 alkoxy, or the like; $C^T$ represents C1-8 alkyl, C1-8 alkoxy, phenyl, or the like or $C^T$ is nil; and $B^T$ represents phenyl, C5-16 alkyl, or the like (only necessary parts of the definitions of the symbols are extracted);

a pharmaceutically acceptable salt thereof, and a hydrate thereof are useful as EDG-1 agonists (see WO 03/062248 and WO 03/062252).

Moreover, it is known that a compound represented by formula (B):

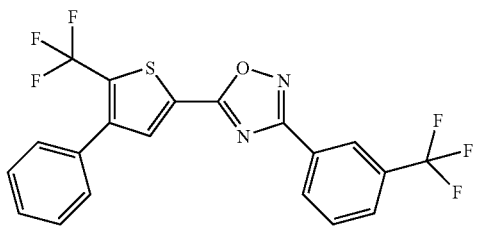
(B)

is an EDG-1-selective agonist (see, *J. Biol. Chem.*, 279, 13839 (2004)).

In addition, various compounds each having an agonistic activity against EDG-1 are disclosed (see, WO 03/062392 and WO 04/009816).

In addition, it is disclosed that a compound having a dihydronaphthalene skeleton and represented by formula (U):

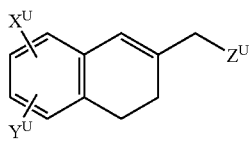
(U)

wherein $X^U$ and $Y^U$ each independently represents a hydrogen atom, a fluorine atom, a chlorine atom, a bromine atom, alkyl having 4 or less carbon atoms, or alkoxyl having 4 or less carbon atoms, and $Z^U$ represents a secondary or tertiary amine (only necessary parts of the definitions of the symbols are extracted), is useful as an analgesic or a tranquilizer (see, U.S. Pat. No. 4,022,791).

Similarly, there is disclosed a bacteriocide composition containing an organic amine compound represented by formula (W):

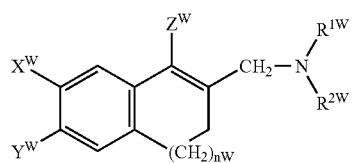
(W)

wherein one of $X^W$ and $Y^W$ represents a hydrogen atom while the other represents the following:

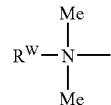

provided that $R^W$ represents a hydrogen atom, methyl, or ethyl; $Z^W$ represents a hydrogen atom, C1-4 alkyl, or the like; $R^{1W}$ and $R^{2W}$ each represent a hydrogen atom or C1-4 alkyl, or $R^{1W}$ and $R^{2W}$ each represent an optionally-substituted heterocyclic group together with a nitrogen atom adjacent thereto; and nW represents 0 or 1 (only necessary parts of the definitions of the symbols are extracted);

a stereoisomer of the compound; or an acid addition salt thereof (see JP-A-61-291576).

In addition, it is disclosed that an N-cycloalkyl-[ω-(3,4-dihydro-2-naphthalenyl)alkyl]amine derivative represented by formula (VV):

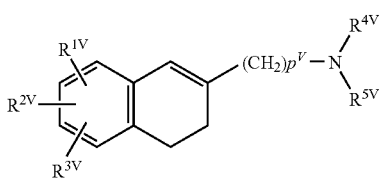
(VV)

wherein $R^{1V}$ and $R^{2V}$ each represent a hydrogen atom, a halogen atom, alkyl, or the like, or $R^{1V}$ and $R^{2V}$ together form ethylenoxy, trimethylene, or the like; $R^{3V}$ represents a hydrogen atom, a halogen atom, alkyl, or the like; $R^{4V}$ represents a hydrogen atom, alkyl, acyl, or the like; $R^{5V}$ represents cycloalkyl; and $p^V$ represents an integer of 2 to 6 (only necessary parts of the definitions of the symbols are extracted)

is useful as a treating agent for pollakiuria and acraturesis (see JP-A-10-120632).

In addition, it is disclosed that an amine compound represented by formula (X):

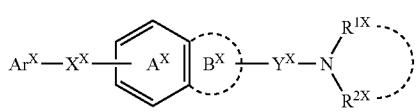
(X)

wherein $Ar^X$ represents an aromatic ring assembly group or a fused aromatic ring; $X^X$ represents (i) a bond, (ii) —S—, (iii) C1-6 alkylene or the like which may have 1 to 3 substituents selected from the group consisting of oxo and C1-6 alkyl, (iv) —CO—O—, or (v) —(CH$_2$)$_{pX}$—X$^{LX}$, or the like; $Y^X$ represents a divalent C1-6 aliphatic hydrocarbon group; $R^{1X}$ and $R^{2X}$ each represent a hydrogen atom or lower alkyl, or $R^{1X}$ and R$^{2X}$ together form a nitrogen-containing heterocyclic group; ring A$^X$ represents a benzene ring; and ring B$^X$ represents a 4- to 8-membered ring (only necessary parts of the definitions of the symbols are extracted)
is useful as an inhibitor of production or secretion of amyloid β protein (see WO 98/038156).

DISCLOSURE OF THE INVENTION

Immunosuppressants are useful for preventing and treating inflammatory diseases, allergic diseases, and rejection in transplantation. However, it is known that many of immunosuppressants used at present have severe side effects with a considerably high frequency. Therefore, it has been urgently required to develop a drug which has few side effects and thus is safe, and shows high immunosuppression effects.

The inventors of the present invention have made extensive studies on a sphingosine-1-phosphate (S1P) receptor-regulating agent which is useful as a medicament. As a result, the inventors of the present invention have found that a compound of the present invention represented by formula (I) surprisingly had a strong binding ability to an S1P receptor, especially, EDG-1 and/or EDG-6. Further, it was found that, in in vivo experiments, the compound of the present invention promoted homing of lymphocytes in peripheral blood into a secondary lymphatic tissue and had an immunosuppressive action. In addition, it was found that the compound of the present invention surprisingly had few side effects and thus is safe in an animal model. The inventors of the present invention thus have completed the present invention.

That is, the present invention relates to:
1. a compound represented by formula (I):

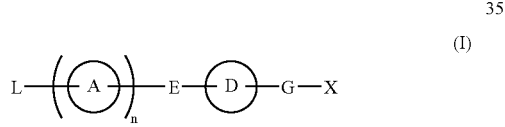

in which ring A and ring D each independently represents a cyclic group which may have a substituent(s);
E and G each independently represents a bond or a spacer having 1 to 8 atoms in its main chain;
L represents a hydrogen atom or a substituent;
X represents amino which may have a substituent(s) or a heterocyclic group which contains at least one nitrogen atom and which may have a substituent(s);
n represents 0 or an integer of 1 to 3, wherein when n is 2 or more, a plurality of ring A's may be the same or different, from one another,
a salt thereof, an N-oxide form thereof, a solvate thereof, or a prodrug thereof;
2. the compound according to above item 1, wherein ring A is a C3-10 monocyclic or bicyclic carbocyclic group which may have a substituent(s), or a 3- to 10-membered monocyclic or bicyclic heterocyclic group which contains 1 to 5 nitrogen atoms, one or two oxygen atoms, and/or one sulfur atom and which may have a substituent(s);
3. the compound according to above item 2, wherein ring A is benzene, oxadiazole, or cyclohexane ring which may have a substituent(s);
4. the compound according to above item 1, wherein ring D is a C3-15 monocyclic, bicyclic, or tricyclic carbocyclic group which may have a substituent(s), or a 3- to 15-membered monocyclic, bicyclic, or tricyclic heterocyclic group which contains 1 to 5 nitrogen atoms, one or two oxygen atoms, and/or one sulfur atom and which may have a substituent(s);
5. the compound according to above item 4, wherein ring D represents any one of the followings:

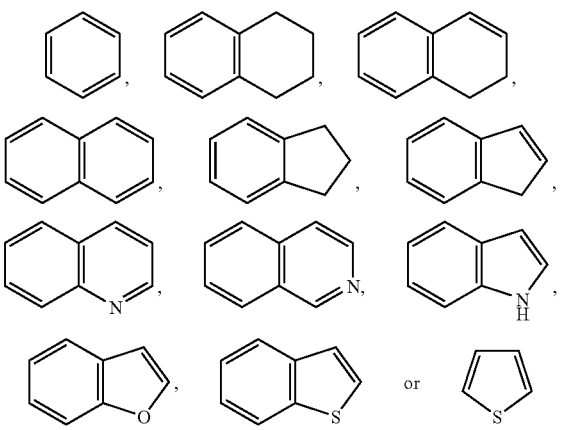

which may have a substituent(s);
6. the compound according to above item 5, wherein ring D is benzene, dihydronaphthalene, or naphthalene ring which may have a substituent(s);
7. the compound according to above item 6, wherein ring D represents the following:

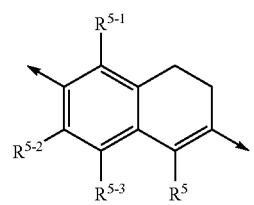

wherein R$^5$, R$^{5-1}$, R$^{5-2}$, and R$^{5-3}$ each independently represents a hydrogen atom, a halogen atom, trifluoromethyl, trifluoromethoxy, or C1-8 alkyl, and a right-direction arrow binds to G;
8. the compound according to above item 1, wherein E is a spacer having 1 to 8 atoms in its main chain which is 1 to 8 combinations selected from the group consisting of (1) C1-8 alkylene which may be substituted, (2) C2-8 alkenylene which may be substituted, (3) oxygen atom, (4) sulfur atom which may be oxidized, and (5) nitrogen atom which may be substituted;
9. the compound according to above item 8, wherein E is "—(C1-7 alkylene which may be substituted)-(oxygen atom)-" in which the oxygen atom binds to ring D;
10. the compound according to above item 9, wherein E is "—(C1-3 alkylene which may be substituted)-(oxygen atom)-" in which the oxygen atom binds to ring D and wherein n is 1;
11. the compound according to above item 10, wherein the "—(C1-3 alkylene which may be substituted)-(oxygen atom)-" represented by E is any one of the followings:

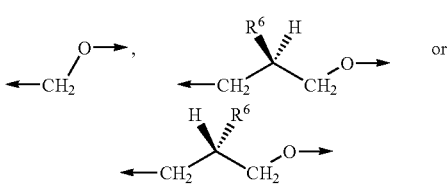

wherein R⁶ represents a hydrogen atom, a halogen atom, hydroxy which may be protected, amino which may be protected, C1-8 alkyl, or C1-8 alkyl substituted by hydroxy which may be protected, ......⁽⁽⁽represents connection in an α-configuration, ╱represents connection in a β-configuration, and a right-direction arrow binds to ring D;

12. the compound according to above item 11, wherein R⁶ represents methyl;
13. the compound according to above item 1, wherein G is a spacer having 1 to 4 atoms in its main chain;
14. the compound according to above item 13, wherein G is C1-3 alkylene which may be substituted, C2-3 alkenylene which may be substituted, or C2-3 alkynylene which may be substituted;
15. the compound according to above item 1, wherein X represents the following:

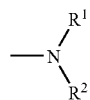

wherein R¹ and R² each independently represents a hydrogen atom or a substituent;
16. the compound according to above item 15, wherein R¹ represents the following:

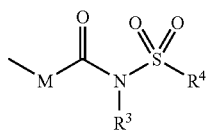

wherein M represents a bond or C1-4 alkylene which may be substituted, R³ represents a hydrogen atom or a substituent, and R⁴ represents a substituent;
17. the compound according to above item 1, wherein X represents a heterocyclic group which contains at least one nitrogen atom and which may have a substituent(s);
18. the compound according to above item 17, wherein X represents a 4- to 8-membered monocyclic heterocyclic group which contains at least one nitrogen atom and which may have a substituent(s);
19. the compound according to above item 17, wherein a substituent for X represents the following:

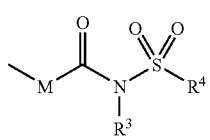

wherein all symbols have the same meanings as described in above item 16;
20. the compound according to above item 1, which is a compound represented by formula (I-3-10):

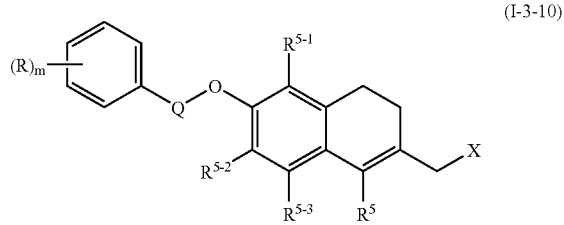

(I-3-10)

wherein R represents a substituent; m represents 0 or an integer of 1 to 5, wherein when m is 2 or more, a plurality of R's may be the same or different; Q represents C1-3 alkylene which may be substituted; and other symbols have the same meanings as described in any one of above items 1 and 7;
21. the compound according to above item 20, wherein R represents a halogen atom, C1-8 alkyl which may have a substituent(s), or C1-8 alkoxy which may have a substituent(s);
22. the compound according to above item 20, wherein R⁵ represents a halogen atom, trifluoromethyl, trifluoromethoxy, or C1-8 alkyl;
23. the compound according to above item 1, which is
N-({6-[3-(4-fluorophenyl)propoxy]-1-methyl-3,4-dihydro-2-naphthalenyl}methyl)ethanamine,
N-(3-{[(6-{[(2S)-3-(4-chlorophenyl)-2-methylpropyl]oxy}-1-methyl-3,4-dihydro-2-naphthalenyl)methyl]amino}propanoyl)methanesulfonamide,
N-(3-{[(6-{[(2S)-3-(4-chlorophenyl)-2-methylpropyl]oxy}-1-methyl-3,4-dihydro-2-naphthalenyl)methyl]amino}propanoyl)-3,5-dimethyl-4-isoxazolesulfonamide,
N-[(6-{[(2S)-3-(4-fluorophenyl)-2-methylpropyl]oxy}-1-methyl-3,4-dihydro-2-naphthalenyl)methyl]ethanamine,
N-({6-[3-(4-fluorophenyl)-2-methylpropoxy]-1-methyl-3,4-dihydro-2-naphthalenyl}methyl)ethanamine,
N-({1-[(1-chloro-6-{[(2S)-3-(4-chlorophenyl)-2-methylpropyl]oxy}-3,4-dihydro-2-naphthalenyl)methyl]-3-azetidinyl}carbonyl)methanesulfonamide,
N-({1-[(1-chloro-6-{[(2S)-3-(4-chlorophenyl)-2-methylpropyl]oxy}-3,4-dihydro-2-naphthalenyl)methyl]-3-azetidinyl}carbonyl)-2,6-difluorobenzensulfonamide,
N-({1-[(1-chloro-6-{[(2S)-3-(4-chlorophenyl)-2-methylpropyl]oxy}-3,4-dihydro-2-naphthalenyl)methyl]-3-azetidinyl}carbonyl)-3,5-dimethyl-4-isoxazolesulfonamide,
1-{6-[(4-isobutyl-2-methoxybenzyl)oxy]-1-methyl-3,4-dihydro-2-naphthalenyl}-N,N-dimethylmethanamine,
[1-({6-[(4-isobutyl-2-methoxybenzyl)oxy]-1-methyl-3,4-dihydro-2-naphthalenyl}methyl)-3-azetidinyl]methanol,
1-({6-[(4-isobutyl-2-methoxybenzyl)oxy]-1-methyl-3,4-dihydro-2-naphthalenyl}methyl)-4-(2-pyridinyl)piperazine,
2-[4-({6-[(4-isobutyl-2-methoxybenzyl)oxy]-1-methyl-3,4-dihydro-2-naphthalenyl}methyl)-1-piperazinyl]pyrimidine, or
2-[4-({6-[(4-isobutyl-2-methoxybenzyl)oxy]-1-methyl-3,4-dihydro-2-naphthalenyl}methyl)-1-piperazinyl]pyrazine;
24. a pharmaceutical composition which comprises the compound represented by formula (I) according to above item 1, a salt thereof, an N-oxide form thereof, a solvate thereof, or a prodrug thereof;

25. the pharmaceutical composition according to above item 24, which is an S1P receptor binding agent, an immunosuppressant agent, and/or an agent causing lymphopenia;
26. the pharmaceutical composition according to above item 25, wherein the S1P receptor binding agent is an EDG-1 agonist and/or an EDG-6 agonist;
27. the pharmaceutical composition according to above item 24, which is an agent for preventing and/or treating an EDG-1 and/or EDG-6-mediated disease;
28. the pharmaceutical composition according to above item 27, wherein the EDG-1 and/or EDG-6-mediated disease is rejection in transplantation of an organ, tissues, and/or cells, autoimmune disease, allergic disease, asthma, multiple organ failure, ischemia-reperfusion injury, malignant tumor, lung fibrosis, and/or liver fibrosis;
29. the pharmaceutical composition according to above item 28, wherein the rejection in transplantation of an organ, tissues, and/or cells is a rejection in transplantation of kidney, liver, heart, lung, dermal graft, cornea, vascular, chordae, bone, bone marrow cells, neuronal cells, and/or pancreatic islet cells, the autoimmune disease is systemic lupus erythematosus, rheumatoid arthritis, multiple sclerosis, psoriasis, inflammatory bowel disease, autoimmune diabetes, and/or collagen disease, and the allergic disease is atopic dermatitis, pollen disease, and/or food allergy;
30. a medicament comprising the compound represented by formula (I) according to above item 1, a salt thereof, an N-oxide form thereof, a solvate thereof, or a prodrug thereof in combination with one or two or more selected from the group consisting of an antimetabolite, an alkylating agent, a T cell activation inhibitor, a calcineurin inhibitor, a proliferation signal inhibitor, a steroid, an immunosuppressant agent, an antibody used in immune suppression, an agent for treating rejection, an antibiotic, an antiviral agent, and an antifungal agent;
31. a method for prevention and/or treatment of an EDG-1 and/or EDG-6-mediated disease, immunosuppression, and/or lymphopenia in a mammal, which comprises administering to the mammal an effective amount of the compound represented by formula (I) according to above item 1, a salt thereof, an N-oxide form thereof, a solvate thereof, or a prodrug thereof;
32. use of the compound represented by formula (I) according to above item 1, a salt thereof, an N-oxide form thereof, a solvate thereof, or a prodrug thereof for the manufacture of a treating agent for prevention and/or treatment of an EDG-1 and/or EDG-6-mediated disease, immunosuppression, and/or lymphopenia; and
33. a method for producing the compound represented by formula (I) according to above item 1, a salt thereof, an N-oxide form thereof, a solvate thereof, or a prodrug thereof.

In the present specification, S1P means sphingosine-1-phosphate ((2S,3R,4E)-2-amino-3-hydroxyoctadec-4-enyl-1-phosphate). EDG means endothelial differentiation gene which is a generic term including from EDG-1 to EDG-8. Among the EDGs, EDG-1, EDG-3, EDG-5, EDG-6 and EDG-8 (named $S1P_1$, $S1P_3$, $S1P_2$, $S1P_4$ and $S1P_5$, respectively) are regarded as S1P receptors.

In the present specification, the receptor binding drug or binding agent includes an agonist, an antagonist, and an inverse agonist. The agonist includes a full agonist and a partial agonist.

In the present invention, a preferable S1P receptor binding drug or binding agent is an EDG-1 agonist which may have an agonistic activity against EDG-6 and/or an EDG-6 agonist which may have an agonistic activity against EDG-1.

In the present specification, an EDG-1-mediated disease means a disease in which EDG-1 is thought to be involved in onset, deterioration, healing, or the like of the disease. Examples of the disease include: a peripheral arterial disease such as arteriosclerosis obliterans, thromboangiitis obliterans, Buerger's disease, or diabetic neuropathy; varicose vein such as hemorrhoid, anal fissure, or anal fistula; dissecting aneurysm of the aorta; sepsis; an inflammatory disease such as angiitis, nephritis, or pneumonia; various edematous disease involved in ischemia of various organs and increase of the blood permeability, for example, cerebral stroke, ischemia-reperfusion injury, cerebral infarction, myocardial infarction, angina, congestive heart failure, pleuritis, DIC (disseminated intravascular coagulation), or multiple organ failure; bedsore; burn; trauma injury; inflammatory bowel disease (e.g., ulcerative colitis, Crohn's disease, and the like); genetic disease; osteoporosis; arteriosclerosis; fibrosis (e.g., pulmonary fibrosis, liver fibrosis, and the like); interstitial pneumotitis; chronic hepatitis; liver cirrhosis; chronic renal insufficiency; renal glomerular sclerosis; and diabetes. In addition, EDG-1 is involved in preoperative, postoperative, and/or prognostic activation for blood vessel accompanying transplantation of various organs, tissues, and/or cells, for example, as an adhesion activation of transplanted organs, tissues, and/or cells in a case of heart transplantation, renal transplantation, dermal transplantation or liver transplantation, or the like.

In the present specification, an EDG-6-mediated disease means a disease in which EDG-6 is involved in onset, deterioration, healing, or the like of the disease. Examples of the disease include: rejection in transplantation; rejection of a transplanted organ; graft versus host disease; an autoimmune disease (e.g., systemic lupus erythematosus, rheumatoid arthritis, and the like); an allergic disease (e.g., atopic dermatitis, pollen disease, food allergy, and the like); asthma; inflammatory disease; infectious disease; ulcer; lymphoma; malignant tumor (e.g., cancer, and the like); leukemia; arteriosclerosis; multiple organ failure; and a disease associated with lymphocyte infiltration into a tissue such as ischemia-reperfusion injury.

In the present specification, the rejection includes an acute rejection occurring within 3 months, chronic rejection occurring thereafter, and graft versus host disease.

In the present specification, the graft means a transplanted organ (e.g., kidney, liver, heart, lung, and small intestine), a transplanted tissue (e.g., skin such as a full-thickness skin graft, an epidermal graft, a dermis graft, and a Davis graft; cornea; vessels; cord; bone; a fetal tissue; and the like) or transplanted cells (e.g., bone marrow cells, hematopoietic stem cells, peripheral blood stem cells, cord blood stem cells, pancreatic islet cells, Langerhans islet cells being part thereof, hepatocytes, neuronal cells, and intestinal epithelial cells). As preferable organs, kidney, liver, heart, and lung may be cited. As preferable tissues, skin, cornea, vessels, cord, and bones may be cited. As preferable cells, bone marrow cells, neurons, and pancreatic islet cells may be cited.

In the present specification, the autoimmune disease includes systemic lupus erythematosus, rheumatoid arthritis, multiple sclerosis, psoriasis, inflammatory bowel disease (e.g., ulcerative colitis, Crohn's disease, and the like), Behcet's disease, collagenosis, nephrotic syndrome, lupus nephritis, Sjoegren's syndrome, scleroderma, multiple myositis, mixed connective tissue disease, primary myxedema, Addison's disease, hypolastic anemia, autoimmune hemolytic anemia, idiopathic thrombocytopenic purpura, autoimmune thrombopenia, autoimmune diabetes (e.g., type I diabetes), uveitis, antireceptor disease, myasthenia gravis, thyrotoxicosis, thyroiditis, Hashimoto's disease and the like.

In the present specification, the allergic disease includes atopic dermatitis, rhinitis, conjunctivitis, pollen disease, food allergy, and the like. As a preferable allergic disease, atopic dermatitis, pollen disease, and food allergy may be cited.

In the present specification, the immunosuppressant means a drug which is mainly used for preventing and/or treating rejection in transplantation. As such the drug, there may be used, for example, an antimetabolite, an alkylating agent, a T cell activation inhibitor (i.e., a T cell function suppressor), a calcineurin inhibitor, a proliferation signal inhibitor, a steroid, an antibody used in immune suppression, other remedies for rejection, and the like. Those drugs are clinically used for autoimmune diseases.

In the present specification, the agent causing lymphopenia means a drug having effects of reducing lymphocytes in the peripheral blood, reducing circulating lymphocytes, reducing the amount of permeated lymphocytes, promoting the lymphocytes homing into a secondary lymphatic tissue, suppressing the recirculation of lymphocytes from lymph nods into the blood, inhibiting an enzyme in the nucleic acid synthesis pathway of lymphocytes (e.g., the pyrimidine metabolic system and the purine metabolic system) and the like.

In the present specification, the secondary lymphatic tissue includes lymph nods, Peyer's patch (e.g., an intestinal lymphatic tissue), spleen and the like.

In the present specification, the effect of promoting the lymphocytes homing into a secondary lymphatic tissue means promotion of the migration of lymphocytes into a secondary lymphatic tissue, enhancement of the separation of lymphocytes in a secondary lymphatic tissue, prolongation of the sustention of lymphocytes in a secondary lymphatic tissue and the like. Owing to those effects, lymphocytes can be reduced in a site suffering from inflammation or rejection, or the like. Moreover, the effect of protecting lymphocytes in the peripheral blood during cancer therapy can be expected. Here, the effect of protecting lymphocytes in the peripheral blood during cancer therapy means an effect of preliminarily homing lymphocytes in the peripheral blood into a secondary lymphatic tissue before a cancer therapy (in particular, chemotherapy, radiotherapy, etc.) to thereby protect the lymphocytes. This effect includes the protection of lymphocytes in pre-transplantation step of administering a large amount of an anticancer agent. It is known that the treatment of cancer by a chemotherapy, or the like with the use of an anticancer agent is accompanied by serious side effects such as the hypofunction of hematopoietic cells, thereby making a patient infectible. Such side effects can be lessened by the above-described function.

In the present specification, the side effect involved in the use of an immunosuppressant means renal disorder, liver disorder, infection, lymphoma, a circulatory disorder such as bradycardia or hypertension, diarrhea, emesis, alopecia, hirsutism, hyperlipidemia, a respiratory disorder, a central nervous system disorder, and an influence on an organ weight.

In the present specification, a "cyclic group" in a "cyclic group which may have a substituent(s)", which is represented by ring A or ring D, means a "carbocyclic group" or a "heterocyclic group".

The "carbocyclic group" means, for example, a "C3-15 carbocyclic group". The "C3-15 carbocyclic group" includes a "C3-15 mono-, bi—, or tricyclic carbocyclic group", and a "C3-15 bicyclic carbocyclic group having a spiro bond and C3-15 bridged bicyclic carbocyclic group". Examples of the "C3-15 mono-, bi—, or tricyclic carbocyclic group" include cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, naphthalene, dihydronaphthalene, tetrahydronaphthalene, perhydronaphthalene, 6,7-dihydro-5H-benzo[7]annulene, 5H-benzo[7]annulene, heptalene, perhydroheptalene, biphenylene, as-indacene, s-indacene, acenaphthylene, acenaphthene, fluorene, phenalene, phenanthrene, and anthracene rings. Examples of the "C3-15 bicyclic carbocyclic group having a spiro bond and C3-15 bridged bicyclic carbocyclic group" include spiro[4.4]nonane, spiro[4.5]decane, spiro[5.5]undecane, bicyclo[2.2.1]heptane, bicyclo[2.2.1]hept-2-ene, bicyclo[3.1.1]heptane, bicyclo[3.1.1]hept-2-ene, bicyclo[2.2.2]octane, bicyclo[2.2.2]oct-2-ene, adamantane, and noradamantane rings.

The "heterocyclic group" means, for example, a "3- to 15-membered heterocyclic group containing 1 to 5 nitrogen atoms, 1 or 2 oxygen atoms, and/or one sulfur atom". Examples of the "3- to 15-membered heterocyclic group which contains 1 to 5 nitrogen atoms, 1 or 2 oxygen atoms, and/or one sulfur atom" include: a "3- to 15-membered mono-, bi—, or tricyclic heterocyclic group which contains 1 to 5 nitrogen atoms, 1 or 2 oxygen atoms, and/or one sulfur atom"; and a "3- to 15-membered bicyclic heterocyclic group having a spiro bond and 3- to 15-membered bridged bicyclic heterocyclic group, each of which contains 1 to 5 nitrogen atoms, 1 or 2 oxygen atoms, and/or one sulfur atom". Examples of the "3- to 15-membered mono-, bi—, or tricyclic heterocyclic group which contains 1 to 5 nitrogen atoms, 1 or 2 oxygen atoms, and/or one sulfur atom", include pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazane, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazane, benzothiadiazole, benzotriazole, carbazole, β-carboline, acridine, phenazine, dibenzofuran, xanthene, dibenzothiophene, phenothiazine, phenoxazine, phenoxathiin, thianthrene, phenanthridine, phenanthroline, perimidine, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazane, tetrahydrofurazane, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, dioxaindan, benzodioxane, chromene, chroman, benzodithiolane, and benzodithiane rings. Examples of the "3- to 15-membered bicyclic heterocyclic group having a spiro bond and 3- to 15-membered bridged bicyclic heterocyclic group, each of which contains 1 to 5 nitrogen atoms, 1 or 2 oxygen atoms, and/or one sulfur atom" include azaspiro[4.4]nonane, oxazaspiro[4.4]nonane, oxazaspiro[2.5]octane, azaspiro[4.5]decane, 1,3,8-triazaspiro[4.5]decane, 2,7-diazaspiro[4.5]decane, 1,4,9-triazaspiro[5.5]undecane, oxazaspiro[4.5]decane, azaspiro[5.5]undecane, azabicyclo[2.2.1]heptane, azabicyclo[3.1.1]heptane, azabicyclo[3.2.1]octane (e.g., 8-azabicyclo[3.2.1]octane ring), azabicyclo[2.2.2]octane (e.g., azabicyclo[2.2.2]octane ring), and azabicyclo[2.1.1]hexane (e.g., 5-azabicyclo[2.1.1]hexane ring) rings.

In the present specification, the "C3-10 mono- or bicyclic carbocyclic group" in the "C3-10 mono- or bicyclic carbocyclic group which may have a substitutent" represented by ring A means any one of C3-10 mono- or bicyclic carbocyclic groups among the above-mentioned "C3-15 mono-, bi—, or tricyclic carbocyclic group". Examples thereof include cyclopropane, cyclobutane, cyclopentane, cyclohexane, cycloheptane, cyclooctane, cyclononane, cyclodecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, naphthalene, dihydronaphthalene, tetrahydronaphthalene, and perhydronaphthalene rings.

In the present specification, the "3- to 10-membered mono- or bicyclic heterocyclic group which contains 1 to 5 nitrogen atoms, 1 or 2 oxygen atoms, and/or one sulfur atom" in the "3- to 10-membered mono- or bicyclic heterocyclic group, which contains 1 to 5 nitrogen atoms, 1 or 2 oxygen atoms, and/or one sulfur atom, and which may have a substituent(s)" means any one of 3- to 10-membered mono- or bicyclic heterocyclic group among the above-mentioned "3- to 15-membered mono-, bi—, tricyclic heterocyclic group, which contains 1 to 5 nitrogen atoms, 1 or 2 oxygen atoms, and/or one sulfur atom". Examples thereof include pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazane, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzofurazane, benzothiadiazole, benzotriazole, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazane, tetrahydrofurazane, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzooxathiane, dihydrobenzooxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dioxolane, dioxane, dithiolane, dithiane, dioxaindan, benzodioxane, chromene, chromane, benzodithiolane, and benzodithiane rings.

In the present specification, the "C3-15 mono-, bi—, or tricyclic carbocyclic group" in the "C3-15 mono-, bi—, tricyclic carbocyclic group which may have a substituent(s)" represented by ring D has the same meaning as the above-mentioned "C3-15 mono-, bi—, or tricyclic carbocyclic group.

In the present specification, the "3- to 15-membered mono-, bi—, or tricyclic heterocyclic group which contains 1 to 5 nitrogen atoms, 1 or 2 oxygen atoms, and/or one sulfur atom" in the "3- to 15-membered mono-, bi—, or tricyclic heterocyclic group which contains 1 to 5 nitrogen atoms, 1 or 2 oxygen atoms, and/or one sulfur atom and which may have a substituent(s)" represented by ring D has the same meaning as the above-mentioned "3- to 15-membered mono-, bi—, or tricyclic heterocyclic group containing 1 to 5 nitrogen atoms, 1 or 2 oxygen atoms, and/or one sulfur atom".

In the present specification, an example of the "heterocyclic group containing at least one nitrogen atom" in the "heterocyclic group which contains at least one nitrogen atom and which may have a substituent(s)" represented by X is a "3- to 15-membered heterocyclic group which contains one nitrogen atom and which may further contain 1 to 4 nitrogen atoms, 1 or 2 oxygen atoms, and/or one sulfur atom". Examples of the "3- to 15-membered heterocyclic group which contains one nitrogen atom and which may further contain 1 to 4 nitrogen atoms, 1 or 2 oxygen atoms, and/or one sulfur atom" include: a "3- to 15-membered mono-, bi—, or tricyclic heterocyclic group which contains one nitrogen atom and which may further contain 1 to 4 nitrogen atoms, 1 or 2 oxygen atoms, and/or one sulfur atom"; and a "3- to 15-membered bicyclic heterocyclic group having a spiro bond and 3- to 15-membered bridged bicyclic heterocyclic group, each of which contains one nitrogen atom and which may further contain 1 to 4 nitrogen atoms, 1 or 2 oxygen atoms, and/or one sulfur atom". Examples of the "3- to 15-membered mono-, bi—, or tricyclic heterocyclic group, which contains one nitrogen atom, and which may further contain 1 to 4 nitrogen atoms, 1 or 2 oxygen atoms, and/or one sulfur atom", include pyrrole, imidazole, triazole, pyrazole, azepine, diazepine, indole, isoindole, indazole, purine, pyrrolopyridine, benzimidazole, benzazepine, benzodiazepine, benzotriazole, carbazole, β-carboline, phenothiazine, phenoxazine, pyrazoloisoquinoline, pyrazolonaphthyridine, pyrimidoindole, indolidinoindole, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazane, tetrahydrofurazane, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, tetrahydropyrrolopyridine, dihydrocinnoline, tetrahydrocinnoline, perhydrocinnoline, dihydrobenzooxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine (2,3,4,5-tetrahydro-1H-2-benzazepine, 2,3,4,5-tetrahydro-1H-3-benzazepine, etc.), dihydrobenzodiazepine, tetrahydrobenzodiazepine, dihydrobenzoxazepine, tetrahydrobenzoxazepine, dihydrocarbazole, tetrahydrocarbazole, perhydrocarbazole, dihydroacridine, tetrahydroacridine, perhydroacridine, tetrapyridonaphthyridine, tetrahydro-β-carboline, dihydroazepinoindole, hexahydroazepinoindole, tetrahydropyrazoloisoquinoline, tetrahydropyrazolonaphthyridine, dihydroazepinoindazole, hexahydroazepinoindazole, dihydropyrazolopyridoazepine, hexahydropyrazolopyridoazepine, tetrahydropyrimidoindole, dihydrothiadinoindole, tetrahydrothiadinoindole, dihydrooxadinoindole, tetrahydrooxadinoindole, hexahydroindolydinoindole, dihydroindolobenzodiazepine, octahydroindoloquinolizine, hexahydroimidazopyridoindole, and hexahydropyrrolothiazepinoindole rings. Examples of the "3- to 15-membered bicyclic heterocyclic group having a spiro bond and 3- to 15-membered bridged bicyclic heterocyclic group, each of which contains one nitrogen atom, and may further contain 1 to 4 nitrogen atoms, 1 or 2 oxygen atoms, and/or one sulfur atom" include azaspiro[4.4]nonane, oxazaspiro[4.4]nonane, oxazaspiro[2.5]octane, azaspiro[4.5]decane, 1,3,8-triazaspira[4.5]decane, 2,7-diazaspiro[4.5]decane, 1,4,9-triazaspiro[5.5]undecane, oxazaspiro[4.5]decane, azaspiro[5.5]undecane, azabicyclo[2.2.1]heptane, azabicyclo[3.1.1]heptane, azabicyclo[3.2.1]octane (8-azabicyclo[3.2.1]octane, etc.), azabicyclo[2.2.2]octane (2-azabicyclo[2.2.2]octane, etc.), and azabicyclo[2.1.1]hexane (5-azabicyclo[2.1.1]hexane, etc.) rings.

In the present specification, the "4- to 8-membered monocyclic heterocyclic group containing at least one nitrogen atom" in the "4- to 8-membered monocyclic heterocyclic group containing at least one nitrogen atom and which may have a substituent(s)" represented by X means any one of 4- to 8-membered monocyclic heterocyclic groups among the above-mentioned "heterocyclic group which contains at least one nitrogen atom". Examples thereof include pyrrole, imidazole, triazole, pyrazole, azepine, diazepine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrooxazole, tetrahydrooxazole (i.e., oxazolidine), dihydroisoxazole, tetrahydroisoxazole (i.e., isoxazolidine), dihydrothiazole, tetrahydrothiazole (i.e., thiazolidine), dihydroisothiazole, tetrahydroisothiazole (i.e., isothiazolidine), dihydrofurazan, tetrahydrofurazan, dihydrooxadiazole, tetrahydrooxadiazole (i.e., oxadiazoline), dihydrooxazine, tetrahydrooxazine, dihydrooxadiazine, tetrahydrooxadiazine, dihydrooxazepine, tetrahydrooxazepine, perhydrooxazepine, dihydrooxazepine, tetrahydrooxazepine, perhydrooxadiazepine, dihydrothiadiazole, tetrahydrothiadiazole (i.e., thiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, and oxathiane rings.

In the present specification, the "substituent" in the "cyclic group which may have a substituent(s)" or the like is not particularly limited, so long as it is a substituent. Examples of the substituent include (1) C1-20 alkyl which may be substituted, (2) C2-20 alkenyl which may be substituted, (3) C2-20 alkynyl which may be substituted, (4) C1-20 alkylidene which may be substituted, (5) a cyclic group which may be substituted, (6) oxo, (7) hydroxy, (8) C1-20 alkyloxy which may be substituted, (9) C2-20 alkenyloxy which may be substituted, (10) C2-20 alkynyloxy which may be substituted, (11) hydroxy which is protected by a cyclic group which may be substituted, (12) C1-20 acyloxy which may be substituted, (13) thioxo, (14) mercapto, (15) C1-20 alkylthio which may be substituted, (16) C2-20 alkenylthio which may be substituted, (17) C2-20 alkynylthio which may be substituted, (18) mercapto substituted with a cyclic group which may be substituted, (19) C1-20 alkylsulfinyl which may be substituted, (20) C2-20 alkenylsulfinyl which may be substituted, (21) C2-20 alkynylsulfinyl which may be substituted, (22) sulfinyl substituted with a cyclic group which may be substituted, (23) C1-20 alkylsulfonyl which may be substituted, (24) C2-20 alkenylsulfonyl which may be substituted, (25) C2-20 alkynylsulfonyl which may be substituted, (26) sulfonyl substituted with a cyclic group which may be substituted, (27) sulfino which may be substituted, (28) sulfo which may be substituted, (29) sulfamoyl which may be substituted (when the substituents are two, they may be taken together with a nitrogen atom to which they are bound to form a 5- to 7-membered monocyclic heterocyclic group containing 1 to 5 nitrogen atoms, one oxygen atom and/or one sulfur atom (this heterocyclic group may be substituted by C1-8 alkyl, hydroxy, or amino)), (30) carbonyl which may be substituted, (31) C1-20 acyl which may be substituted, (32) carbamoyl which may be substituted (when the substituents are two, they may be taken together with a nitrogen atom to which they are bound to form a 5- to 7-membered monocyclic heterocyclic group containing 1 to 5 nitrogen atoms, one oxygen atom and/or one sulfur atom (this heterocyclic group may be substituted by C1-8 alkyl, hydroxy, or amino)), (33) cyano, (34) amidino which may be substituted (when the substituents are two, they may be taken together with a nitrogen atom to which they are bound to form a 5- to 7-membered monocyclic heterocyclic group containing 1 to 5 nitrogen atoms, one oxygen atom and/or one sulfur atom (this heterocyclic group may be substituted by C1-8 alkyl, hydroxy, or amino)), (35) nitro, (36) nitroso, (37) imino which may be substituted, (38) amino which may be substituted (when the substituents are two, they may be taken together with a nitrogen atom to which they are bound to form a 5- to 7-membered monocyclic heterocyclic group containing 1 to 5 nitrogen atoms, one oxygen atom and/or one sulfur atom (this heterocyclic group may be substituted by C1-8 alkyl, hydroxy, or amino)), and (39) a halogen atom, and the like.

In the present specification, the "substituent" in the above-mentioned "C1-20 alkyl which may be substituted" or the like is, for example, (1) C1-20 alkyl, (2) C2-20 alkenyl, (3) C2-20 alkynyl, (4) C1-20 alkylidene, (5) a cyclic group, (6) C1-20 alkyl substituted with a cyclic group, (7) oxo, (8) hydroxy, (9) C1-20 alkyloxy, (10) C2-20 alkenyloxy, (11) C2-20 alkynyloxy, (12) hydroxy protected by a cyclic group, (13) C1-20 acyloxo, (14) thioxo, (15) mercapto, (16) C1-20 alkylthio, (17) C2-20 alkenylthio, (18) C2-20 alkynylthio, (19) mercapto substituted with a cyclic group, (20) C1-20 alkylsulfinyl, (21) C2-20 alkenylsulfinyl, (22) C2-20 alkynylsulfinyl, (23) sulfinyl substituted with a cyclic group, (24) C1-20 alkylsulfonyl, (25) C2-20 alkenylsulfonyl, (26) C2-20 alkynylsulfonyl, (27) sulfonyl substituted with a cyclic group, (28) C1-20 alkylsulfonyl substituted with a cyclic group, (29) sulfino, (30) sulfo, (31) sulfamoyl, (32) C1-20 acyl, (33) C1-20 acyl substituted with a cyclic group, (34) carbonyl substituted with a cyclic group, (35) carbamoyl, (36) cyano, (37) amidino, (38) nitro, (39) nitroso, (40) imino, (41) amino, and (42) a halogen atom or the like. They may exist at any substitutable positions and any acceptable number of substituents may exist.

In the present specification, the "C1-20 alkyl" includes methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, and isomers thereof.

In the present specification, the "C1-8 alkyl" includes methyl, ethyl, propyl, butyl, pentyl, hexyl, heptyl, octyl, and isomers thereof.

In the present specification, the "C2-20 alkenyl" includes ethenyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, icosenyl, and isomers thereof.

In the present specification, the "C2-20 alkynyl" includes ethynyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, icosynyl, and isomers thereof.

In the present specification, the "C1-20 alkylidene" includes methylidene, ethylidene, propylidene, butylidene, pentylidne, hexylidene, heptylidene, octylidene, nonylidene, decylidene, undecylidene, dodecylidene, tridecylidene, tetradecylidene, pentadecylidene, hexadecylidene, heptadecylidene, octadecylidene, nonadecylidene, icosylidene, and isomers thereof.

In the present specification, the "C1-20 alkyloxy" includes methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, heptadecyloxy, octadecyloxy, nonadecyloxy, icosyloxy, and isomers thereof.

In the present specification, the "C1-8 alkoxy" includes methoxy, ethoxy, propoxy, butoxy, pentyloxy, hexyloxy, heptyloxy, octyloxy, and isomers thereof.

In the present specification, the "C1-4 alkoxy" includes methoxy, ethoxy, propoxy, butoxy, and isomers thereof.

In the present specification, the "C2-20 alkenyloxy" includes ethenyloxy, propenyloxy, butenyloxy, pentenyloxy, hexenyloxy, heptenyloxy, octenyloxy, nonenyloxy, decenyloxy, undecenyloxy, dodecenyloxy, tridecenyloxy, tetradecenyloxy, pentadecenyloxy, hexadecenyloxy, heptadecenyloxy, octadecenyloxy, nonadecenyloxy, icosenyloxy, and isomers thereof.

In the present specification, the "C2-20 alkynyloxy" includes ethynyloxy, propynyloxy, butynyloxy, pentynyloxy, hexynyloxy, heptynyloxy, octynyloxy, nonynyloxy, decynyloxy, undecynyloxy, dodecynyloxy, tridecynyloxy, tetradecynyloxy, pentadecynyloxy, hexadecynyloxy, heptadecynyloxy, octadecynyloxy, nonadecynyloxy, icosynyloxy, and isomers thereof.

In the present specification, the "C1-20 alkylthio" includes methylthio, ethylthio, propylthio, butylthio, pentylthio, hexylthio, heptylthio, octylthio, nonylthio, decylthio, undecylthio, dodecylthio, tridecylthio, tetradecylthio, pentadecylthio, hexadecylthio, heptadecylthio, octadecylthio, nonadecylthio, icosylthio, and isomers thereof.

In the present specification, the "C2-20 alkenylthio" includes ethenylthio, propenylthio, butenylthio, pentenylthio, hexenylthio, heptenylthio, octenylthio, nonenylthio, decenylthio, undecenylthio, dodecenylthio, tridecenylthio, tetradecenylthio, pentadecenylthio, hexadecenylthio, heptadecenylthio, octadecenylthio, nonadecenylthio, icosenylthio, and isomers thereof.

In the present specification, the "C2-20 alkynylthio" includes ethynylthio, propynylthio, butynylthio, pentynylthio, hexynylthio, heptynylthio, octynylthio, nonynylthio, decynylthio, undecynylthio, dodecynylthio, tridecynylthio, tetradecynylthio, pentadecynylthio, hexadecynylthio, heptadecynylthio, octadecynylthio, nonadecynylthio, icosynylthio, and isomers thereof.

In the present specification, the "C1-20 alkylsulfinyl" includes methylsulfinyl, ethylsulfinyl, propylsulfinyl, butylsulfinyl, pentylsulfinyl, hexylsulfinyl, heptylsulfinyl, octylsulfinyl, nonylsulfinyl, decylsulfinyl, undecylsulfinyl, dodecylsulfinyl, tridecylsulfinyl, tetradecylsulfinyl, pentadecylsulfinyl, hexadecylsulfinyl, heptadecylsulfinyl, octadecylsulfinyl, nonadecylsulfinyl, icosylsulfinyl, and isomers thereof.

In the present specification, the "C2-20 alkenylsulfinyl" includes ethenylsulfinyl, propenylsulfinyl, butenylsulfinyl, pentenylsulfinyl, hexenylsulfinyl, heptenylsulfinyl, octenylsulfinyl, nonenylsulfinyl, decenylsulfinyl, undecenylsulfinyl, dodecenylsulfinyl, tridecenylsulfinyl, tetradecenylsulfinyl, pentadecenylsulfinyl, hexadecenylsulfinyl, heptadecenylsulfinyl, octadecenylsulfinyl, nonadecenylsulfinyl, icosenylsulfinyl, and isomers thereof.

In the present specification, the "C2-20 alkynylsulfinyl" includes ethynylsulfinyl, propynylsulfinyl, butynylsulfinyl, pentynylsulfinyl, hexynylsulfinyl, heptynylsulfinyl, octynylsulfinyl, nonynylsulfinyl, decynylsulfinyl, undecynylsulfinyl, dodecynylsulfinyl, tridecynylsulfinyl, tetradecynylsulfinyl, pentadecynylsulfinyl, hexadecynylsulfinyl, heptadecynylsulfinyl, octadecynylsulfinyl, nonadecynylsulfinyl, icosynylsulfinyl, and isomers thereof.

In the present specification, the "C1-20 alkylsulfonyl" includes methylsulfonyl, ethylsulfonyl, propylsulfonyl, butylsulfonyl, pentylsulfonyl, hexylsulfonyl, heptylsulfonyl, octylsulfonyl, nonylsulfonyl, decylsulfonyl, undecylsulfonyl, dodecylsulfonyl, tridecylsulfonyl, tetradecylsulfonyl, pentadecylsulfonyl, hexadecylsulfonyl, heptadecylsulfonyl, octadecylsulfonyl, nonadecylsulfonyl, icosylsulfonyl, and isomers thereof.

In the present specification, the "C2-20 alkenylsulfonyl" includes ethenylsulfonyl, propenylsulfonyl, butenylsulfonyl, pentenylsulfonyl, hexenylsulfonyl, heptenylsulfonyl, octenylsulfonyl, nonenylsulfonyl, decenylsulfonyl, undecenylsulfonyl, dodecenylsulfonyl, trideceriylsulfonyl, tetradecenylsulfonyl, pentadecenylsulfonyl, hexadecenylsulfonyl, heptadecenylsulfonyl, octadecenylsulfonyl, nonadecenylsulfonyl, icosenylsulfonyl, and isomers thereof.

In the present specification, the "C2-20 alkynylsulfonyl" includes ethynylsulfonyl, propynylsulfonyl, butynylsulfonyl, pentynylsulfonyl, hexynylsulfonyl, heptynylsulfonyl, octynylsulfonyl, nonynylsulfonyl, decynylsulfonyl, undecynylsulfonyl, dodecynylsulfonyl, tridecynylsulfonyl, tetradecynylsulfonyl, pentadecynylsulfonyl, hexadecynylsulfonyl, heptadecynylsulfonyl, octadecynylsulfonyl, nonadecynylsulfonyl, icosynylsulfonyl, and isomers thereof.

In the present specification, the "C1-20 acyl" includes methanoyl, ethanoyl, propanoyl, butanoyl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, icosanoyl, and isomers thereof.

In the present specification, the "C1-20 acyloxy" includes methanoyloxy, ethanoyloxy, propanoyloxy, butanoyloxy, pentanoyloxy, hexanoyloxy, heptanoyloxy, octanoyloxy, nonanoyloxy, decanoyloxy, undecanoyloxy, dodecanoyloxy, tridecanoyloxy, tetradecanoyloxy, pentadecanoyloxy, hexadecanoyloxy, heptadecanoyloxy, octadecanoyloxy, nonadecanoyloxy, icosanoyloxy, and isomers thereof.

In the present specification, the "protecting group" in the "hydroxy which may be protected" or the "amino which may be protected" has the same meaning as the "substituent" in the above-mentioned "C1-20 alkyl which may be substituted" or the like.

In the present specification, the "cyclic group" in the above-mentioned "substituted by a cyclic group" or the like has the same meaning as the "cyclic group" in the above-mentioned "cyclic group which may have a substituent(s)" represented by ring A and ring D.

In the present specification, the "cyclic group" in the "hydroxy protected by a cyclic group" has the same meaning as the "cyclic group" in the above-mentioned "cyclic group which may have a substituent(s)" represented by ring A and ring D.

In the present specification, the "cyclic group" in the "cyclic group which may be substituted" has the same meaning as the "cyclic group" in the above-mentioned "cyclic group which may have a substituent(s)" represented by ring A and ring D.

In the present specification, the "cyclic group" in the "substituent" of the above-mentioned "C1-20 alkyl which may be substituted" has the same meaning as the "cyclic group" in the above-mentioned "cyclic group which may have a substituent(s)" represented by ring A and ring D.

In the present specification, the "halogen atom" includes fluorine, chlorine, bromine, and iodine.

In the present specification, the "bond" represented by E, G, or M means that the atoms are directly bound without intermediation of any other atom.

In the present specification, the "spacer having 1 to 8 atoms in its main chain" represented by E or G means spacing in which 1 to 8 atoms are continuously linked in its main chain. In this case, the "number of atoms as a main chain" should be counted such that the atoms in its main chain become minimum. The "spacer having 1 to 8 atoms in its main chain" includes a divalent group having 1 to 8 atoms in its main chain which is composed of 1 to 8 combinations selected from the group consisting of C1-8 alkylene which may be substituted, a C2-8 alkenylene which may be substituted, C2-8 alkynylene which may be substituted, —CO—, an oxygen atom (—O—), a sulfur atom which may be oxidized (—S—, —SO—, and —SO$_2$—), a nitrogen atom which may be substituted (—NH—), -(carbocyclic group which may have a substituent(s))-, -(heterocyclic group which may have a substitutent(s))-, and the like.

In the present specification, the "spacer having 1 to 4 atoms in its main chain" represented by G means spacing in which 1 to 4 atoms are continuously linked in its main chain. In this case, the "number of atoms as a main chain" should be counted such that the atoms in its main chain become minimum. Examples of the "spacer having 1 to 4 atoms in its main chain" include a divalent group and the like each of which has 1 to 4 atoms in its main chain and 1 to 4 combinations selected from the group consisting of C1-4 alkylene which may be substituted, C2-4 alkenylene which may be substituted, C2-4 alkinylene which may be substituted, —CO—, an oxygen atom (—O—), a sulfur atom which may be oxidized (—S—, —SO—, and —SO₂—), a nitrogen atom which may be substituted (—NH—), -(a carbocyclic group which may have a substituent(s))-, -(a heterocyclic group which may have a substitutent(s))-, and the like.

In the present specification, the "C1-8 alkylene" includes methylene, ethylene, trimethylene, tetramethylene, pentamethylene, hexamethylene, heptamethylene, octamethylene, and isomers thereof.

In the present specification, the "C1-7 alkylene" includes methylene, ethylene, trimethylene, tetramethylene, pentamethylene, hexamethylene, heptamethylene, and isomers thereof.

In the present specification, the "C1-4 alkylene" includes methylene, ethylene, trimethylene, tetramethylene, and isomers thereof.

In the present specification, the "C1-3 alkylene" includes methylene, ethylene, trimethylene, and isomers thereof.

In the present specification, the "C2-8 alkenylene" includes ethenylene, propenylene, butenylene, pentenylene, hexenylene, heptenylene, octenylene, and isomers thereof.

In the present specification, the "C2-4 alkenylene" includes ethenylene, propenylene, butenylene, and isomers thereof.

In the present specification, the "C2-3 alkenylene" includes ethenylene, propenylene, and isomers thereof.

In the present specification, the "C2-8 alkynylene" includes ethynylene, propynylene, bytynylene, pentynylene, hexynylene, heptynylene, octynylene, and isomers thereof.

In the present specification, the "C2-3 alkynylene" includes ethynylene, propynylene, and isomers thereof.

In the present specification, the "C2-4 alkynylene" includes ethynylene, propynylene, bytynylene, and isomers thereof.

In the present specification, the "substituent" in the "C1-8 alkylene which may be substituted" or the like represented by E or G has the same meaning as the "substituent" in the above-mentioned "C1-20 alkyl which may be substituted" or the like.

In the present specification, the "carbocyclic group" in the "carbocyclic group which may have a substituent(s)" has the same meaning as the "carbocyclic group" represented by the "cyclic ring" in the above-mentioned "cyclic group which may have a substituent(s)" represented by ring A and ring D.

In the present specification, the "heterocyclic group" in the "heterocyclic group which may have a substituent(s)" has the same meaning as the "heterocyclic group" represented by the "cyclic group" in the above-mentioned "cyclic group which may have a substituent(s)" represented by ring A and ring D.

In the present specification, the "substituent" in the "carbocyclic group which may have a substituent(s)" or the "heterocyclic group which may have a substituent(s)" has the same meaning as the "substituent" in the above-mentioned "cyclic group which may have a substituent(s)" represented by ring A and ring D.

In the present specification, the "sulfur atom which may be oxidized" means —S—, —SO—, or —SO₂—.

In the present specification, the "substituent" in the "amino which may have a substituent(s)" represented by X has the same meaning as the "substituent" in the above-mentioned "cyclic group which may have a substituent(s)" or the like. However, the substituent does not represent a carboxyl group or a group substituted by a carboxyl group.

In the present specification, the "substituent" in the "heterocyclic group which contains at least one nitrogen atom and which may have a substituent(s)" represented by X has the same meaning as the "substituent" in the above-mentioned "amino which may have a substituent(s)".

In the present specification, the "substituent" in the "4- to 8-membered monocyclic heterocyclic group which contains at least one nitrogen atom and which may have a substituent(s)" represented by X has the same meaning as the "substituent" in the above-mentioned "amino which may have a substituent(s)".

In the present specification, the "substituent" represented by L has the same meaning as the "substituent" in the above-mentioned "cyclic group which may have a substituent(s)" or the like.

In the present specification, the "substituent" represented by R has the same meaning the "substituent" in the above-mentioned "cyclic group which may have a substituent(s)" or the like. However, the substituent does not represent the "cyclic group which may be substituted".

In the present specification, the "substituent" represented by $R^1$ or $R^2$ has the same meaning as the "substituent" in the above-mentioned "amino which may have a substituent(s)", or represents any one of the following:

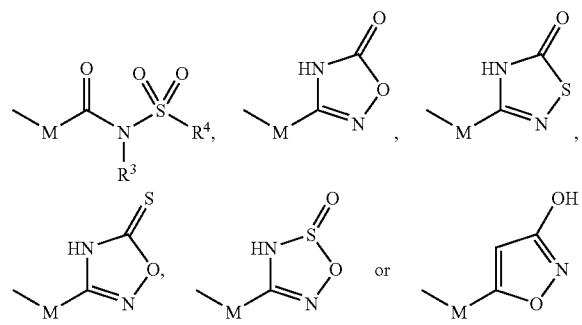

wherein all symbols have the same meanings as described above.

In the present specification, the "substituent" represented by $R^3$ or $R^4$ is not particularly limited as long as it is a substituent. Examples thereof include the following substituents: C1-20 alkyl which may be substituted, C2-20 alkenyl which may be substituted, C2-20 alkynyl which may be substituted, a cyclic group which may be substituted, oxo, hydroxy, C1-20 alkyloxy which may be substituted, C2-20 alkenyloxy which may be substituted, C2-20 alkynyloxy which may be substituted, hydroxy protected by a cyclic group which may be substituted, C1-20 acyloxy which may be substituted, thioxo, carbonyl which may be substituted, C1-20 acyl which may be substituted, carbamoyl which may be substituted (when the substituents are two, they may be taken together with a nitrogen atom to which they are bound to form a 5- to 7-membered monocyclic heterocyclic group containing 1 to 5 nitrogen atoms, one oxygen atom, and/or one sulfur atom (this heterocyclic group may be substituted by C1-8 alkyl, hydroxy, or amino)), cyano, and amino which may be substituted (when the substituents are two, they may be taken together with a nitrogen atom to which they are bound to form a 5- to 7-membered monocyclic heterocyclic group containing 1 to 5 nitrogen atoms, one oxygen atom, and/or one sulfur atom (this heterocyclic group may be substituted with C1-8 alkyl, hydroxy, or amino)).

In the present invention, ring A preferably represents a "C3-10 mono- or bicyclic carbocyclic group which may have a substituent(s)" or a "3- to 10-membered mono- or bicyclic heterocyclic group which contains 1 to 5 nitrogen atoms, 1 or 2 oxygen atoms, and/or one sulfur atom and which may have a substituent(s)", more preferably a "C5-7 monocyclic carbocyclic group which may have a substituent(s)" or a "5- to 7-membered monocyclic heterocyclic group which contains 1 to 5 nitrogen atoms, 1 or 2 oxygen atoms, and/or one sulfur atom and which may have a substituent(s)", and most preferably a "benzene, pyridine, thiophene, thiazole, oxadiazole, or cyclohexane ring which may have a substituent(s)", with a "benzene, pyridine, oxadiazole, or cyclohexane ring which may have a substituent(s)" being extremely preferable. In addition, examples of the "substituent" in this case preferably include "C1-4 alkyl which may be substituted by 1 to 3 halogen atoms", "C1-8 alkoxy which may be substituted", and a "halogen atom", and more preferably methyl, methoxy, propoxy, isopropoxy, isobutyloxy, difluoromethoxy, trifluoromethyl, a fluorine atom, and a chlorine atom.

In the present invention, R preferably represents "C1-20 alkyl which may be substituted", "C1-20 alkyloxy which may be substituted", and a "halogen atom", more preferably "C1-8 alkyl which may be substituted", "C1-8 alkoxy which may be substituted", and a "halogen atom", and most preferably "methyl", "ethyl", "propyl", "butyl", "isobutyl", "trifluoromethyl", "methoxy", "propoxy", "isopropoxy", "isobutyloxy", "difluoromethoxy", a "fluorine atom", and a "clorine atom".

In the present invention, ring D preferably represents a "C3-15 mono-, bi—, or tricyclic carbocyclic group which may have a substituent(s)" and a "3- to 15-membered mono-, bi—, or tricyclic heterocyclic group which contains 1 to 5 nitrogen atoms, 1 or 2 oxygen atoms, and/or one sulfur atom and which may have a substituent(s)", more preferably any one of the following:

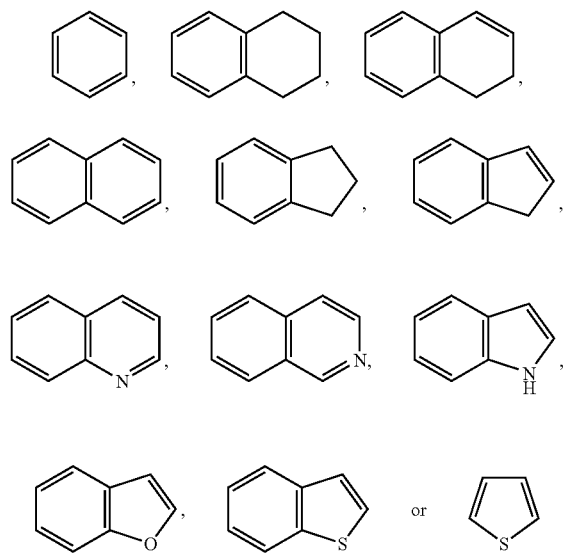

which may have a substituent(s), and most preferably a "benzene, dihydronaphthalene, or naphthalene ring which may have a substituent(s)", with the following being particularly preferable:

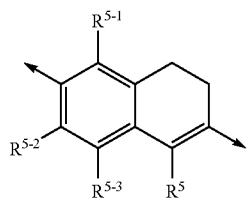

wherein all symbols have the same meaning as described above. In addition, examples of the "substituent" or $R^5$ in this case preferably include "C1-4 alkyl which may be substituted by 1 to 3 halogen atoms" and a "halogen atom", and more preferably methyl, trifluoromethyl, and a chlorine atom.

In the present invention, E preferably represents a "bond" or a "spacer having 1 to 8 atoms in its main chain which is 1 to 8 combinations selected from the group consisting of C1-8 alkylene which may be substituted, C2-8 alkenylene which may be substituted, an oxygen atom, a sulfur atom which may be oxidized, and a nitrogen atom which may be substituted", more preferably "C1-8 alkylene which may be substituted" and "—(C1-7 alkylene which may be substituted)-(oxygen atom)-", and most preferably "-(methylene which may be substituted)-(oxygen atom)-" and "-(trimethylene which may be substituted)-(oxygen atom)-". In addition, examples of the "substituent" in this case preferably include "C1-4 alkyl" and "C1-4 alkoxy", and more preferably methyl.

In the present invention, G preferably represents a "bond" or a "spacer having 1 to 4 atoms in its main chain", more preferably a "spacer having 1 to 4 atoms in its main chain which is 1 to 4 combinations selected from the group consisting of C1-3 alkylene which may be substituted, C2-3 alkenylene which may be substituted, an oxygen atom, and a sulfur atom which may be oxidized", and most preferably "methylene which may be substituted, ethylene which may be substituted, trimethylene which may be substituted, vinylene which may be substituted, and propenylene which may be substituted". In addition, examples of the "substituent" in this case preferably include "oxo" and "C1-4 alkyl which may be substituted by 1 to 3 halogen atoms or C1-4 alkoxy", and more preferably "oxo".

In the present invention, L preferably represents a "hydrogen atom", "C1-20 alkyl which may be substituted", "C1-20 alkyloxy which may be substituted", and a "halogen atom", more preferably a "hydrogen atom", "C1-8 alkyl which may be substituted", "C1-8 alkoxy which may be substituted", and a "halogen atom", and most preferably a "hydrogen atom", "methyl", "ethyl", "propyl", "butyl", "isobutyl", "trifluoromethyl", "methoxy", "propoxy", "isopropoxy", "difluoromethoxy", a "fluorine atom", and a "chlorine atom". In addition, examples of the "substituent" in this case preferably include "oxo", "hydroxy which may be protected", and a "halogen atom".

In the present invention, X preferably represents the following:

wherein all symbols have the same meaning as described above, and a "heterocyclic group which contains at least one nitrogen atom and which may have a substituent(s)".

In the present invention, a "heterocyclic group which contains at least one nitrogen atom and which may have a substituent(s)" represented by X preferably represents a "4- to 8-membered monocyclic heterocyclic group which contains at least one nitrogen atom and which may have a substituent(s)", more preferably "azetidine, pyrrolidine, piperidine, perhydroazepine, piperazine, morpholine, thiomorpholine, and thiazolidine rings each of which may have a substituent(s)", and most preferably "azetidine, pyrrolidine, piperazine, and piperidine rings each of which may have a substituent(s)". In addition, examples of the "substituent" in this case preferably include "oxo", "hydroxy which may be protected", "alkyl which may be substituted by 1 to 3 halogen atoms or hydroxy which may be protected", "amide which may be substituted", a "benzene ring which may be substituted by C1-4 alkyl, C1-4 alkoxy, trifluoromethyl, trifluoromethoxy, fluorine atom, chlorine atom, cyano, or the like", a "4- to 8-membered monocyclic heterocyclic group which contains at least one nitrogen atom and which may be substituted by C1-4 alkyl, C1-4 alkoxy, trifluoromethyl, trifluoromethoxy, fluorine atom, chlorine atom, cyano, or the like", and the following:

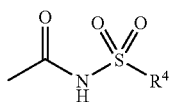

wherein all symbols have the same meanings as described above.

In the present invention, $R^1$ and $R^2$ each preferably represent "C1-4 alkyl which may be substituted", a "cyclic group which may have a substituent(s)", and any one of the followings:

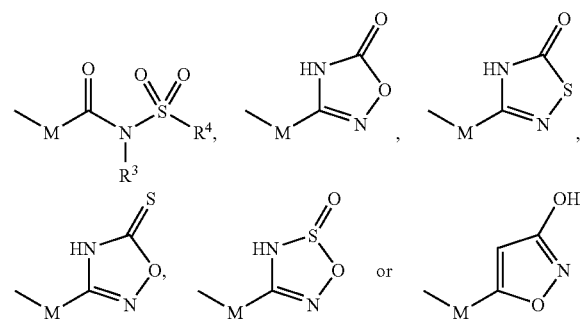

wherein all symbols have the same meanings as described above, more preferably "C1-4 alkyl which may be substituted", "phenyl which may have a substituent(s)", and the following:

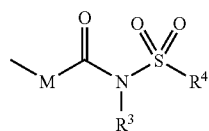

wherein all symbols have the same meanings as described above, and most preferably "methyl", "ethyl", "propyl", "hydroxypropyl", "phenyl which may have a substituent(s)", and the following:

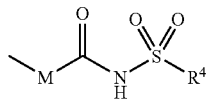

wherein all symbols have the same meanings as described above. In addition, examples of the "substituent" in this case preferably include "oxo", "hydroxy which may be protected", "cyano", and a "halogen atom".

In the present invention, $R^3$ preferably represents a "hydrogen atom" and "methyl", and more preferably a "hydrogen atom".

In the present invention, $R^4$ preferably represents a "cyclic group which may be substituted", more preferably a "C3-10 mono- or bicyclic carbocyclic group which may be substituted or 3- to 10-membered mono- or bicyclic heterocyclic group which contains 1 to 5 nitrogen atoms, 1 or 2 oxygen atoms, and/or one sulfur atom and which may be substituted", and most preferably "phenyl and isoxazole each of which may be substituted". In addition, examples of the "substituent" in this case preferably include "C1-4 alkyl which may be substituted by 1 to 3 halogen atoms or hydroxy which may be protected" and a "halogen atom".

In the present invention, M preferably represents "C1-4 alkylene which may be substituted", and more preferably "ethylene which may be substituted".

In the present invention, Q preferably represents "methylene which may be substituted" and "trimethylene which may be substituted", and more preferably methylene and —$CH_2$—$CHR^6$—$CH_2$—.

In the present invention, $R^6$ preferably represents a hydrogen atom, methyl, hydroxy, and methoxy, and more preferably methyl.

In the present invention, n preferably represents 0 or 1 to 3, and more preferably 1.

In the present invention, m preferably represents 1 or 2.

Among the compounds of the present invention represented by formula (I), preferable compounds include a compound represented by formula (I-1):

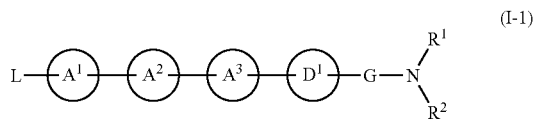

wherein ring $A^1$, ring $A^2$, and ring $A^3$ each independently has the same meaning as ring A, and ring $D^1$ represents any one of the followings:

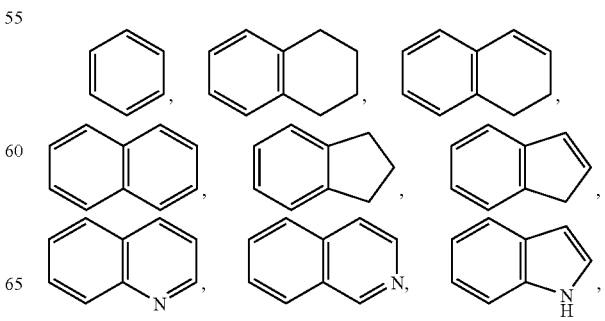

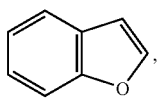 , 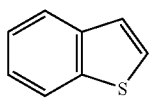 or 

which may have a substituent(s), and other symbols have the same meanings as described above, a compound represented by formula (I-2):

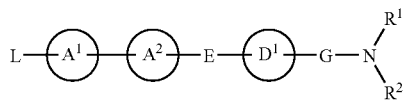

(I-2)

wherein all symbols have the same meaning as described above, a compound represented by formula (I-3):

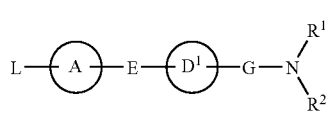

(I-3)

wherein all symbols have the same meaning as described above, a compound represented by formula (I-4):

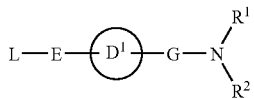

(I-4)

wherein all symbols have the same meaning as described above, a compound represented by formula (I-5):

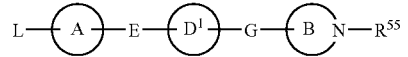

(I-5)

wherein ring B represents a heterocyclic group which contains at least one nitrogen atom and which may be substituted, $R^{55}$ represents a hydrogen atom or a substituent binding to the nitrogen atom on the ring B, and other symbols have the same meanings as described above, and a compound represented by formula (I-6):

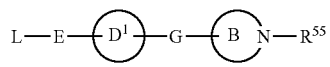

(I-6)

wherein all symbols have the same meanings as described above, a salt thereof, an N-oxide form thereof, a solvate thereof, and a prodrug thereof.

Among the compounds of the present invention represented by formula (I), more preferable compounds include a compound represented by formula (I-2-1):

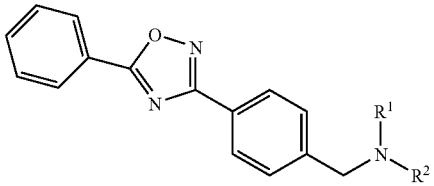

(I-2-1)

wherein benzene ring may have any acceptable number of substituents at any substitutable positions in addition to those described above, the substituent has the same meaning as the "substituent" in the "cyclic group which may have a substituent(s)", and other symbols have the same meanings as described above, a compound represented by formula (I-3-1):

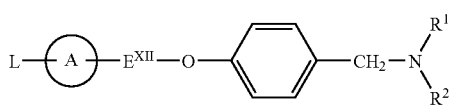

(I-3-1)

wherein $E^{XII}$ has the same meaning as E, and the number of which atoms in its main chain is one smaller than that of E, benzene ring may have any acceptable number of substituents at any substitutable positions in addition to those described above, the substituent has the same meaning as the "substituent" in the "cyclic group which may have a substituent(s)", and other symbols have the same meanings as described above, a compound represented by formula (I-3-2):

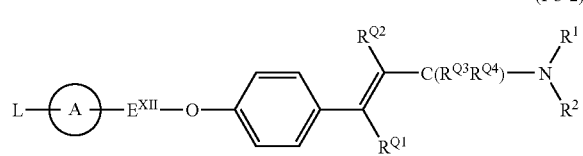

(I-3-2)

wherein $R^{Q1}$, $R^{Q2}$, $R^{Q3}$, and $R^{Q4}$ each have the same meaning as that of $R^5$, benzene ring may have any acceptable number of substituents at any substitutable positions in addition to those described above, the substituent has the same meaning as the "substituent" in the "cyclic group which may have a substituent(s)", and other symbols have the same meanings as described above, a compound represented by formula (I-3-3):

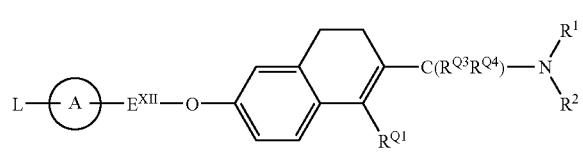

(I-3-3)

wherein 3,4-dihydrobenzene ring may have any acceptable number of substituents at any substitutable positions in addition to those described above, the substituent has the same meaning as the "substituent" in the "cyclic group which may have a substituent(s)", and other symbols have the same meanings as described above, a compound represented by formula (I-3-4):

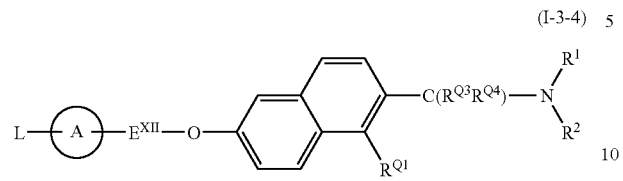
(I-3-4)

wherein naphthalene ring may further have any acceptable number of substituents at any substitutable positions in addition to those described above, the substituent has the same meaning as the "substituent" in the "cyclic group which may have a substituent(s)", and other symbols have the same meanings as described above, a compound represented by formula (I-3-5):

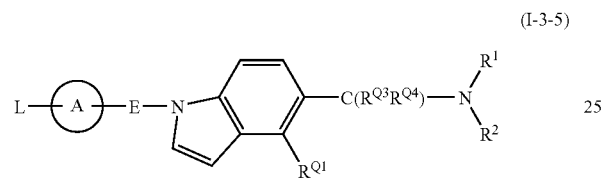
(I-3-5)

wherein indole ring may have any acceptable number of substituents at any substitutable positions in addition to those described above, the substituent has the same meaning as the "substituent" in the "cyclic group which may have a substituent(s)", and other symbols have the same meanings as described above, a compound represented by formula (I-3-6):

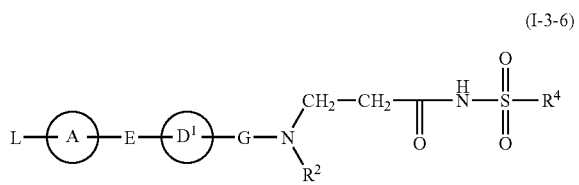
(I-3-6)

wherein all symbols have the same meanings as those described above, a compound represented by formula (I-3-7):

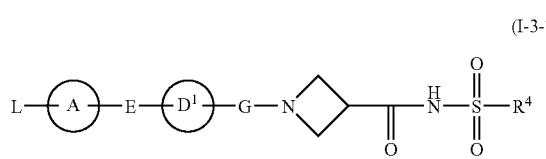
(I-3-7)

wherein all symbols have the same meanings as those described above, a compound represented by formula (I-3-8):

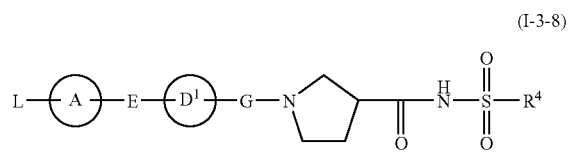
(I-3-8)

wherein all symbols have the same meanings as those described above, a compound represented by formula (I-3-9):

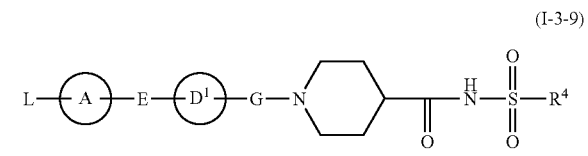
(I-3-9)

wherein all symbols have the same meanings as those described above, and a compound represented by formula (I-3-10):

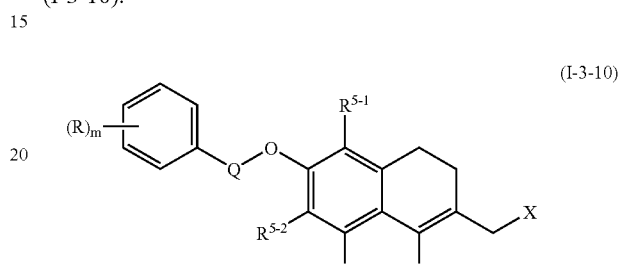
(I-3-10)

wherein all symbols have the same meanings as those described above, a salt thereof, an N-oxide form thereof, a solvate thereof, and a prodrug thereof.

In addition, in the present invention, a compound represented by formula (I) which contains the combinations listed above as preferable groups or preferable rings, a salt thereof, an N-oxide form thereof, a solvate thereof, and a prodrug thereof are all preferable.

Specific embodiments further include the compound of the present invention described in the examples and compounds shown below, a salt thereof, an N-oxide form thereof, a solvate thereof, and a prodrug thereof (1) 1-(4-{3-[5-phenyl-4-(trifluoromethyl)thien-2-yl]-1,2,4-oxadiazol-5-yl}benzyl)piperidine, (2) 1-({6-[3-(4-chlorophenyl)propoxy]-2-naphthyl}methyl)piperidin-4-ol, (3) {1-[(6-{3-[3,5-bis(trifluoromethyl)phenyl]propoxy}-1-methyl-3,4-dihydronaphthalen-2-yl)methyl]piperidin-4-yl}methanol, (4) 1-((2E)-3-{4-[3-(2-chlorophenyl)propoxy]-2-methylphenyl}but-2-enyl)azetidin-3-ol, (5) N,N-dimethyl-2-{6-[(5-phenyl-1,3-thiazol-2-yl)methoxy]-1-naphthyl}ethanamine, (6) 1-(6-{[ethyl(2-hydroxyethyl)amino]methyl}-2-naphthyl)-6-phenylhexan-1-one, (7) 4-[3-(4-oethylphenyl)propyl]morpholine, (8) 8-(2-{3-[(8,8,8-trifluorooctyl)oxy]phenyl}ethyl)-1,4-dioxa-8-azaspiro[4.5]decane, and (9) N-[(5-{[(6-chloroquinolin-2-yl)methyl]sulfonyl}-1-benzothien-2-yl)methyl]-N-ethylethanamine.

The compounds in the present specification were named by using computer program which in general mechanically names in accordance with the regulations of IUPAC, that is ACD/Name (trade name, manufactured by Advanced Chemistry Development Inc.), or named in accordance with IUPAC Nomenclature. For example, the following compound was named N,N-dimethyl-1-{6-[(5-phenylpentyl)oxy]-2-naphthyl}methanamine.

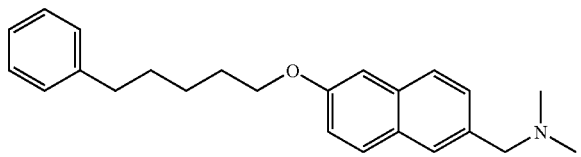

Isomers:

Unless otherwise specifically mentioned, all isomers are included in the present invention. For example, alkyl, alkenyl, alkynyl, alkyloxy, alkoxy, alkenyloxy, alkynyloxy, alkylthio, alkylsulfinyl, alkylsulfonyl, alkylene, alkenylene, alkynylene, acyl, and acyloxy include straight chain and branched ones. Moreover, all of isomers due to double bond, ring, and fused ring (E-, Z—, cis- and trans-forms), isomers due to presence of asymmetric carbon(s) or the like (R—, S-form, α- and β-configuration, enantiomer, and diastereomer), optically active materials having optical rotation (D-, L-, d- and l-forms), polar compound by chromatographic separation (more polar compound and less polar compound), equilibrium compounds, rotamers, a mixture thereof in any proportion, and a racemic mixture are included in the present invention. All tautomers are also included in the present invention.

In the present invention, unless otherwise specified, the symbol ⋯⋯ means the α-configuration substituent, the symbol ╱ means the β-configuration substituent, the symbol ⁓ means α-configuration, β-configuration, or a mixture of α-configuration and β-configuration by an arbitrary ratio, and the symbol ╱ means a mixture of α-configuration and β-configuration by an arbitrary ratio as would be clear to the person skilled in the art.

Salt and Solvate:

The compound of the present invention represented by formula (I) can be converted into a salt by conventionally known methods.

The salts of the compound of the present invention represented by formula (I) include all pharmaceutically acceptable salts. The salts each preferably have low toxicity and water-solubility.

The salt of the compound of the present invention represented by formula (I) includes salts of alkali metal (such as potassium, sodium, and lithium), salts of alkaline earth metal (such as calcium and magnesium), ammonium salts (such as tetramethylammonium salt and tetrabutylammonium salt), salts of organic amine (such as triethylamine, methylamine, dimethylamine, cyclopentylamine, benzylamine, phenethylamine, piperidine, monoethanolamine, diethanolamine, tris(hydroxymethyl)methylamine, lysine, arginine, and N-methyl-D-glucamine), and acid addition salts [such as inorganic acid salts (e.g., hydrochloride, hydrobromide, hydroiodide, sulfate, phosphate, and nitrate), and organic acid salts (e.g., acetate, trifluoroacetate, lactate, tartrate, oxalate, fumarate, maleate, benzoate, citrate, methanesulfonate, ethanesulfonate, benzenesulfonate, toluenesulfonate, isethionate, glucuronate, and gluconate), or the like.

The salts further include a quaternary ammonium salt. The quaternary ammonium salt means the compound represented by formula (I) in which nitrogen atom is quaternized by an $R^0$. $R^0$ represents C1-8 alkyl and C1-8 alkyl which is substituted by phenyl.

Examples of an appropriate solvate of the compound represented by formula (I) include solvates such as hydrate and alcoholate (such as methanolate and ethanolate). The solvates each preferably have low toxicity and water-solubility. In addition, the solvates of the compound of the present invention include solvates of alkali metal salts, alkali earth metal salts, ammonium salts, organic amine salts, and acid addition salts of the above-mentioned compound of the present invention.

The compound represented by formula (I) may be converted into any one of the above-mentioned salts and solvates by a conventionally known method.

Prodrugs:

A prodrug of the compound represented by formula (I), a salt thereof, or a solvate thereof means a compound which is converted to the compound represented by formula (I) by reaction with an enzyme, gastric acid, or the like in the living body. For example, with regard to a prodrug of the compound represented by formula (I), when the compound represented by formula (I) has amino, compounds in which amino is, for example, acylated, alkylated, or phosphorylated (e.g., compounds in which amino of the compound represented by formula (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, acetoxymethylated, or tert-butylated); when the compound represented by formula (I) has hydroxy, compounds where the hydroxy is, for example, acylated, alkylated, phosphorylated, or borated (e.g., compounds in which the hydroxy of the compound represented by formula (I) is acetylated, palmitoylated, propanoylated, pivaloylated, succinylated, fumarylated, alanylated, or dimethylaminomethylcarbonylated); and when the compound represented by formula (I) has carboxy, compounds where carboxy of the compound represented by formula (I) is, for example, esterified or amidated (e.g., compounds in which carboxy of the compound represented by formula (I) is made into ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester, or methylamide). Those compounds may be prepared by a conventionally known method per se. The prodrug of the compound represented by formula (I) may be either a hydrate or a non-hydrate. A prodrug of the compound represented by formula (I) may also be a compound which is converted to the compound represented by formula (I) under physiologic condition as described in "Iyakuhin no kaihatsu, Vol. 7 (Bunshi-sekkei), pp. 163-198 (Hirokawa-Shoten), 1990". Further, the compound represented by formula (I) may also be labeled by a radio isotope (such as $^3H$, $^{14}C$, $^{35}S$, $^{125}I$, etc,).

The compounds of the present invention represented by formula (I), a salt thereof, an N-oxide form thereof, a solvate thereof, or a prodrug thereof (hereinafter, also abbreviated as "the compounds of the present invention") are excellent in solubility and oral absorbability, exhibit a prolonged pharmacological action (e.g., promoting activity of lymphocyte homing and immunosuppressive action of lymphocyte), are hardly affected by drug-metabolic enzymes and have low toxicity. Those characteristics are the most important physical, chemical, and pharmaceutical properties required in developing drugs. Fulfilling those requirements, the compounds of the present invention are likely to be highly excellent drugs (see *The Merck Manual of Diagnosis and Therapy*, 17th Ed., Merck & Co.).

It can be assessed that the compound of the present invention is useful as a drug by methods described in Biological Examples to be described later, and methods obtained by improving those described in Biological Examples. It can be also easily assessed that the compound of the present invention is excellent in terms of a length of serum half-life, a stability in the gastrointestinal tract, an absorption of oral preparations, bioavailability, or the like by conventionally known methods, for example, a method described in Yakubutsu bioavailability (Hyouka to kaizen no kagaku), Jul. 6, 1998, Gendaiiryou-sha, or the like.

Method of the Preparation of the Compound of the Present Invention:

The compound of the present invention represented by formula (I) may be produced by a conventionally known method, for example, a method described in WO 02/092068, Synth. Commun. vol. 33, no. 19, p. 3347 (2003), a method described in *Comprehensive Organic Transformations: A Guide to Functional Group Preparations*, the 2nd edition, methods shown below and/or method in accordance with those, or by using the methods described in the examples, which are subjected to appropriate modifications, in combination. It should be noted that starting materials compound may be used as a salt in the respective production methods described below. For such the salt, the salt above-described as the salt of the compound represented by formula (I) is used.

In addition, as would be clear to the person skilled in the art, when each of a material to be used in the production of the compound of the present invention and intermediate compounds of the compound of the present invention has any one of hydroxy, carboxyl, amino, and mercapto, production of the compound of the present invention of interest may be facilitated, by appropriately subjecting the material or the intermediate compounds to protection/deprotection.

Examples of the protecting group for the hydroxy include methyl, trityl, methoxymethyl (MOM), 1-ethoxyethyl (EE), methoxyethoxymethyl (MEM), 2-tetrahydropyranyl (THP), trimethylsilyl (TMS), triethylsilyl (TES), t-butyldimethylsilyl (TBDMS), t-butyldiphenylsilyl (TBDPS), acetyl (Ac), pivaloyl, benzoyl, benxyl (Bn), p-methoxybenzyl, allyloxycarbonyl (Alloc), and 2,2,2-trichloroethoxycarbonyl (Troc);

Examples of the protecting group for carboxyl include methyl, ethyl, t-butyl, allyl, phenacyl, and benzyl.

Examples of the protecting group for amino include benzyloxycarbonyl, t-butoxycarbonyl, allyloxycarbonyl (Alloc), 1-methyl-1-(4-biphenyl)ethoxycarbonyl (Bpoc), trifluoroacetyl, 9-fluorenylmethoxycarbonyl, benzyl (Bn), p-methoxybenzyl, benzyloxymethyl (BOM), and 2-(trimethylsilyl)ethoxymethyl (SEM).

Examples of the protecting group for mercapto include benzyl, methoxybenzyl, methoxymethyl (MOM), 2-tetrahydropiranyl (THP), diphenylmethyl, and acetyl (Ac).

Protecting groups for each of hydroxy, carboxyl, amino, and mercapto are not particularly limited to the above-mentioned protecting groups as long as the groups can be easily and selectively left. For example, the protecting groups described in *Protective Groups in Organic Synthesis* (T. W. Greene, John Wiley & Sons Inc, 1999) may be used.

The deprotection of protecting groups for each of hydroxy, carboxyl, amino, or mercapto is widely known, and examples thereof include:

(1) deprotection by alkali hydrolysis;
(2) deprotection under acidic conditions;
(3) deprotection by hydrogenolysis;
(4) deprotection using a metal complex;
(5) deprotection using a metal; and
(6) deprotection of silyl.

Those methods will be described in detail.

The deprotection by alkali hydrolysis (1) (for example, deprotection of trifluoroacetyl) is performed in an organic solvent (such as methanol, tetrahydrofuran, or 1,4-dioxane) at temperature of 0 to 40° C. by using, for example, hydroxides of alkali metals (such as sodium hydroxide, potassium hydroxide, and lithium hydroxide), hydroxides of alkali earth metals (such as barium hydroxide and calcium hydroxide), carbonates (such as sodium carbonate and potassium carbonate), solutions thereof, or mixtures thereof.

The deprotection under acidic conditions (2) (for example, deprotection of t-butoxycarbonyl or trityl) is performed in, for example, water or an organic solvent (such as dichloromethane, chloroform, 1,4-dioxane, ethyl acetate, or anisol), an organic acid (such as acetic acid, trifluoroacetic acid, or methanesulfonic acid), an inorganic acid (such as hydrochloric acid or sulfuric acid), or mixtures thereof (such as hydrogen bromide/acetic acid), at temperature of 0 to 100° C.

The deprotection by hydrogenolysis (3) (for example, deprotection of benzyl, benzhydryl, benzyloxycarbonyl, or allyloxycarbonyl) is performed in, for example, a solvent (for example, ethers (such as tetrahydrofuran, 1,4-dioxane, dimethoxyethane, or diethyl ether), alcohols (such as methanol or ethanol), benzenes (such as benzene or toluene), ketones (such as acetone or methyl ethyl ketone), nitriles (such as acetonitrile), amides (such as N,N-dimethylformamide), water, ethyl acetate, acetic acid, or a mixture solvent of two or more of them), in the presence of a catalyst (such as palladium-carbon, palladium black, palladium hydroxide, platinum oxide, or Raney nickel), under hydrogen atmosphere under atmospheric pressure or under pressure or in the presence of ammonium formate at temperature of 0 to 200° C.

The deprotection using a metal complex (4) (for example, deprotection of allyloxycarbonyl) is performed in, for example, an organic solvent (such as dichloromethane, N,N-dimethylformamide, tetrahydrofuran, ethyl acetate, acetonitorile, 1,4-dioxane, or ethanol), water, or a mixture solvent thereof, in the presence of a trap agent (such as tributyltin hydride, triethylsilane, dimedone, morpholine, diethylamine, or pyrrolidine), an organic acid (such as acetic acid, formic acid, or 2-ethylhexanoic acid), and/or an organic acid salt (such as sodium 2-ethylhexanoate or potassium 2-ethylhexanoate), in the presence or absence of phosphines (such as triphenylphosphine), by using a metal complex (such as tetrakis(tirphenylphosphine)palladium (0), dichlorobis(tirphenylphosphine)palladium (II), palladium acetate (II), or tris(triphenylphosphine)rhodium (I) chloride), at temperature of 0 to 40° C.

The deprotection using a metal (5) is performed in, for example, an acidic solvent (acetic acid, buffer solution having pH of 4.2 to 7.2, or a mixture of those solutions and an organic solvent such as tetrahydrofuran), in the presence of powder zinc, while applying ultrasonic waves if necessary, at temperature of 0 to 40° C.

The deprotection of silyl (6) is performed in, for example, an organic solvent miscible with water (such as tetrahydrofuran or acetonitrile), by using tetrabutylammonium fluoride, at temperature of 0 to 40° C.

[1] Among the compounds of the present invention represented by formula (I), a compound in which G is -G$^H$-CH$_2$— (in which G$^H$ has the same meaning as G, and the number of the atoms in its main chain of which is one smaller than that of G) and X is amino which may have a substituent(s), that is, a compound represented by formula (I-A):

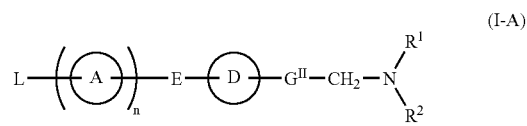

(I-A)

wherein all symbols have the same meanings as described above, can be produced by subjecting an aldehyde compound represented by formula (II):

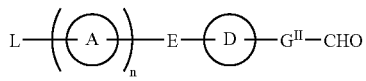

(II)

wherein all symbols have the same meanings as described above, and an amine compound represented by formula (III):

(III)

wherein all symbols have the same meanings as described below, to reductive amination, or by subjecting the amine compound represented by formula (OTf) and a compound represented by formula (IV):

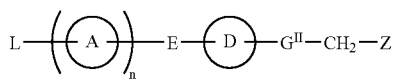

(IV)

wherein Z represents a leaving group such as a halogen atom, methanesulfonyloxy (OMs), p-toluenesulfonyloxy (OTs), trifluoromethanesulfonyloxy (OTf), alkylthio, alkylsulfinyl, alkylsulfonyl, or hydroxysulfonyl, and other symbols have the same meanings as described above, to alkylation.

The reductive amination between an aldehyde compound represented by formula (II) and an amine compound represented by formula (III) is well-known. The reductive amination is performed, for example, by reacting them in an inert organic solvent (any one of dichloroethane, dichloromethane, and N,N-dimethylformamide, or a mixture solvent composed of two or more of them at an arbitrary ratio), in the presence or absence of an organic acid (such as acetic acid), or in the presence or absence of an organic base (such as triethylamine or sodium hydrogen carbonate), in the presence or absence of a dehydrating agent (such as sodium sulfate, molecular sieves, or trimethoxymethane), by using a reducing agent (such as triacetoxy sodium borohydride, cyano sodium borohydride, or tetrabutylammonium borohydride), at temperature of 0 to 100° C.

Further, if necessary, the above-mentioned deprotection may be performed after the reaction. Still further, if necessary, an operation for converting the resultant into a non-toxic salt of interest may be performed by any conventionally known method after the reaction.

The alkylation between an amine compound represented by formula (III) and a compound represented by formula (IV) is well-known. The alkylation is performed, for example, by reacting an amine compound in an organic solvent (for example, aromatic hydrocarbons such as benzene, toluene, and xylene, halogenated hydrocarbons such as dichloromethane and chloroform, saturated hydrocarbons such as hexane, heptane, and cyclohexane, ethers such as diethyl ether, tetrahydrofuran, and 1,4-dioxane, ketones such as acetone and methyl ethyl ketone, nitoriles such as acetonitorile, sulfoxides such as dimethylsulfoxide, acid amides such as N,N-dimethylformamide, or esters such as ethyl acetate is used. Any one of those solvents may be used alone or, if necessary, two or more kinds of them may be mixed in an appropriate ratio such as 1:1 to 1:10 for use), in the presence or absence of base (for example, alkali metal hydrides or alkali earth metal hydrides such as sodium hydride and potassium hydride, alkyl lithiums such as butyllithium, sec-butyllithium and t-butyllithium, alkoxides of alkali metal such as sodium methoxide and sodium ethoxide, inorganic bases of alkali metal or the like such as metallic sodium and metallic potassium, alkylamines such as triethylamine, tributylamine, and diisopropylethylamine, aromatic amines such as N,N-dimethylaniline, pyridine, lutidine, collidine, and 4-(dimethylamino)pyridine, organic bases such as DBU (1,8-diazabicyclo[5.4.0]undecene-7), or metal amides such as lithium diisopropylamide, lithium hexamethyldisilazide, potassium hexamethyldisilazide, and sodium hexamethyldisilazide), at temperature of −78 to 100° C.

Further, if necessary, the above-mentioned deprotection may be performed after the reaction. Furthermore, if necessary, an operation for converting the resultant into a non-toxic salt of interest may be performed by any conventionally known method after the reaction.

[2] Among the compounds of the present invention represented by formula (I), a compound in which G is -$G^{II}$-CO— (in which $G^{II}$ has the same meaning as described above) and X is amino which may have a substituent(s), that is, a compound represented by formula (I-B):

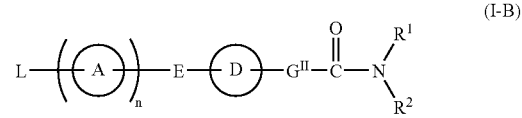

(I-B)

wherein all symbols have the same meanings as described above; can be produced by subjecting a carboxylic acid compound represented by formula (V):

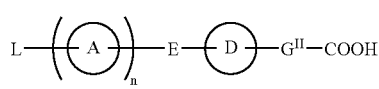

(V)

wherein all symbols have the same meanings as described above; and an amine compound represented by formula (III) to amidation. The amidation is well-known, and examples thereof include the following methods:
(1) method using an acid halide;
(2) method using a mixed acid anhydride; and
(3) method using a condensation agent.
These methods will be described in detail.

The method using an acid halide (1) is performed by, for example, reacting a carboxylic acid compound with an acid halide agent (such as oxalyl chloride, thionyl chloride, phosphorus hexachloride, or phosphorus trichloride), in an organic solvent (for example, halogenated hydrocarbons such as chloroform and dichloromethane, ethers such as diethyl ether, tetrahydrofuran, and 1,4-dioxane, or acid amides such as N,N-dimethylformamid is used; any one of those solvents may be used alone or, if necessary, two or more kinds of them may be mixed in an appropriate ratio such as 1:1 to 1:10 for use), or without solvent, at the temperature of −20° C. to reflux temperature, and then by reacting the resultant acid halide with an amine compound, in the presence of a base (for example, alkylamines such as triethylamine, tributylamine, and diisopropylethylamine, or aromatic amines such as N,N-dimethylaniline, pyridine, and 4-(dimethylamino)pyridine), at temperature of 0 to 40° C. Alternatively, the method may be performed by reacting the resultant acid halide with an amine compound, in an organic solvent (for example, diethyl ether, 1,4-dioxane, or tetrahydrofuran is used; any one of those solvents may be used alone or, if necessary, two or more kinds of them may be mixed in an appropriate ratio such as 1:1 to 1:10 for use), by using an aqueous solution of alkali solution (such as sodium hydrogen carbonate or a sodium hydroxide), at temperature of 0 to 40° C.

The method using a mixed acid anhydride (2) is performed by, for example, reacting a carboxylic acid compound with an acid halide agent (such as pivaloyl chloride, p-toluenesulfonyl chloride, or methanesulfonyl chloride) or with an acid derivative (such as ethyl chloroformate or isobutyl chlorformate), in an organic solvent (for example, halogenated hydrocarbons such as chloroform and dichloromethane, ethers such as diethyl ether, tetrahydrofuran, and 1,4-dioxane, or acid amides such as N,N-dimethylformamide is used; any one of those solvents may be used alone or, if necessary, two or more kinds of them may be mixed in an appropriate ratio such as 1:1 to 1:10 for use), or without solvent, in the presence of a base (for example, pyridine, triethylamine, dimethylaniline, N,N-dimethylaminopyridine, and diisopropylethylamine) at temperature of 0 to 40° C., and then by reacting the resultant mixed acid anhydride with an amine compound, in an organic solvent (for example, halogenated hydrocarbons such as chloroform and dichloromethane, ethers such as diethyl ether, tetrahydrofuran, and 1,4-dioxane, or acid amides such as N,N-dimethylformamide is used; any one of those solvents may be used alone or, if necessary, two or more kinds of them may be mixed in an appropriate ratio such as 1:1 to 1:10 for use), at temperature of 0 to 40° C.

The method using a condensation agent (3) is performed by, for example, reacting a carboxylic acid compound with an amine compound, in an organic solvent (for example, halogenated hydrocarbons such as chloroform and dichloromethane, ethers such as diethyl ether, tetrahydrofuran, and 1,4-dioxane, or acid amides such as N,N-dimethylformamides is used; any one of those solvents may be used alone or, if necessary, two or more kinds of them may be mixed in an appropriate ratio such as 1:1 to 1:10 for use), or without solvent, in the presence of absence of a base (for example, alkylamines such as triethylamine, tributylamine, and diisopropylethylamine, or aromatic amines such as N,N-dimethylaniline, pyridine, and 4-(dimethylamino)pyridine), by using a condensation agent (for example, 1,3-dicyclohexylcarbodiimide (DCC), 1-ethyl-3-[3-(dimethylamino)propyl]carbodiimide (EDC), 1,1'-carbonyldiimidazole (CDI), 2-chloro-1-methylpyridinum iodine, 1-propanephosphonic acid cyclic anhydride (PPA)), by using or without using 1-hydroxybenztriazole (HOBt), at temperature of 0 to 40° C.

Each of the methods (1) to (3) is desirably performed under an inert gas (such as argon or nitrogen) atmosphere and under anhydrous conditions.

Further, if necessary, the above-mentioned deprotection may be performed after the reaction. Furthermore, if necessary, an operation for converting the resultant into a non-toxic salt of interest may be performed by any conventionally known method after the reaction.

[3] Among the compounds of the present invention represented by formula (I), a compound in which X represents the following.

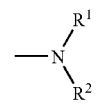

wherein all symbols have the same meanings as described above; and $R^1$ represents the following:

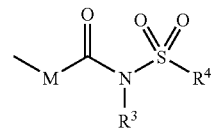

wherein all symbols have the same meanings as described above; that is, a compound represented by formula (I-C):

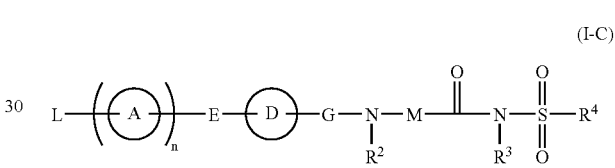

(I-C)

wherein all symbols have the same meanings as described above; can be produced by subjecting a carboxylic acid compound represented by formula (VI):

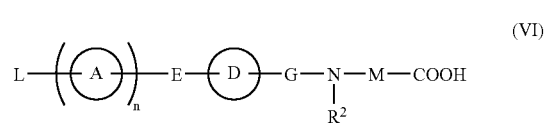

(VI)

wherein all symbols have the same meanings as described above; and a compound represented by formula (VII):

(VII)

wherein all symbols have the same meanings as described above; to amidation. The amidation can be performed in accordance with the method by which the above-mentioned carboxylic acid compound represented by formula (V) and amine compound represented by formula (III) are subjected to amidation.

Further, if necessary, the above-mentioned deprotection may be performed after the reaction. Furthermore, if necessary, an operation for converting the resultant into a non-toxic salt of interest may be performed by any conventionally known method after the reaction.

[4] Among the compounds of the present invention represented by formula (I), a compound in which X represents the following:

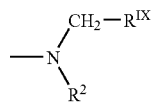

wherein $R^{IX}$—$CH_2$— represents the substituent which binds to its main chain via a nitrogen atom and methylene among the substituents represented by $R^1$, and other symbols have the same meanings as described above; that is, a compound represented by formula (I-D):

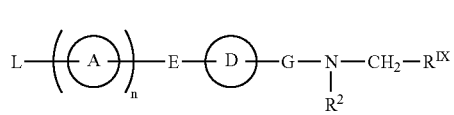
(I-D)

wherein all symbols have the same meanings as described above; can be produced by subjecting an amine compound represented by formula (VIII):

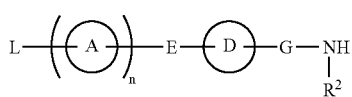
(VIII)

wherein all symbols have the same meanings as described above; and an aldehyde compound represented by formula (IX):

$$OHC—R^{IX} \quad (IX)$$

wherein all symbols have the same meanings as described above; to reductive amination. The reductive amination can be performed in accordance with the method by which the above-mentioned aldehyde compound represented by formula (II) and amine compound represented by formula (III) are subjected to reductive amination.

Further, if necessary, the above-mentioned deprotection may be performed after the reaction. Furthermore, if necessary, an operation for converting the resultant into a non-toxic salt of interest may be performed by any conventionally known method after the reaction.

[5] Among the compounds of the present invention represented by formula (I), a compound in which X represents a "heterocyclic group which contains at least one nitrogen atom and which may have a substituent(s)", and of which substituent is represented by the following:

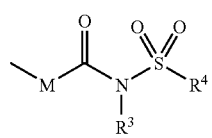

wherein all symbols have the same meanings as described above; that is, a compound represented by formula (I-E):

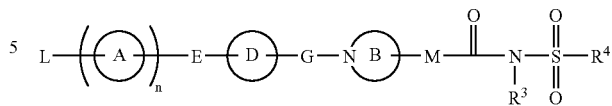
(I-E)

wherein ring B represents a "heterocyclic group containing at least one nitrogen atom" and other symbols have the same meanings as described above; can be produced by subjecting a carboxylic acid compound represented by formula (XI):

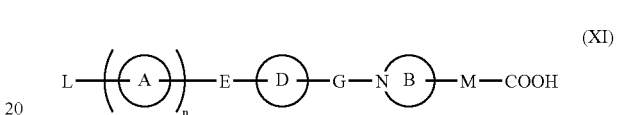
(XI)

wherein all symbols have the same meanings as described above; and a sulfonamide compound represented by formula (VII) to amidation. The amidation can be performed in accordance with the method by which the above-mentioned carboxylic acid compound represented by formula (V) and amine compound represented by formula (III) are subjected to amidation.

Further, if necessary, the above-mentioned deprotection may be performed after the reaction. Furthermore, if necessary, an operation for converting the resultant into a non-toxic salt of interest may be performed by any conventionally known method after the reaction.

In the present invention, among the compounds used as starting materials represented by formulae (II), (IV), (V), (VI), (VIII), and (XI), respectively, a compound in which E binds to ring D via oxygen, that is, a compound represented by formula (XII):

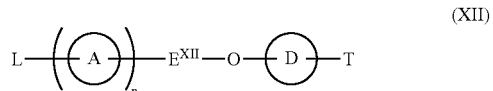
(XII)

wherein $E^{XII}$ has the same meaning as E, and the number of the atoms in its main chain of which is one smaller than that of E, T represents any one of -$G^{II}$-CHO, -$G^{II}$-$CH_2$—Z, -$G^{II}$-COOH, -G-N($R^2$)-M-COOH, -G-NH—$R^2$, and the following:

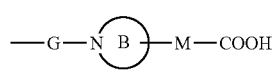

wherein all symbols have the same meanings as described above; and other symbols have the same meanings as described above; can be produced by the following method (1) or (2).

(1) A compound represented by formula (XII) can be produced by subjecting a compound represented by formula (XIII):

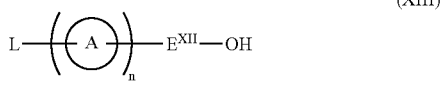

(XIII)

wherein all symbols have the same meanings as described above; and a compound represented by formula (XIV):

(XIV)

wherein all symbols have the same meanings as described above; to Mitsunobu reaction, and then deprotecting a protecting group if necessary. The Mitsunobu reaction is well-known, and performed, for example, in an organic solvent (such as dichlormethane, dimethylether, tetrahydrofuran, acetonitrile, benzene, or toluene), in the presence of an azo compound (such as diethyl azodicarboxylate (DEAD), diisopropyl azodicarboxylate, 1,1'-(azodicarbonyl)dipiperidine, or 1,1'-azobis(N,N-dimethylformamide)) and a phosphine compound (such as triphenylphosphine, tributylphosphine, trimethylphosphine, or polymer-supported triphenylphosphine), at temperature of 0 to 60° C.

(2) A compound represented by formula (MI) can be produced by subjecting any one of the combinations: a combination of a compound represented by formula (XIII) and a compound represented by formula (XV):

(XV)

wherein all symbols have the same meanings as described above; and a combination of a compound represented by formula (XVI):

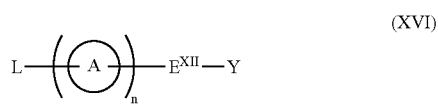

(XVI)

wherein all symbols have the same meanings as described above; and a compound represented by formula (XIV) to etherification, and then deprotecting a protecting group if necessary.

The etherification is well-known, and performed, for example, in an organic solvent (such as N,N-dimethylformamide, dimethylsulfoxide, chloroform, dichlormethane, diethyl ether, tetrahydrofuran, or methyl t-butyl ether), in the presence of an alkali metal hydroxide (such as sodium hydroxide, potassium hydroxide, or lithium hydroxide), an alkali earth metal hydroxide (such as barium hydroxide or calcium hydroxide), a carbonate (such as sodium carbonate, potassium carbonate, or cesium carbonate), aqueous solutions thereof, or mixtures thereof, at temperature of 0 to 100° C.

In the present invention, compounds other than compounds which are used as starting materials and represented by formulae (II) to (IX), and (XI) to (XVI), are conventionally known per se, or can be produced by any conventionally known method such as a method described in WO 02/092068, a method described in *Comprehensive Organic Transformations: A Guide to Functional Group Preparations*, the 2nd edition (written by Richard C. Larock, John Wiley & Sons Inc, 1999), and/or methods in accordance with those methods, or by using the methods described in the examples, which are subjected to appropriate modifications, in combination.

In each reaction of the present specification, a solid phase reagent which is supported by polymer (for example, polystyrene, polyacrylamide, polypropylene or polyethyleneglycol) may be used.

In each reaction of the present specification, the obtained products may be purified by conventional purification techniques. For example, the purification may be carried out by distillation under atmospheric or reduced pressure, by high performance liquid chromatography by using silica gel or magnesium silicate, by thin layer chromatography, by ion-exchange resin, by scavenger resin, by column chromatography, by washing or by recrystallization. The purification may be done at each reaction or after several reactions.

Toxicity:

The compounds of the present invention have sufficiently low toxicities and, therefore, they are considered to be sufficiently safe when used as drugs.

Application to pharmaceuticals:

The compound of the present invention is a compound capable of binding S1P receptor (in particular, EDG-1 and/or EDG-6). Accordingly, the compound is useful as a preventing and/or treating agent for mammals (for example, human, or non-human animals such as simian, ovine, bovine, equine, canine, feline, leporine, rat, and mouse), for: rejection in transplantation; rejection of a transplanted organ; graft versus host disease; an autoimmune disease (e.g., systemic lupus erythematosus, rheumatoid arthritis, multiple sclerosis, psoriasis, ulcerative colitis, Crohn's disease, myasthenia gravis, autoimmune diabetes, and the like); an allergic disease (e.g., atopic dermatitis, pollen disease, food allergy, and the like); asthma; infectious disease; ulcer; lymphoma; malignant tumor (e.g., cancer and the like); leukemia; and a disease associated with lymphocyte infiltration into a tissue; a peripheral arterial disease including arteriosclerosis obliterans, thromboangiitis obliterans, Buerger's disease, and diabetic neuropathy; varicose vein such as hemorrhoid, anal fissure, or anal fistula; dissecting aneurysm of the aorta; sepsis; an inflammatory disease such as angiitis, nephritis, or pneumonia; various edematous disease involved in ischemia of various organs and increase of the blood permeability, for example, cerebral stroke, ischemia-reperfusion injury, cerebral infarction, myocardial infarction, angina, congestive heart failure, pleuritis, DIC, or multiple organ failure; bedsore; burn; trauma injury; inflammatory bowel disease; genetic disease; osteoporosis; arteriosclerosis; fibrosis such as pulmonary fibrosis or liver fibrosis; interstitial pneumotitis; chronic hepatitis; liver cirrhosis; chronic renal insufficiency; renal glomerular sclerosis; diabetes; and the like. In addition, the compound of the present invention is useful as a preoperative, postoperative, and/or prognostic activator for blood vessel accompanying transplantation of various organs, tissues, and/or cells, for example, as an adhesion activator of transplanted organs such as heart transplantation, renal transplantation, dermal transplantation, or liver transplantation. In addition, the compound of the present invention is useful, not only in vivo but also in vitro, as an adjusting agent such as a differentiation activator of cells or the like.

Further, the compound of the present invention can be used for mammals (for example, human, or non-human animals such as simian, ovine, bovine, equine, canine, feline, leporine, rat, and mouse), as a glucose metabolism-improving agent, a glucose tolerance-improving agent, an insulin secretion-promoting agent, and/or a pancreatic cell-protecting agent, thus can be used as an agent for prevention and/or treatment of diabetes. Diabetes may be type I diabetes, type II diabetes, or other type diabetes, in particular, type II diabetes is preferable.

When the compound of the present invention or a combination preparation of the compound of the present invention and other drug(s) is used for the above-described purpose, it is normally administered systemically or locally, by oral or parenteral administration. The doses to be administered are determined depending upon, for example, age, body weight, symptom, the desired therapeutic effect, the route of administration, and the duration of the treatment. In the human adult, the doses per person are generally from 1 ng to 100 mg, by oral administration, from once up to several times per day, from 0.1 ng to 10 mg, by parenteral administration, from once up to several times per day, or continuous infusion for 1 to 24 hours per day from vein. As described above, the doses to be administered depend upon various conditions. Therefore, there are cases in which doses lower than or greater than the above-described ranges are required to be administered.

When the compound of the present invention or a combination preparation of the compound of the present invention and other drug(s) is administered, it is used in the form of solid for oral administration, liquid forms for oral administration, injections, liniments, suppositories, eye drops, inhalant, or the like for parenteral administration.

Solid forms for oral administration include tablets, pills, capsules, powder medicine, and granules. Capsules include hard capsules and soft capsules. Tablets include sublingual tablets, buccal adhesive tablets, oral rapid disintegrating tablets, and the like. Also, in such the solid forms for oral administration, one or more active material(s) may be directly used or be admixed with a vehicle (such as lactose, mannitol, glucose, microcrystalline cellulose, or starch), a binder (such as hydroxypropylcellulose, polyvinylpyrrolidone, or magnesium metasilicate aluminate), a disintegrant (such as cellulose calcium glycolate), lubricants (such as magnesium stearate), a stabilizing agent, and a solubilizing agent (such as glutamic acid or aspartic acid) and prepared according to well-known methods. The solid forms may, if necessary, be coated with a coating agent (such as sucrose, gelatin, hydroxypropylcellulose, or hydroxypropylmethylcellulose phthalate), or be coated with two or more layers. Furthermore, coating may include capsules made of absorbable materials such as gelatin.

The sublingual tablets are produced in accordance with a conventionally known method. For example, one or more active substance(s) are used after being made into pharmaceutical preparations according to well-known methods by mixing with an vehicle (such as lactose, mannitol, glucose, microcrystalline cellulose, colloidal silica, or starch), a binder (such as hydroxypropylcellulose, polyvinylpyrrolidone, or magnesium aluminometasilicate), a disintegrant (such as starch, L-hydroxypropylcellulose, carboxymethylcellulose, croscarmellose sodium, or cellulose calcium glycolate), a lubricant (such as magnesium stearate), a swelling agent (such as hydroxypropylcellulose, hydroxypropylmethylcellulose, carbopol, carboxymethylcellulose, polyvinyl alcohol, xanthan gum, or guar gum), a swelling adjuvant (such as glucose, fructose, mannitol, xylitol, erythritol, maltose, trehalose, phosphate, citrate, silicate, glycine, glutamic acid, or arginine), a stabilizing agent, a solubilizing agent (such as polyethylene glycol, propylene glycol, glutamic acid, or aspartic acid), a flavoring agent (such as orange, strawberry, mint, lemon, or vanilla), and the like. Also, if necessary, they may be coated with a coating agent (such as sucrose, gelatin, hydroxypropylcellulose, or hydroxypropylmethylcellulose phthalate), or coated with two or more layers. In addition, if necessary, additive agents generally used such as an antispetic, an antioxidant, a colorant, and a sweetening agent can also be added thereto. The buccal adhesive tablets are produced or prepared in accordance with a conventionally known method. For example, one or more active substance(s) are used after being made into pharmaceutical preparations according to well-known methods by mixing with an vehicle (such as lactose, mannitol, glucose, microcrystalline cellulose, colloidal silica, or starch), a binder (such as hydroxypropylcellulose, polyvinylpyrrolidone, or magnesium aluminometasilicate), a disintegrant (such as starch, L-hydroxypropylcellulose, carboxymethylcellulose, croscarmellose sodium, or cellulose calcium glycolate), a lubricant (such as magnesium stearate), a adhesion agent (such as hydroxypropylcellulose, hydroxypropylmethylcellulose, carbopol, carboxymethylcellulose, polyvinyl alcohol, xanthan gum, or guar gum), a adhesion adjuvant (such as glucose, fructose, mannitol, xylitol, erythritol, maltose, trehalose, phosphate, citrate, silicate, glycine, glutamic acid, or arginine), a stabilizing agent, a solubilizing agent (such as polyethylene glycol, propylene glycol, glutamic acid, or aspartic acid), a flavoring agent (such as orange, strawberry, mint, lemon, or vanilla) and the like. Also, if necessary, they may be coated with a coating agent (such as sucrose, gelatin, hydroxypropylcellulose, or hydroxypropylmethylcellulose phthalate), or coated with two or more layers. In addition, if necessary, additive agents generally used such as an antispetic, an antioxidant, a colorant, and a sweetening agent can also be added thereto.

The oral rapid disintegrating tablets are produced in accordance with a conventionally known method. For example, one or more active substance(s) are used as such or after being made into pharmaceutical preparations according to well-known methods by mixing the active substances, prepared by coating the material powder or granulated material particles with an appropriate coating agent (such as ethyl cellulose, hydroxypropylcellulose, hydroxypropylmethylcellulose, or acrylate-methacrylate copolymer) and a plasticizer (such as polyethylene glycol, or triethyl citrate), with an vehicle (such as lactose, mannitol, glucose, microcrystalline cellulose, colloidal silica, or starch), a binder (such as hydroxypropylcellulose, polyvinylpyrrolidone, or magnesium aluminometasilicate), a disintegrant (such as starch, L-hydroxypropylcellulose, carboxymethylcellulose, croscarmellose sodium, or cellulose calcium glycolate), a lubricant (such as magnesium stearate), a dispersing adjuvant (such as glucose, fructose, mannitol, xylitol, erythritol, maltose, trehalose, phosphate, citrate, silicate, glycine, glutamic acid, or arginine), a stabilizing agent, a solubilizing agent (such as polyethylene glycol, propylene glycol, glutamic acid, or aspartic acid), a flavoring agent (such as orange, strawberry, mint, lemon, or vanilla) and the like. Also, if necessary, they may be coated with a coating agent (such as sucrose, gelatin, hydroxypropylcellulose, or hydroxypropylmethylcellulose phthalate), or coated with two or more layers. In addition, if necessary, additive agents generally used such as a preservative, an antioxidant, a colorant, and a sweetening agent can also be added thereto.

Liquid forms for oral administration include pharmaceutically acceptable solutions, suspensions, emulsions, syrups, and elixirs. In the liquid forms, one or more active material(s) may be dissolved, suspended, or emulized into diluent(s) commonly used in the art (such as purified water, ethanol, or a mixture thereof). Further, the liquid forms may also include wetting agents, suspending agents, emulsifying agents, sweetening agents, flavoring agents, aromatic agent, preservative, or buffering agent.

The agent for parenteral administration may be in the form of, e.g., an ointment, a gel, a cream, a wet compress, a paste, a liniment, a nebula, an inhalant, a spray, eye drops, a collunarium, or the like. These agents each contain one or more active materials and are prepared by conventionally known methods or commonly used formulations.

The ointment is prepared by known or commonly used formulations. For example, one or more active materials are titurated or dissolved in a base to prepare such the ointment. The ointment base is selected from known or commonly used materials. For example, higher aliphatic acid or higher aliphatic acid ester (e.g., myristic acid, palmitic acid, stearic acid, oleic acid, myristic acid ester, palmitic acid ester, stearic acid ester, and oleic acid ester), wax (e.g., beeswax, whale wax, and ceresin), surface active agent (e.g., polyoxyethylene alkyl ether phosphoric acid ester), higher alcohol (e.g., cetanol, stearyl alcohol, and setostearyl alcohol), silicon oil (e.g., dimethyl polysiloxane), hydrocarbons (e.g., hydrophilic petrolatum, white petrolatum, purified lanolin, and liquid paraffin), glycols (e.g., ethylene glycol, diethylene glycol, propylene glycol, polyethylene glycol, and macrogol), vegetable oil (e.g., castor oil, olive oil, sesame oil, and turpentine oil), animal oil (e.g., mink oil, yolk oil, squalane oil, and squalene oil), water, absorption accelerator, or rash preventive may be used alone or in combination of two or more thereof. The base may further include a humectant, a preservative, a stabilizer, an antioxidant, a perfume, or the like.

The gel is prepared by known or commonly used formulations. For example, one or more active materials are dissolved in a base to prepare such the gel. The gel base is selected from known or commonly used materials. For example, lower alcohol (e.g., ethanol, isopropyl alcohol), a gelling agent (e.g., carboxymethylcellulose, hydroxyethylcellulose, hydroxypropylcellulose, and ethylcellulose), a neutralizing agent (e.g., triethanolamine, and diisopropanolamine), a surface active agent (e.g., polyethylene glycol monostearate), a gum, water, an absorption accelerator, or a rash preventive may be used alone or in combination of two or more thereof. The gel base may further include a preservative, an antioxidant, a perfume, or the like.

The cream is prepared by known or commonly used formulations. For example, one or more active materials are dissolved or emulsified in a base to produce or prepare such the cream. The cream base is selected from known or commonly used materials. For example, higher aliphatic acid ester, lower alcohol, hydrocarbons, polyvalent alcohol (e.g., propylene glycol, and 1,3-butylene glycol), higher alcohol (e.g., 2-hexyldecanol, and cetanol), an emulsifier (e.g., polyoxyethylene alkyl ether, and aliphatic acid ester), water, an absorption accelerator, or a rash preventive may be used alone or in combination of two or more thereof. The cream base may further include a preservative, an antioxidant, a perfume, or the like.

The wet compress is prepared by known or commonly used formulations. For example, one or more active materials are dissolved in a base and then a kneaded mixture is spread and applied on a support to prepare such the wet compress. The wet compress base is selected from known or commonly used materials. For example, a thickening agent (e.g., polyacrylic acid, polyvinyl pyrrolidone, gum arabic, starch, gelatin, and methylcellulose), a wetting agent (e.g., urea, glycerin, and propylene glycol), a filler (e.g., kaolin, zinc oxide, talc, calcium, and magnesium), water, a solubilizing agent, a tackifier, and a rash preventive may be used alone or in combination of two or more thereof. The wet compress base may further include a preservative, an antioxidant, a perfume, or the like.

The pasting agent is prepared by known or commonly used formulations. For example, one or more active materials are dissolved in a base and then prepared kneaded mixture is spread and applied on a support to prepare such the pasting agent. The pasting agent base is selected from known or commonly used materials. For example, polymer base, fat and oil, higher aliphatic acid, a tackifier, or a rash preventive may be used alone or in combination of two or more thereof. The pasting agent base may further include a preservative, an antioxidant, a perfume, or the like.

The liniment is prepared by known or commonly used formulations. For example, one or more active materials are dissolved, suspended or emulsified in one or combination of two or more selected from water, alcohol (e.g., ethanol and polyethylene glycol), higher aliphatic acid, glycerin, soap, an emulsifier, a suspending agent, and the like, to prepare such the liniment. The liniment may further include a preservative, an antioxidant, a perfume, or the like.

The nebula, inhalant, and spray each may include a stabilizer such as sodium hydrogensulfite and a buffer capable of providing isotonicity such as an isotonic agent (e.g., sodium chloride, sodium citrate, and citric acid). An aerosol may also be used.

The injection for parenteral administration may be in the form of solution, suspension, emulsion, or solid injection to be dissolved or suspended in a solvent in use. The injection is prepared by dissolving, suspending, or emulsifying one or more active materials in a solvent. As such the solvent, there may be used distilled water for injection, saline, vegetable oil, alcohols such as propylene glycol, polyethylene glycol, and ethanol, or the like, and the combination thereof. The injection may further include a stabilizer, a solubilizing agent (e.g., glutamic acid, aspartic acid, Polysolvate 80 (trade name)), a suspending agent, an emulsifier, a soothing agent, a buffer, an antispetic, or the like. The injection is sterilized at the final step or prepared by an aseptic process. Alternatively, an aseptic solid agent such as freeze-dried product may be used by being rendered aseptic or dissolved in an aseptic distilled water for injection or other solvent before use.

The eye drops for parenteral administration may be in the form of liquid, suspension, emulsion or ointment, or may be dissolved in a solvent in use. These eye drops are prepared by conventionally known methods. For example, one or more active materials are dissolved, suspended or emulsified in a solvent. As such the solvent for eye drops, there may be used sterilized purified water, saline, and other aqueous or non-aqueous solvents for injection (e.g., vegetable oil), and the combination thereof. The eye drops may include an isotonic agent (e.g., sodium chloride and concentrated glycerin), a buffering agent (e.g., sodium phosphate and sodium acetate), a surface active agent (e.g., Polysolvate 80 (trade name), polyoxyl stearate 40, polyoxyethylene-hardened castor oil), a stabilizer (e.g., sodium citrate and sodium edetate), an antispetic (e.g., benzalconium chloride and Paraben), or the like to be properly selected as necessary. The eye drops are sterilized or prepared by an aseptic process in the final step. Alternatively, an aseptic solid agent such as freeze-dried product may be used by being rendered aseptic or dissolved in an aseptic distilled water for injection or other solvent before use.

The inhalant for parenteral administration may be in the form of aerosol, powder for inhalation, or liquid for inhalation. The liquid for inhalation may be dissolved or suspended in water or other proper medium in use. These inhalants are prepared by a conventionally known method. For example, the liquid for inhalation is prepared from materials properly selected from antispetics (e.g., benzalconium chloride and Paraben), colorants, buffering agents (e.g., sodium phosphate and sodium acetate), isotonic agents (e.g., sodium chloride and concentrated glycerin), thickening agents (e.g., carboxyvinyl polymer), absorption accelerators, and the like if necessary.

The powder for inhalation is prepared from materials properly selected from lubricants (e.g., stearic acid and salts thereof), binders (e.g., starch and dextrin), vehicles (e.g., lactose and cellulose), colorants, antispetics (e.g., benzalconium chloride and Paraben), absorption accelerators, or the like, if necessary.

In order to administer the liquid for inhalation, a sprayer (e.g., atomizer and nebulizer) is normally used. In order to administer the powder for inhalation, a powder inhaler is normally used.

Other examples of the composition for oral administration include suppository for rectal administration and pessary for vaginal administration prepared by an ordinary formulation and including one or more active materials.

The compound of the present invention may be administered as a combination preparation by being combined with other pharmaceuticals for the purpose of:

1) supplement and/or enhancement of a prevention effect and/or a treatment effect of the compound;

2) improvement in pharmacokinetics and absorption and reduction of doses to be administered of the compound; and/or 3) reduction of side effects of the compound.

The combination preparation of the compound of the present invention with other pharmaceuticals may be administered in a form of a compounded agent in which both components are compounded in one preparation or may be in a form in which they are administered by means of separate preparations. The case of administration by means of separate preparations includes a simultaneous administration and administrations with time intervals. In the case of administrations with time intervals, the compound of the present invention may be firstly administered, followed by administering the other pharmaceutical or the other pharmaceutical may be administered firstly, followed by administering the compound of the present invention. Methods for each of the administrations may be the same or different.

The combination preparations with other pharmaceuticals which supplement and/or enhance the prevention and/or treatment effect of the compound of the present invention are not limited to those exemplified in the present specification. Also, the combination preparations with other pharmaceuticals which supplement and/or enhance the prevention and/or treatment effect of the compound of the present invention include not only the ones which have been found up to now but also ones which will be found in future on the basis of mechanisms described in the present specification.

The diseases against which the combined drugs as described above have preventive and/or therapeutic effects are not particularly restricted. Namely, they may be diseases with which the preventive and/or therapeutic effects of the compounds of the present invention can be complemented and/or enhanced.

For example, gene therapy, cell transplantation therapy, drug therapy, and the like each of which can induce angiogenesis are possible as another method used for complementing and/or enhancing preventive and/or therapeutic effects against a peripheral arterial disease such as arteriosclerosis obliterans, thromboangiitis obliterans, Buerger's disease, or diabetic neuropathy, congestive heart failure, multiple organ failure, bedsore, burn, ulcerative colitis, and the like, which are an EDG-1-mediated diseases. An EDG-1 agonist can be used together with any one of those methods. In the case of gene therapy, for example, a method for intramuscular injection of genes such as VEGF or HGF into an ischemic region is useful, and the EDG-1 agonist can be used together with this method. Cell transplantation therapy is a method for supplementing vascular endothelial cells which includes: for example, myelomonocytes (divided stem cells) separated from self-bone marrow liquid is concentrated to be injected into an ischemic region by intramuscular, and the EDG-1 agonist can be used together with this treatment. Drug therapy includes using a drug which has other angiogenetic effects, and the EDG-1 agonist is thought to exert its effect by being used with the following drugs. Examples of a proteinous therapeutic agent include VEGF, HGF, FGF, HIF-$\alpha$, and PDGF. Examples of a low-molecular-weight therapeutic agent include alprostadil, alcloxa, tretinoin tocopheryl, and MCI-154.

In addition, other immunosuppressants, antibiotics, or the like may be cited as drugs to be used for complementing and/or enhancing preventive and/or therapeutic effects on rejection in transplantation, which is an EDG-1 and/or EDG-6-mediated disease. Steroids, nonsteroidal anti-inflammatory drugs (NSAIDs), disease modifying antirheumatic drugs (DMARDs, slow-acting antirheumatic drugs), other immunosuppressants, T cell inhibitors, anti-inflammatory enzyme preparations, cartilage protecting agents, prostaglandins, prostaglandin synthase inhibitors, IL-1 inhibitors, IL-6 inhibitors (including protein preparations such as an anti-IL-6 receptor antibody), TNF-$\alpha$ inhibitors (including protein preparations such as an anti-TNF-$\alpha$ antibody), interferon $\gamma$ agonists, phosphodiesterase inhibitors, metalloproteinase inhibitors, and the like can be cited as drugs to be used in preventing and/or treating autoimmune diseases. EDG-1 and/or EDG-6 agonists can be used in combination with those drugs. Concerning drugs to be used for complementing and/or enhancing the preventive and/or therapeutic effects on allergic diseases, examples of drugs to be used for complementing and/or enhancing the preventive and/or therapeutic effects on, for example, atopic dermatitis include immunosuppressants, steroids, nonsteroidal anti-inflammatory drugs, prostaglandins, antiallergic agents, mediator release inhibitors, antihistaminic drugs, forskolin preparations, phosphodiesterase inhibitors, and cannabinoid-2 receptor stimulants.

Examples of the immunosuppressants include azathioprine (trade name: IMULAN and AZANIN), mizoribine (trade name: BREDININ), methotrexate (trade name: METHOTREXATE, RHEUMATREX), mycophenolate mofetil (trade name: CELLCEPT), cyclophosphamide (trade name: ENDOXAN P), ciclosporin A (trade name: NEORAL, SANDIMMUN), tacrolimus (FK506, trade name: PROGRAF), sirolimus (RAPAMYCIN), everolimus (trade name: CERTICAN), prednisolone (trade name: PREDONIN), methylprednisolone (trade name: MEDROL), orthoclone OKT3 (trade name: MUROMONAB CD3), anti human lymphocyte globulin (ALG, trade name: ALBULIN), deoxyspergualin (DSG, gusperimus hydrochloride, and trade name: SPANIDIN).

Examples of the antibiotics include cefuroxime sodium, meropenem trihydrate, netilmicin sulfate, sisomicin sulfate, ceftibuten, PA-1806, IB-367, tobramycin, PA-1420, doxorubicin, astromicin sulfate, or cefetamet pivoxil hydrochloride. Examples of antibiotics as inhalants include PA-1806, IB-367, tobramycin, PA-1420, doxorubicin, astromicin sulfate, or cefetamet pivoxil hydrochloride.

Examples of the steroid, in the case of external preparations, include clobetasol propionate, diflorasone diacetate, fluocinonide, mometasone furancarboxylate, betamethasone dipropionate, betamethasone butyrate propionate, betamethasone valerate, difluprednate, budesonide, diflucortolone valerate, amcinonide, halcinonide, dexamethasone, dexamethasone propionate, dexamethasone valerate, dexamethasone acetate, hydrocortisone acetate, hydrocortisone butyrate, hydrocortisone butyrate propionate, deprodone propionate, prednisolone valerate acetate, fluocinolone acetonide, beclomethasone propionate, triamcinolone acetonide, flumetasone pivalate, alclometasone dipropionate, clobetasone butyrate, prednisolone, beclomethasone dipropionate, and fludroxycortide. Examples of internal medicines and injections include cortisone acetate, hydrocortisone, hydrocortisone sodium phosphate, hydrocortisone sodium succinate, fludrocortisone acetate, prednisolone, prednisolone acetate, prednisolone sodium succinate, prednisolone butylacetate, prednisolone sodium phosphate, halopredone acetate, methylprednisolone, methylprednisolone acetate, methylprednisolone sodium succinate, triamcinolone, triamcinolone diacetate, triamcinolone acetonide, dexamethasone, dexamethasone acetate, dexamethasone sodium phosphate, dexamethasone palmitate, paramethasone acetate, and betamethasone. Examples of inhalants include beclomethasone dipropionate, fluticasone propionate, budesonide, flunisolide, triamcinolone, ST-126P, ciclesonide, dexamethasone palmitate, mometasone furoate, prasterone sulfate, deflazacort, methylprednisolone suleptanate, and methylprednisolone sodium succinate.

Examples of the nonsteroidal antiinflammatory drug (NSAID) include sasapyrine, sodium salicylate, aspirin, aspirin dialuminate formulation, diflunisal, indomethacin, suprofen, ufenamate, dimethylisopropyl azulen, bufexamac, felbinac, diclofenac, tolmetin sodium, Clinoril, fenbufen, nabumetone, proglumetacin, indomethacin farnesil, acemetacin, proglumetacin maleate, amfenac sodium, mofezolac, etodolac, ibuprofen, ibuprofen piconol, naproxen, flurbiprofen, flurbiprofen axetil, ketoprofen, fenoprofen calcium, tiaprofenen, oxaprozin, pranoprofen, loxoprofen sodium, aluminoprofen, zaltoprofen, mefenamic acid, aluminum mefenamate, tolfenamic acid, floctafenine, ketophenylbutazone, oxyfenbutazone, piroxicam, tenoxicam, anpiroxicam, napageln cream, epirizole, tiaramide hydrochloride, tinoridine hydrochloride, emorfazone, sulpyrine, Migrenin, Saridon, Sedes G, Amipylo N, Sorbon, pyrine system antipyretics, acetaminophen, phenacetin, dimethothiazine mesylate, simetride formulation, and antipyrine system antipyretics.

Examples of the disease modifying anti-rheumatic drug (DMARDs, slow-acting anti-rheumatic drug) include aurothioglucose, aurothiomalate sodium, aurandfin, actarit, D-penicillamine preparations, lobenzarit disodium, bucillamine, hydroxychloroquine, salazosulfapyridine, methotrexate, and leflunomide.

Examples of the antiinflammatory enzyme preparations include lysozyme chloride, bromelain, pronase, serrapeptase, or streptokinase-streptodornase formulation.

Examples of the cartilage protecting agents include hyaluronate sodium, glucosamine, chondroitin sulfate, and glucosaminoglycan polysulfate.

Examples of the prostaglandins (hereinafter abbreviated as "PG") include a PG receptor agonist, and a PG receptor antagonist. Examples of the PG receptor include PGE receptor (EP1, EP2, EP3, EP4), PGD receptor (DP, CRTH2), PGF receptor (FP), PGI receptor (IP), or TX receptor (TP).

Examples of the prostaglandin synthase inhibitor include salazosulfapyridine, mesalazine, olsalazine, 4-aminosalicylic acid, JTE-522, auranofin, carprofen, diphenpyramid, flunoxaprofen, flurbiprofen, indomethacin, ketoprofen, lornoxicam, loxoprofen, Meloxicam, oxaprozin, parsalmide, piproxen, piroxicam, piroxicam betadex, piroxicam cinnamate, tropine indomethacinate, zaltoprofen, and pranoprofen.

Examples of the IL-1 inhibitors (including protein preparations such as a human IL-1 receptor antagonist) include anakinra.

Examples of the IL-6 inhibitors (including protein preparations such as an anti-IL-6 receptor antibody) include MRA.

Examples of the TNF-α inhibitors (including protein preparations such as an anti-TNF-α antibody) include infliximab, adalimumab, and etanercept.

Examples of the phosphodiesterase inhibitor include rolipram, cilomilast (trade name: Ariflo), Bay 19-8004, NIK-616, roflumilast (BY-217), cipamfylline (BGL-61063), atizolam (CP-80633), SCH-351591, YM-976, V-11294A, PD-168787, D-4386, IC-485, or ONO-6126 as a PDE-4 inhibitor.

Examples of the mediator release inhibitor include tranilast, sodium cromoglicate, anlexanox, repirinast, ibudilast, tazanolast, and pemilolast potassium.

Examples of the antihistaminic drugs include ketotifen fumarate, mequitazine, azelastine hydrochloride, oxatomide, terfenadine, emedastine fumarate, epinastine hydrochloride, astemizole, ebastin, cetirizine hydrochloride, bepotastine, fexofenadine, lolatadine, deslolatadine, olopatadine hydrochloride, TAK-427, ZCR-2060, NIP-530, mometasone furoate, mizolastine, BP-294, andolast, auranofin, and acrivastine.

Examples of the drugs to be used in combination of the compound of the present invention for complementing and/or enhancing preventive and/or therapeutic effects against diabetes, particularly against type II diabetes, include a sulfonylurea drug, a biguanide drug, an α-glucosidase inhibitor, an insulin-resistance improver, an insulin secretion promoter, an insulin formulation, a DPP (dipeptidyl peptidase) 4 inhibitor, a PTP1B inhibitor, a β3 adrenaline receptor agonist, and a therapeutic agent for diabetes complications.

Examples of the sulfonylurea drug include acetohexamide, glibenclamide, gliclazide, glyclopyramide, chlorpropamide, tolazamide, tolbutamide, and glimepiride. Examples of the biguanide drug include buformin hydrochloride and metoformin hydrochloride. Examples of the α-glucosidase inhibitor include acarbose and voglibose. Examples of the insulin-resistance improver include pioglitazone, troglitazone, englitazone, MCC-555, and rosiglitazone. Examples of the insulin secretion promoter include nateglinide and repaglinide. Examples of the DPP4 inhibitor include NVP-DPP728A. Examples of the β3 adrenaline receptor agonist include AJ9677, L750355, and CP331648. Examples of the therapeutic agent for diabetes complications include epalrestat.

EFFECT OF THE INVENTION

The compound of the present invention is a compound capable of binding S1P receptor (in particular, EDG-1 and/or EDG-6). Accordingly, the compound is useful as a preventing and/or treating agent for mammals (for example, human, or non-human animals such as simian, ovine, bovine, equine, canine, feline, leporine, rat, and mouse), for: rejection in transplantation; rejection of a transplanted organ; graft versus host disease; an autoimmune disease (e.g., systemic lupus erythematosus, rheumatoid arthritis, multiple sclerosis, psoriasis, ulcerative colitis, Crohn's disease, myasthenia gravis, and autoimmune diabetes); an allergic disease (e.g., atopic dermatitis, pollen disease and food allergy); asthma; infectious disease; ulcer; lymphoma; malignant tumor (e.g., cancer); leukemia; and a disease associated with lymphocyte infiltration into a tissue; a peripheral arterial disease such as arteriosclerosis obliterans, thromboangiitis obliterans, Buerger's disease, or diabetic neuropathy; varicose vein such as hemorrhoid, anal fissure, or anal fistula; dissecting aneurysm of the aorta; sepsis; an inflammatory disease such as angiitis, nephritis, or pneumonia; various edematous disease involved in ischemia of various organs and increase of the blood permeability, for example, cerebral stroke, ischemia-reperfusion injury, cerebral infarction, myocardial infarction, angina, congestive heart failure, pleuritis, DIC, or multiple organ failure; bedsore; burn; trauma injury; inflammatory bowel disease; genetic disease; osteoporosis; arteriosclerosis; fibrosis such as pulmonary fibrosis or liver fibrosis; interstitial pneumotitis; chronic hepatitis; liver cirrhosis; chronic renal insufficiency; renal glomerular sclerosis; diabetes; and the like. In addition, the compound of the present invention is useful as a preoperative, postoperative, and/or prognostic activator for blood vessel accompanying transplantation of various organs, tissues, and/or cells, for example, as an adhesion activator of transplanted organs such as heart transplantation, renal transplantation, dermal transplantation, or liver transplantation. In addition, the compound of the present invention is useful, not only in vivo but also in vitro, as an adjusting agent such as a differentiation activator of cells or the like.

BEST MODE FOR CARRYING OUT THE INVENTION

The present invention will be described in greater detail by the following Examples. However, the present invention is not construed as being restricted thereto. Concerning chromatographic separation or TLC, a solvent in parentheses corresponds to an eluting solvent or a developing solvent employed and a ratio is expressed in volume. Aqueous ammonia to be used is a commercially available 28% aqueous ammonia. Unless otherwise noted, numbers shown in NMR are measurement values of $^1$H-NMR when chloroform-d is used as a solvent for the measurement. Unless otherwise noted, MS was performed by using the ESI (electrospray ionization) method and only cationic ions (pos.) were detected.

HPLC was conducted under the following measurement conditions.
Column: Xterra (trade name) MS $C_{18}$ 5 μm, 4.6×50 mm I.D.,
Flow rate: 3 ml/min,
Solvent A: 0.1% aqueous solution of trifluoroacetic acid
Solvent B: 0.1% solution of trifluoroacetic acid in acetonitrile.
Within 0.5 minute following the initiation of the measurement, the mixing rate of the solution A to the solution B was fixed to 95:5. Subsequently, the mixing ratio of the solution A to the solution B was linearly changed to 0:100 within 2.5 minutes, and then fixed to 0:100 during 0.5 minute. In the subsequent 0.01 minute, the mixing rate of the solution A to the solution B was linearly changed to 95:5.

EXAMPLE 1

3-[4-(3-phenylpropoxy)phenyl]propanenitrile

To a solution of 4-hydroxyphenylpropanenitrile (5.25 g) in N,N-dimethyl formamide (40 mL), 3-phenylpropyl bromide (7.1 g) and potassium carbonate (14.79 g) were added, followed by stirring at room temperature for 16 hours. Then, the reaction mixture was diluted with diethyl ether and an organic layer was successively washed with water and brine. After the organic layer was dried, the solvent was concentrated and the obtained residue was purified by silica gel column chromatography (hexane:ethyl acetate=5:1) to give the title compound (8.54 g) having the following physical properties.
TLC: Rf 0.29 (hexane:ethyl acetate=5:1);
MS (EI, Pos.): 265 (M$^+$), 225, 118, 107, 91;
NMR: δ 7.24-7.36 (m, 2H), 7.17-7.24 (m, 3H), 7.09-7.15 (m, 2H), 6.81-6.90 (m, 2H), 3.94 (t, J=6.32 Hz, 2H), 2.89 (t, J=7.32 Hz, 2H), 2.77-2.84 (m, 2H), 2.57 (t, J=7.32 Hz, 2H), 2.01-2.18 (m, 2H).

EXAMPLE 2

3-[4-(3-phenylpropoxy)phenyl]propylamine

To a solution of the compound (8.04 g) prepared in Example 1 in diethyl ether (100 mL), lithium aluminum hydride (2.30 g) was added at 0° C., followed stirring for 2 hours. To the reaction mixture, small amount of a saturated aqueous sodium sulfate solution was added at 0° C., followed by drying with magnesium sulfate. The resultant was added with 1N aqueous sodium hydroxide solution (20 mL) and tetrahydrofuran (200 mL) and the mixture was heated to reflux for 20 minutes. After the reaction mixture was stood to cool, the insoluble matters were filtered. Then, the filtrate was dried with sodium sulfate and the solvent was concentrated. Then, the obtained residue was purified by silica gel column chromatography (dichloroform:methanol:triethylamine=90:10:1) to give the compound of the present invention (2.50 g) having the following physical properties.
TLC: Rf 0.20 (chloroform:methanol:triethylamine=90:10:1);
MS (EI, Pos.): 269 (M$^+$), 252, 134, 118, 91;
NMR: δ 7.25-7.33 (m, 2H), 7.15-7.25 (m, 3H), 7.04-7.12 (m, 2H), 6.77-6.86 (m, 2H), 3.95 (t, J=6.32 Hz, 2H), 2.76-2.85 (m, 2H), 2.67-2.74 (m, 2H), 2.55-2.63 (m, 2H), 2.36 (s, 2H), 2.02-2.17 (m, 2H), 1.70-1.84 (m, 2H).

EXAMPLE 3

N-(t-butoxycarbonyl)-N-{3-[4-(3-phenyl propoxy)phenyl]propyl}-β-alanine

To a solution of the compound (941 mg) prepared in Example 2 in methanol (4 mL), methyl acrylate (301 mg) was added, followed by stirring at room temperature for 26 hours. The reaction mixture was concentrated and to a suspension of the obtained residue in dichloromethane (6 mL), di-t-butyl dicarbonate (Boc$_2$O) (762 mg) was added, followed by stirring at room temperature for 16 hours. Then, the reaction mixture was concentrated and the obtained residue was purified by silica gel column chromatography (hexane:ethyl acetate=6:1). To a mixed solution of the obtained compound (778 mg) in methanol (2 mL)-dioxane (1 mL), a 2N sodium hydroxide solution (1.71 mL) was added, followed by stirring at room temperature for 2 hours. After concentrating the reaction mixture, the residue was added with water and 1N hydrochloric acid (4 mL) and the mixture was extracted with diethyl ether. Then, the organic layer was washed with brine. After the organic layer was dried, the resultant was concentrated to give the compound of the present invention (723 mg) having the following physical properties.

TLC: Rf 0.73 (chloroform:methanol:acetic acid=90:10:5);

MS (FAB, Pos., Glycerin+m-NBA): 442 (M+H)$^+$, 385, 342, 252, 225, 102, 91, 57;

NMR: δ 7.24-7.35 (m, 2H), 7.13-7.24 (m, 3H), 7.00-7.11 (m, 2H), 6.74-6.87 (m, 2H), 3.94 (t, J=6.22 Hz, 2H), 3.47 (t, J=6.77 Hz, 2H), 3.23 (s, 2H), 2.73-2.86 (m, 2H), 2.57-2.68 (m, 2H), 2.48-2.57 (m, 2H), 2.01-2.17 (m, 2H), 1.70-1.90 (m, 2H), 1.44 (s, 9H).

EXAMPLE 4

$N^3$-{3-[4-(3-phenylpropoxy)phenyl]propyl}-$N^1$-(phenylsulfonyl)-β-alaninamide hydrochloride

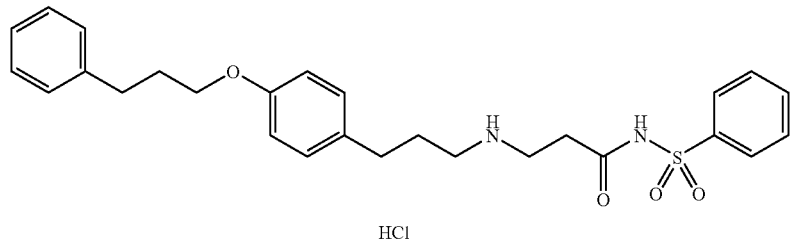

HCl

To a solution of the compound (110 mg) prepared in Example 3 in dichloromethane (4 mL), benzenesulfonamide (43 mg), N,N-dimethylaminopyridine (37 mg), and 1-ethyl-3-[3-(dimethylamino)propyl]carbodiimide (EDC) hydrochloride (58 mg) were added at 0° C., followed by stirring for 24 hours. After the reaction mixture was diluted with ethyl acetate, the resultant was successively washed with 1N hydrochloric acid and brine, dried and concentrated. To the obtained compound (150 mg), a 4N hydrogen chloride-ethyl acetate solution (6 mL) was added at 0° C., followed by stirring for 2 hours. The reaction mixture was concentrated and the obtained residue was added with diisopropyl ether. Then, the precipitate was collected by filtration and dried. Thus, the compound of the present invention (109 mg) having the following physical properties was obtained.

TLC: Rf 0.44 (chloroform:methanol:acetic acid=90:10:5);
MS: 961 (2M+H)$^+$, 481 (M+H)$^+$;

NMR (CD$_3$OD): δ 1.92 (m, 2H), 2.04 (m, 2H), 2.61 (t, J=7.4 Hz, 2H), 2.72 (t, J=6.4 Hz, 2H), 2.79 (m, 2H), 2.93 (m, 2H), 3.17 (t, J=6.4 Hz, 2H), 3.92 (t, J=6.2 Hz, 2H), 6.83 (m, 2H), 7.12 (m, 2H), 7.22 (m, 5H), 7.57 (m, 2H), 7.68 (m, 1H), 8.02 (m, 2H).

EXAMPLE 5

1-{[6-(4-phenylbutoxy)-2-naphthyl]methyl}piperidine

To a solution in 6-(4-phenylbutoxy)-2-formylnaphthalene (50 mg) in dichloroethane (0.5 mL), piperidine (20 μL) and triacetoxy sodium borohydride (72 mg) were added, followed by stirring at room temperature for 18 hours. The reaction mixture was added with a 1N aqueous sodium hydroxide solution, and then the mixture was extracted with chloroform. After concentrating the organic layer, the obtained residue was purified by silica gel column chromatography (dichloroform:methanol:acetic acid=120:10:1) to give the title compound (60 mg) having the following physical properties.

TLC: Rf 0.79 (chloroform:methanol:aqueous ammonia=80:10:1);
MS: 374 (M+H)$^+$, 289;

NMR (CD$_3$OD): δ 7.62-7.74 (m, 3H), 7.41 (dd, J=8.51, 1.74 Hz, 1H), 7.06-7.31 (m, 7H), 3.99-4.15 (m, 2H), 3.62 (s, 2H), 2.62-2.78 (m, 2H), 2.37-2.54 (m, 4H), 1.76-1.90 (m, 4H), 1.53-1.67 (m, 4H), 1.40-1.53 (m, 2H).

EXAMPLE 5-1 TO EXAMPLE 5-16

The procedure of Example 5 was followed but using a corresponding carbonyl compound as a substitute for 6-(4-phenylbutoxy)-2-formylnaphthalene while using a corresponding amine compound as a substitute for piperidine. Thus, the compound of the present invention having the following physical properties was obtained.

EXAMPLE 5-1

1-{[6-(3-phenylpropoxy)-2-naphthyl]methyl}piperidine

TLC: Rf 0.82 (chloroform:methanol: aqueous ammonia=80:10:1);
MS: 360 (M+H)$^+$, 275;

NMR (CD$_3$OD): δ 7.64-7.76 (m, 3H), 7.41 (dd, J=8.14, 1.56 Hz, 1H), 7.20-7.30 (m, 4H), 7.09-7.18 (m, 3H), 4.07 (t, J=6.22 Hz, 2H), 3.62 (s, 2H), 2.84 (t, J=7.45 Hz, 2H), 2.38-2.53 (m, 4H), 1.99-2.24 (m, 2H), 1.52-1.69 (m, 4H), 1.42-1.52 (m, 2H).

EXAMPLE 5-2

1-{[6-(4-phenylbutoxy)-3,4-dihydronaphthalen-2-yl]methyl}piperidine

TLC: Rf 0.74 (chloroform:methanol:aqueous ammonia=80:10:1);
MS: 376 (M+H)$^+$, 291, 159;

NMR (CD$_3$OD): δ 7.06-7.34 (m, 5H), 6.89 (d, J=7.68 Hz, 1H), 6.65 (s, 1H), 6.59-6.70 (m, 1H), 6.30 (s, 1H), 3.86-4.00 (m, 2H), 3.05 (s, 2H), 2.75 (t, J=8.05 Hz, 2H), 2.59-2.71 (m, 2H), 2.35-2.52 (m, 4H), 2.27 (t, J=8.05 Hz, 2H), 1.69-1.84 (m, 4H), 1.54-1.67 (m, 4H), 1.39-1.53 (m, 2H).

EXAMPLE 5-3

1-({6-[(5-phenylpentyl)oxy]-2-naphthyl}methyl)piperidine

TLC: Rf 0.63 (chloroform:methanol: aqueous ammonia=80:10:1);
MS: 388 (M+H)$^+$, 303;

NMR: δ 7.60-7.75 (m, 3H), 7.43 (dd, J=8.33, 1.74 Hz, 1H), 7.23-7.35 (m, 2H), 7.07-7.23 (m, 5H), 4.06 (t, J=6.50 Hz, 2H), 3.59 (s, 2H), 2.66 (t, J=7.68 Hz, 2H), 2.32-2.50 (m, 4H), 1.80-1.95 (m, 2H), 1.65-1.80 (m, 2H), 1.49-1.64 (m, 6H), 1.34-1.49 (m, 2H).

EXAMPLE 5-4

1-({6-[(5-phenylpentyl)oxy]-2-naphthyl}methyl) azetidine

TLC: Rf 0.52 (chloroform:methanol:aqueous ammonia=80:10:1);
MS: 360 (M+H)$^+$, 303;
NMR: δ 7.59-7.73 (m, 3H), 7.36 (dd, J=8.33, 1.74 Hz, 1H), 7.23-7.33 (m, 2H), 7.04-7.23 (m, 5H), 4.05 (t, J=6.50 Hz, 2H), 3.68 (s, 2H), 3.24 (t, J=7.05 Hz, 4H), 2.66 (t, J=7.87 Hz, 2H), 2.02-2.19 (m, 2H), 1.80-1.96 (m, 2H), 1.64-1.78 (m, 2H), 1.44-1.63 (m, 2H).

EXAMPLE 5-5

1-({6-[(5-phenylpentyl)oxy]-2-naphthyl}methyl) pyrrolidine

TLC: Rf 0.54 (chloroform:methanol:aqueous ammonia=80:10:1);
MS: 374 (M+H)$^+$, 303;
NMR: δ 7.62-7.75 (m, 3H), 7.44 (dd, J=8.42, 1.46 Hz, 1H), 7.23-7.32 (m, 2H), 7.06-7.23 (m, 5H), 4.06 (t, J=6.50 Hz, 2H), 3.73 (s, 2H), 2.66 (t, J=7.69 Hz, 2H), 2.45-2.61 (m, 4H), 1.64-1.96 (m, 8H), 1.46-1.64 (m, 2H).

EXAMPLE 5-6

4-({6-[(5-phenylpentyl)oxy]-2-naphthyl}methyl) morpholine

TLC: Rf 0.86 (chloroform:methanol:aqueous ammonia=80:10:1);
MS: 390 (M+H)$^+$, 303;
NMR: δ 7.62-7.75 (m, 3H), 7.44 (dd, J=8.42, 1.83 Hz, 1H), 7.23-7.33 (m, 2H), 7.06-7.24 (m, 5H), 4.06 (t, J=6.59 Hz, 2H), 3.68-3.76 (m, 4H), 3.62 (s, 2H), 2.66 (t, J=7.50 Hz, 2H), 2.43-2.53 (m, 4H), 1.81-1.94 (m, 2H), 1.64-1.80 (m, 2H), 1.48-1.63 (m, 2H).

EXAMPLE 5-7

4-({6-[(5-phenylpentyl)oxy]-2-naphthyl}methyl) thiomorpholine

TLC: Rf 0.94 (chloroform:methanol:aqueous ammonia=80:10:1);
MS: 406 (M+H)$^+$, 303;
NMR: δ 7.58-7.75 (m, 3H), 7.42 (dd, J=8.42, 1.65 Hz, 1H), 7.23-7.34 (m, 2H), 7.06-7.24 (m, 5H), 4.06 (t, J=6.59 Hz, 2H), 3.63 (s, 2H), 2.60-2.79 (m, 10H), 1.80-1.97 (m, 2H), 1.63-1.79 (m, 2H), 1.48-1.64 (m, 2H).

EXAMPLE 5-8

8-({6-[(5-phenylpentyl)oxy]-2-naphthyl}methyl)-1,4-dioxa-8-azaspiro[4.5]decane

TLC: Rf 0.80 (chloroform:methanol:aqueous ammonia=80:10:1);
MS: 446 (M+H)$^+$, 303;
NMR: δ 7.61-7.75 (m, 3H), 7.44 (dd, J=8.42, 1.65 Hz, 1H), 7.24-7.33 (m, 2H), 7.06-7.23 (m, 5H), 4.06 (t, J=6.59 Hz, 2H), 3.94 (s, 4H), 3.64 (s, 2H), 2.66 (t, J=7.87 Hz, 2H), 2.50-2.61 (m, 4H), 1.82-1.95 (m, 2H), 1.64-1.81 (m, 6H), 1.45-1.64 (m, 2H).

EXAMPLE 5-9

1-({6-[(5-phenylpentyl)oxy]-2-naphthyl}methyl) piperidin-4-ol

TLC: Rf 0.26 (chloroform:methanol:aqueous ammonia=80:10:1);
MS: 404 (M+H)$^+$, 303;
NMR: δ 7.59-7.74 (m, 3H), 7.43 (dd, J=8.33, 1.56 Hz, 1H), 7.24-7.35 (m, 2H), 7.07-7.24 (m, 5H), 4.06 (t, J=6.50 Hz, 2H), 3.66-3.78 (m, 1H), 3.62 (s, 2H), 2.72-2.87 (m, 2H), 2.66 (t, J=7.69 Hz, 2H), 2.09-2.26 (m, 2H), 1.81-1.97 (m, 4H), 1.45-1.80 (m, 7H).

EXAMPLE 5-10

N,N-dimethyl-1-{6-[(5-phenylpentyl)oxy]-2-naphthyl}methanamine

TLC: Rf 0.50 (chloroform:methanol:aqueous ammonia=80:10:1);
MS: 348 (M+H)$^+$, 303;
NMR: δ 7.59-7.74 (m, 3H), 7.41 (dd, J=8.51, 1.56 Hz, 1H), 7.23-7.34 (m, 2H), 7.06-7.23 (m, 5H), 4.06 (t, J=6.50 Hz, 2H), 3.54 (s, 2H), 2.66 (t, J=7.87 Hz, 2H), 2.27 (s, 6H), 1.81-1.95 (m, 2H), 1.61-1.79 (m, 2H), 1.46-1.63 (m, 2H).

EXAMPLE 5-11

N-ethyl-N-({6-[(5-phenylpentyl)oxy]-2-naphthyl}methyl)ethanamine

TLC: Rf 0.64 (chloroform:methanol:aqueous ammonia=80:10:1);
MS: 376 (M+H)$^+$, 303;
NMR: δ 7.62-7.74 (m, 3H), 7.45 (dd, J=8.51, 1.56 Hz, 1H), 7.23-7.33 (m, 2H), 7.06-7.23 (m, 5H), 4.06 (t, J=6.59 Hz, 2H), 3.68 (s, 2H), 2.66 (t, J=7.69 Hz, 2H), 2.56 (q, J=7.14 Hz, 4H), 1.81-1.96 (m, 2H), 1.65-1.80 (m, 2H), 1.48-1.63 (m, 2H), 1.06 (t, J=7.14 Hz, 6H).

EXAMPLE 5-12

2-[({6-[(5-phenylpentyl)oxy]-2-naphthyl}methyl) amino]ethanol

TLC: Rf 0.52 (chloroform:methanol:aqueous ammonia=80:10:1);
MS: 364 (M+H)$^+$, 303;
NMR (CD$_3$OD): δ 7.66-7.75 (m, 3H), 7.41 (dd, J=8.32, 1.56 Hz, 1H), 7.04-7.27 (m, 7H), 4.07 (t, J=6.40 Hz, 2H), 3.89 (s, 2H), 3.68 (t, J=5.49 Hz, 2H), 2.75 (t, J=5.49 Hz, 2H), 2.65 (t, J=7.59 Hz, 2H), 1.79-1.94 (m, 2H), 1.65-1.79 (m, 2H), 1.47-1.64 (m, 2H).

EXAMPLE 5-13

N-({6-[(5-phenylpentyl)oxy]-2-naphthyl}methyl) propan-1-amine

TLC: Rf 0.83 (chloroform:methanol:aqueous ammonia=80:10:1);

MS: 723 (2M+H)⁺, 362 (M+H)⁺, 303;
NMR (CD₃OD): δ 7.72 (s, 1H), 7.65-7.70 (m, 2H), 7.40 (dd, J=8.42, 1.65 Hz, 1H), 7.03-7.28 (m, 7H), 4.05 (t, J=6.41 Hz, 2H), 3.84 (s, 2H), 2.64 (t, J=7.50 Hz, 2H), 2.51-2.59 (m, 2H), 1.78-1.93 (m, 2H), 1.64-1.78 (m, 2H), 1.45-1.63 (m, 4H), 0.91 (t, J=7.41 Hz, 3H).

EXAMPLE 5-14

N-methyl-1-{6-[(5-phenylpentyl)oxy]-2-naphthyl}methanamine

TLC: Rf 0.47 (chloroform:methanol:aqueous ammonia=80:10:1);
MS: 334 (M+H)⁺, 303, 214;
NMR (CD₃OD): δ 7.68-7.78 (m, 3H), 7.42 (dd, J=8.32, 1.92 Hz, 1H), 7.06-7.28 (m, 7H), 4.0.7 (t, J=6.50 Hz, 2H), 3.95 (s, 2H), 2.65 (t, J=7.59 Hz, 2H), 2.49 (s, 3H), 1.79-1.96 (m, 2H), 1.64-1.78 (m, 2H), 1.45-1.64 (m, 2H).

EXAMPLE 5-15

N-ethyl-N-({6-[(5-phenylpentyl)oxy]-2-naphthyl}methyl)amine

TLC: Rf 0.54 (chloroform:methanol:aqueous ammonia=80:10:1);
MS: 348 (M+H)⁺, 303;
NMR (CD₃OD): δ 7.67-7.75 (m, 3H), 7.41 (dd, J=8.42, 1.83 Hz, 1H), 7.05-7.28 (m, 7H), 4.07 (t, J=6.50 Hz, 2H), 3.89 (s, 2H), 2.70 (q, J=7.20 Hz, 2H), 2.67 (t, J=7.50 Hz, 2H), 1.79-1.93 (m, 2H), 1.64-1.78 (m, 2H), 1.47-1.63 (m, 2H), 1.16 (t, J=7.20 Hz, 3H).

EXAMPLE 5-16

N-isopropyl-N-({6-[(5-phenylpentyl)oxy]-2-naphthyl}methyl)amine

TLC: Rf 0.70 (chloroform:methanol:aqueous ammonia=80:10:1);
MS: 362 (M+H)⁺, 303;
NMR (CD₃OD): δ 7.66-7.76 (m, 3H), 7.41 (dd, J=8.33, 1.74 Hz, 1H), 7.04-7.28 (m, 7H), 4.05 (t, J=6.40 Hz, 2H), 3.88 (s, 2H), 2.82-2.96 (m, 1H), 2.63 (t, J=7.50 Hz, 2H), 1.77-1.92 (m, 2H), 1.62-1.77 (m, 2H), 1.44-1.62 (m, 2H), 1.13 (d, J=6.22 Hz, 6H).

EXAMPLE 6

N-[(1-{6-(3-phenylpropoxy)-2-naphthyl]methyl}azetidin-3-yl)carbonyl]benzenesulfonamide The procedure of Example 5 was followed but using 6-(3-phenylpropoxy)-2-formylnaphthalene as a substitute for 6-(4-phenylbutoxy)-2-formylnaphthalene while using 3-azetideine carboxylic acid as a substitute for piperidine. Then, the procedure of Example 4 was followed with the obtained compound to thereby give the compound of the present invention having the following physical properties.
TLC: Rf 0.48 (chloroform:methanol:aqueous ammonia=18:2:1);
MS: 515 (M+H)⁺;
NMR: δ 7.91 (d, J=7.00 Hz, 2H), 7.80 (s, 1H), 7.65 (d, I=8.80 Hz, 2H), 7.13-7.49 (m, 1H), 7.04 (d, J=2.70 Hz, 1H), 4.38-4.54 (m, 2H), 4.38 (s, 2H), 4.07 (t, J=6.20 Hz, 2H), 3.94 (t, J=10.10 Hz, 2H), 3.34-3.50 (m, 1H), 2.85 (t, J=7.40 Hz, 2H), 2.10-2.26 (m, 2H).

EXAMPLE 7

2-{4-[(5-phenylpentyl)oxy]phenyl}ethylamine

The procedures of Examples 1 and 2 were followed but using 5-phenylpentyl bromide as a substitute for 3-phenylpropyl bromide while using 4-hydroxyphenylacetonitrile as a substitute for 4-hydroxyphenylpropanenitrile. Thus, the compound of the present invention having the following physical properties was obtained.
TLC: Rf 0.37 (chloroform:methanol=9:1);
MS (APCI, Pos.): 239 (4+H)⁺.

EXAMPLE 8

3-hydroxy-4-methyl-N-(2-{4-[(5-phenylpentyl)oxy]phenyl}ethyl)benzamide

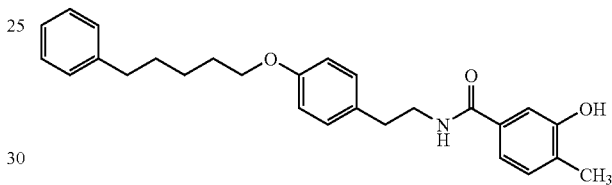

To a solution of hydrochloride (320 mg) of the compound prepared in Example 7 in dichloromethane (5 mL), 3-hydroxy-4-methylbenzoic acid (152 mg), N,N-dimethylaminopyridine (50 mg), triethylamine (0.7 mL), and 1-ethyl-3-[3-(dimethylamine)propyl]carbodiimide (EDC) hydrochloride (382 mg) were added at 0° C., followed by stirring for 24 hours. The reaction mixture was added with 1N hydrochloric acid and the mixture was extracted with ethyl acetate. The organic layer was successively washed with a saturated aqueous sodium hydrogen carbonate solution and brine. After the organic layer was dried, the resultant was concentrated to give the compound of the present invention (244 mg) having the following physical properties.
TLC: Rf 0.42 (hexane:ethyl acetate=1:1);
MS (APCI, Pos., 20V): 418 (M+H)⁺;
NMR (DMSO-d₆): δ 9.48 (s, 1H), 8.31 (t, J=5.4 Hz, 1H), 7.30-7.05 (m, 10H), 6.82 (d, J=8.1 Hz, 2H), 3.91 (t, J=6.6 Hz, 2H), 3.45-3.35 (m, 2H), 2.80-1.70 (m, 2H), 2.62-2.55 (m, 2H), 2.14 (s, 3H), 1.80-1.55 (m, 4H), 1.50-1.45 (m, 2H).

EXAMPLE 8-1 TO EXAMPLE 8-3

The procedure of Example 8 was followed but using a corresponding carboxylic acid compound as a substitute for 3-hydroxy-4-methylbenzoic acid. Thus, the compound of the present invention having the following physical properties was obtained.

EXAMPLE 8-1

3-[(E)-(hydroxyimino)methyl]-N-(2-{4-[(5-phenylpentyl)oxy]phenyl}ethyl)benzamide TLC: Rf 0.55 (hexane:ethyl acetate=1:1);
MS (APCI, Pos., 40V): 431 (M+H)⁺;

NMR: δ 8.14 (s, 1H), 7.89 (m, 1H), 7.70 (dd, J=2.1, 7.8 Hz, 1H), 7.68 (dd, J=1.5, 7.8 Hz, 1H), 7.43 (t, J=7.8 Hz, 1H), 7.30-7.15 (m, 5H), 7.13 (d, J=8.4 Hz, 2H), 6.85 (d, J=8.4 Hz, 2H), 3.94 (t, J=6.3 Hz, 2H), 3.68 (q, J=6.3 Hz, 2H), 2.87 (t, J=6.6 Hz, 2H), 2.64 (t, J=7.8 Hz, 2H), 1.90-1.50 (m, 6H).

EXAMPLE 8-2

3,5-bis(benzyloxy)-N-(2-{4-[(5-phenylpentyl)oxy]phenyl}ethyl)benzamide

TLC: Rf 0.31 (hexane:ethyl acetate=4:1);
MS (APCI, Pos, 40V): 600 (M+H)$^+$;
NMR (DMSO-$d_6$): δ 8.47 (t, J=5.7 Hz, 1H), 7.50-7.05 (m, 19H), 6.85-6.80 (m, 3H), 5.12 (s, 4H), 3.89 (t, J=6.6 Hz, 2H), 3.50-3.40 (m, 2H), 2.75 (t, J=7.5 Hz, 2H), 2.58 (t, J=7.5 Hz, 2H), 1.80-1.60 (m, 4H), 1.50-1.40 (m, 2H).

EXAMPLE 8-3

3,5-dihydroxy-N-(2-{4-[(5-phenylpentyl)oxy]phenyl}ethyl)benzamide

TLC: Rf 0.35 (chloroform:ethyl acetate=2:1);
MS (APCI, Pos., 40V): 420 (M+H)$^+$;
NMR (DMSO-$d_6$): δ 9.41 (s, 2H), 8.26 (t, J=5.7 Hz, 1H), 7.30-7.10 (m, 5H), 7.11 (d, J=8.7 Hz, 2H), 6.82 (d, J=8.7 Hz, 2H), 6.63 (d, J=2.1 Hz, 2H), 6.33 (t, J=2.1 Hz, 1H), 3.91 (t, J=6.6 Hz, 2H), 3.42-3.30 (m, 2H), 2.72 (t, J=7.8 Hz, 2H), 2.59 (t, J=7.8 Hz, 2H), 1.80-1.60 (m, 4H), 1.50-1.40 (m, 2H).

EXAMPLE 9

((2S)-1-{(2E)-3-[4-(4-phenylbutoxy)phenyl]prop-2-enoyl}pyrrolidine-2-yl)methanol To a solution of 4-(4-phenylbutoxy)cinnamic acid (500 mg) in dichloromethane (5 mL), a catalytic amount of N,N-dimethyl formamide and oxalyl chloride (0.3 mL) were added at 0° C. After stirring for 1 hour, the mixture was concentrated to obtain acid chloride. To a solution of (2S)-prolinol (512 mg) in dichloromethane (10 mL), triethylamine (1.2 mL) and a solution of the obtained acid chloride in dichloromethane (5 mL) were dropped at 0° C., followed by stirring for 30 minutes. The reaction mixture was added with 1N hydrochloric acid and was extracted with ethyl acetate. The organic layer was successively washed with a saturated aqueous sodium hydrogen carbonate solution and brine, dried and concentrated. The obtained residue was purified by silica gel column chromatography (hexane:ethyl acetate=10:1) to give the compound of the present invention (649 mg) having the following physical properties.
TLC: Rf 0.10 (hexane:ethyl acetate=1:1);
MS (APCI, Pos, 40V): 380 (M+H)$^+$;
NMR: δ 7.68 (d, J=15.4 Hz, 1H), 7.46 (d, J=8.8 Hz, 2H), 7.30-7.10 (m, 5H), 6.87 (d, J=8.8 Hz, 2H), 6.57 (d, J=15.4 Hz, 1H), 4.50-4.30 (m, 1H), 4.02-3.95 (m, 2H), 3.80-3.60 (m, 4H), 2.80-2.60 (m, 2H), 2.20-1.90 (m, 2H), 1.90-1.80 (m, 4H), 1.80-1.50 (m, 2H).

EXAMPLE 9-1 TO EXAMPLE 9-24

The procedure of Example 9 was followed but using a corresponding carboxylic acid compound as a substitute for 4-(4-phenylbutoxy)cinnamic acid while using a corresponding amine compound as a substitute for (2S)-prolinol. Thus, the compound of the present invention having the following physical properties was obtained.

EXAMPLE 9-1

(2E)-N-(2-hydroxyethyl)-3-[4-(4-phenylbutoxy)phenyl]acrylamide

TLC: Rf 0.42 (chloroform:methanol=9:1);
MS (MALDI, Pos): 362 (M+Na)$^+$, 340 (M+H)$^+$;
NMR: δ 7.58 (d, J=15.4 Hz, 1H), 7.42 (d, J=8.8 Hz, 2H), 7.38-7.15 (m, 5H), 6.84 (d, J=8.8 Hz, 2H), 6.28 (d, J=15.4 Hz, 1H), 6.25-6.10 (m, 1H), 4.00-3.90 (m, 2H), 3.80-3.70 (m, 2H), 3.60-3.50 (m, 2H), 2.80-2.60 (m, 2H), 1.90-1.80 (m, 4H).

EXAMPLE 9-2

1-{3-[4-(6-phenylhexyl)phenyl]propanoyl}-L-prolinamide

TLC: Rf 0.26 (chloroform:methanol=9:1);
MS (APCI, Pos. 40V): 407 (M+H)$^+$;
NMR: δ 7.29-7.07 (m, 9H), 7.01-6.92 and 5.83-5.77 and 5.44-5.22 (br, 2H), 4.61-4.58 and 4.14-4.10 (m, 1H), 3.62-3.25 (m, 2H), 2.96 (t, J=7.8 Hz, 2H), 2.65-2.50 (m, 6H), 2.44-2.36 (m, 1H), 2.19-1.71 (m, 3H), 1.64-1.54 (m, 4H), 1.40-1.26 (m, 4H).

EXAMPLE 9-3

1-(3-{4-[(5-phenylpentyl)oxy]phenyl}propanoyl)-L-prolinamide

TLC: Rf 0.31 (chloroform:methanol=9:1);
MS (APCI, Pos. 40V): 409 (M+H)$^+$;
NMR: δ 7.31-7.08 (m, 7H), 6.83-6.76 (m, 2H), 7.03-6.92, 5.88-5.82 and 5.56-5.28 (br, 2H), 4.61-4.58 and 4.15-4.12 (m, 1H), 3.92 (t, J=6.6 Hz, 2H), 3.62-3.26 (m, 2H), 2.93 (t, J=7.8 Hz, 2H), 2.66-2.48 (m, 4H) 2.43-2.36 (m, 1H), 2.18-1.64 (m, 7H), 1.55-1.44 (m, 2H).

EXAMPLE 9-4

1-(3-{4-[(5-phenylpentyl)oxy]phenyl}propanoyl)pyrrolidine

TLC: Rf 0.26 (hexane:ethyl acetate=1:2);
MS (APCI, Pos. 40V): 366 (M+H)$^+$;
NMR: δ 7.32-7.09 (m, 7H), 6.84-6.77 (m, 2H), 3.92 (t, J=6.6 Hz, 2H), 3.46 (t, J=6.6 Hz, 2H), 3.28 (t, J=6.6 Hz, 2H), 2.92 (t, J=7.6 Hz, 2H), 2.64 (t, J=7.6 Hz, 2H), 2.52 (t, J=7.6 Hz, 2H), 1.95-1.41 (m, 10H).

EXAMPLE 9-5

N-phenyl-3-{4-[(5-phenylpentyl)oxy]phenyl}propanamide

TLC: Rf 0.22 (hexane:ethyl acetate=4:1);
MS (APCI, Pos. 40V): 388 (M+H)$^+$;

NMR: δ 7.44-7.04 (m, 13H), 6.85-6.78 (m, 2H), 3.92 (t, J=6.6 Hz, 2H), 2.99 (t, J=7.6 Hz, 2H), 2.68-2.58 (m, 4H), 1.87-1.41 (m, 6H).

EXAMPLE 9-6

(2S)-2-(methoxymethyl)-1-(3-{4-[(5-phenylpentyl)oxy]phenyl}propanoyl)pyrrolidine TLC: Rf 0.27 (hexane:ethyl acetate=1:1);
MS (APCI, Pos. 40V): 410 (M+H)$^+$;
NMR: δ 7.30-7.10 (m, 7H), 6.83-6.78 (m, 2H), 4.28-4.23 and 3.94-3.83 (m, 3H), 3.57-3.10 (m, 7H), 2.95-2.88 (m, 2H), 2.66-2.50 (m, 4H), 2.02-1.64 (m, 8H), 1.55-1.44 (m, 2H).

EXAMPLE 9-7

N-(3-acetylphenyl)-3-{4-[(5-phenylpentyl)oxy]phenyl}propanamide

TLC: Rf 0.39 (hexane:ethyl acetate=2:1);
MS (APCI, Pos. 40V): 430 (M+H)$^+$;
NMR: δ 7.93 (s, 1H), 7.81 (d, J=8.2 Hz, 1H), 7.67 (d, J=8.0 Hz, 1H), 7.43-7.11 (m, 9H), 6.85-6.78 (m, 2H), 3.92 (t, J=6.4 Hz, 2H), 3.00 (t, J=7.5 Hz, 2H), 2.69-2.58 (m, 7H), 1.87-1.63 (m, 4H), 1.56-1.41 (m, 2H).

EXAMPLE 9-8

1-(3-{4-[(5-phenylpentyl)oxy]phenyl}propanoyl)-D-prolinamide

TLC: Rf 0.25 (chloroform:methanol=19:1);
MS (APCI, Pos. 40V): 409 (M+H)$^+$;
NMR: δ 7.30-7.08 (m, 7H), 6.83-6.78 (m, 2H), 7.04-6.92, 5.88-5.83 and 5.56-5.30 (br, 2H), 4.61-4.58 and 4.16-4.12 (m, 1H), 3.92 (t, J=6.6 Hz, 2H), 3.62-3.26 (m, 2H), 2.93 (t, J=7.8 Hz, 2H), 2.67-2.46 (m, 4H), 2.43-2.36 (m, 1H), 2.18-1.44 (m, 9H).

EXAMPLE 9-9

N,N-dimethyl-1-(3-{4-[(5-phenylpentyl)oxy]phenyl}propanoyl)-L-prolinamide

TLC: Rf 0.51 (chloroform:methanol=9:1);
MS (APCI, Pos. 40V): 437 (M+H)$^+$;
NMR: δ 7.30-7.07 (m, 7H), 6.83-6.78 (m, 2H), 4.88-4.84 and 4.41-4.37 (m, 1H), 3.92 (t, J=6.6 Hz, 2H), 3.69-3.59 and 3.46-3.37 (m, 2H), 3.14-2.84 (m, 8H), 2.70-2.48 (m, 4H), 2.33-2.01 (m, 2H), 1.96-1.64 (m, 6H), 1.54-1.44 (m, 2H).

EXAMPLE 9-10

N-(2-hydroxyethyl)-N-methyl-3-{4-[(5-phenylpentyl)oxy]phenyl}propanamide

TLC: Rf 0.50 (chloroform:methanol=9:1);
MS (APCI, Pos. 40V): 370 (M+H)$^+$;
NMR: δ 7.32-7.10 (m, 7H), 6.85-6.78 (m, 2H), 3.92 (t, J=6.4 Hz, 2H), 3.79-3.67 (m, 2H), 3.57-3.36 (m, 2H), 2.96-2.87 (m, 5H), 2.70-2.57 (m, 4H), 1.87-1.41 (m, 6H).

EXAMPLE 9-11

1-(3-{4-[(5-phenylpentyl)oxy]phenyl}propanoyl)pyrrolidin-3-ol

TLC: Rf 0.37 (chloroform:methanol=9:1);
MS (APCI, Pos. 40V): 382 (M+H)$^+$;
NMR: δ 7.32-7.08 (m, 7H), 6.84-6.77 (m, 2H), 4.50-4.41 (br, 1H), 3.92 (t, J=6.4 Hz, 2H), 3.71-3.24 (m, 4H), 2.91 (t, J=7.7 Hz, 2H), 2.68-2.46 (m, 4H), 2.04-1.41 (m, 8H).

EXAMPLE 9-12

3-{4-[(5-phenylpentyl)oxy]phenyl}-N-(tetrahydrofuran-2-ylmethyl)propanamide

TLC: Rf 0.22 (hexane:ethyl acetate=1:2);
MS (APCI, Pos. 40V): 396 (M+H)$^+$;
NMR: δ 7.32-7.08 (m, 7H), 6.80 (d, J=8.4 Hz, 2H), 5.77-5.65 (br, 1H), 3.95-3.48 (m, 6H), 3.18-3.05 (m, 1H), 2.90 (t, J=7.6 Hz, 2H), 2.64 (t, J=7.6 Hz, 2H), 2.48-2.40 (m, 2H), 2.00-1.39 (m, 10H).

EXAMPLE 9-13

3-{4-[(5-phenylpentyl)oxy]phenyl}-N-(pyridin-2-ylmethyl)propanamide

TLC: Rf 0.60 (chloroform:methanol=9:1);
MS (APCI, Pos. 40V): 403 (M+H)$^+$;
NMR: δ 8.51-8.49 (m, 1H), 7.62 (dt, J=7.8, 1.8 Hz, 1H), 7.31-7.08 (m, 9H), 6.78 (d, J=8.6 Hz, 2H), 6.71-6.58 (br, 1H), 4.53 (d, J=5.0 Hz, 2H), 3.90 (t, J=6.4 Hz, 2H), 2.94 (t, J=7.6 Hz, 2H), 2.64 (t, J=7.6 Hz, 2H), 2.54 (t, J=7.6 Hz, 2H), 1.87-1.41 (m, 6H).

EXAMPLE 9-14

N-(2-hydroxyethyl)-3-{4-[(5-phenylpentyl)oxy]phenyl}propanamide

TLC: Rf 0.49 (chloroform:methanol=9:1);
MS (APCI, Pos. 40V): 356 (M+H)$^+$;
NMR: δ 7.32-7.07 (m, 7H), 6.81 (d, J=8.6 Hz, 2H), 5.87-5.72 (br, 1H), 3.91 (t, J=6.4 Hz, 2H), 3.63 (t, J=4.4 Hz, 2H), 3.39-3.31 (m, 2H), 2.90 (t, J=7.6 Hz, 2H), 2.64 (t, J=7.6 Hz, 2H), 2.45 (t, J=7.6 Hz, 2H), 1.87-1.41 (m, 6H).

EXAMPLE 9-15

N-[2-(2-hydroxyethoxy)ethyl]-3-{4-[(5-phenylpentyl)oxy]phenyl}propanamide

TLC: Rf 0.50 (chloroform:methanol=9:1);
MS (APCI, Pos. 40V): 400 (M+H)$^+$;
NMR: δ 7.32-7.07 (m, 7H), 6.80 (d, J=8.6 Hz, 2H), 6.02-5.87 (br, 1H), 3.91 (t, J=6.4 Hz, 2H), 3.70 (t, J=4.4 Hz, 2H), 3.52-3.38 (m, 6H), 2.89 (t, J=7.8 Hz, 2H), 2.64 (t, J=7.6 Hz, 2H), 2.44 (t, J=7.8 Hz, 2H), 1.86-1.41 (m, 6H).

EXAMPLE 9-16

N-(3-hydroxy-4-methoxyphenyl)-3-{4-[(5-phenylpentyl)oxy]phenyl}propanamide

TLC: Rf 0.14 (hexane:ethyl acetate=2:1);
MS (APCI, Pos. 40V): 434 (M+H)$^+$;

NMR: δ 7.30-7.12 (m, 7H), 6.98-6.95 (m, 2H), 6.88-6.75 (m, 4H), 5.69 (s, 1H), 3.92 (t, J=6.6 Hz, 2H), 3.85 (s, 3H), 2.98 (t, J=7.5 Hz, 2H), 2.66-2.56 (m, 4H), 1.85-1.64 (m, 4H), 1.55-1.45 (m, 2H).

EXAMPLE 9-17

N-(3-hydroxyphenyl)-3-{4-[(5-phenylpentyl)oxy]phenyl}propanamide

TLC: Rf 0.21 (hexane:ethyl acetate=2:1);
MS (APCI, Pos. 40V): 404 (M+H)$^+$;
NMR: δ 7.82 (s, 1H), 7.76 (s, 1H), 7.30-7.07 (m, 9H), 6.84-6.79 (m, 2H), 6.63 (dd, J=8.1, 2.4 Hz, 1H), 6.43-6.40 (m, 1H), 3.92 (t, J=6.6 Hz, 2H), 2.99 (t, J=7.5 Hz, 2H), 2.64 (t, J=7.5 Hz, 4H), 1.84-1.64 (m, 4H), 1.55-1.45 (m, 2H).

EXAMPLE 9-18

N-(3-cyanophenyl)-3-{4-[(5-phenylpentyl)oxy]phenyl}propanamide

TLC: Rf 0.40 (hexane:ethyl acetate=2:1);
MS (APCI, Pos. 40V): 413 (M+H)$^+$;
NMR: δ 7.83 (s, 1H), 7.62-7.58 (m, 1H), 7.41-7.12 (m, 10H), 6.85-6.80 (m, 2H), 3.92 (t, J=6.6 Hz, 2H), 2.99 (t, J=7.5 Hz, 2H), 2.67-2.61 (m, 4H), 1.85-1.64 (m, 4H), 1.55-1.45 (m, 2H).

EXAMPLE 9-19

N-[4-chloro-3-(hydroxymethyl)phenyl]-3-{4-[(5-phenylpentyl)oxy]phenyl}propanamide TLC: Rf 0.62 (hexane:ethyl acetate=2:1);
MS (APCI, Pos., 40V): 452 (M+H)$^+$;
NMR (DMSO-d$_6$): δ 10.00 (s, 1H), 7.73 (d, J=2.7 Hz, 1H), 7.59 (dd, J=2.7, 9.0 Hz, 1H), 7.30-7.15 (m, 6H), 7.13 (d, J=8.7 Hz, 2H), 6.80 (d, J=8.7 Hz, 2H), 5.40 (t, J=5.7 Hz, 1H), 4.51 (d, J=5.7 Hz, 2H), 3.89 (t, J=6.6 Hz, 2H), 2.83 (t, J=6.6 Hz, 2H), 2.65-2.50 (m, 4H), 1.80-1.55 (m, 4H), 1.50-1.30 (m, 2H).

EXAMPLE 9-20

N-[3-(aminosulfonyl)phenyl]-3-{4-[(5-phenylpentyl)oxy]phenyl}propanamide

TLC: Rf 0.49 (chloroform:methanol=9:1);
MS (APCI, Pos. 40V): 467 (M+H)$^+$;
NMR (DMSO-d$_6$): δ 10.17 (s, 1H), 8.13 (s, 1H), 7.73-7.67 (m, 1H), 7.49-7.42 (m, 2H), 7.32 (s, 2H), 7.27-7.10 (m, 6H), 6.80 (d, J=8.4 Hz, 2H), 3.88 (t, J=6.6 Hz, 2H), 2.82 (t, J=7.5 Hz, 2H), 2.61-2.54 (m, 4H), 1.74-1.54 (m, 4H), 1.44-1.34 (m, 2H).

EXAMPLE 9-21

N-(4-chloro-3-cyanophenyl)-3-{4-[(5-phenylpentyl)oxy]phenyl}propanamide

TLC: Rf 0.23 (hexane:ethyl acetate=3:1);
MS (APCI, Pos. 40V): 447 (M+H)$^+$;
NMR: δ 7.85 (d, J=2.4 Hz, 1H), 7.55 (dd, J=8.7, 2.4 Hz, 1H), 7.39 (d, J=8.7 Hz, 1H), 7.30-7.11 (m, 8H), 6.85-6.80 (m, 2H), 3.92 (t, J=6.6 Hz, 2H), 2.98 (t, J=7.5 Hz, 2H), 2.67-2.61 (m, 4H), 1.85-1.64 (m, 4H), 1.55-1.44 (m, 2H).

EXAMPLE 9-22

N-{3-[(1E)-N-hydroxyethanimidoyl]phenyl}-3-{4-[(5-phenylpentyl)oxy]phenyl}propanamide TLC: Rf 0.24 (hexane:ethyl acetate=2:1);
MS (APCI, Pos. 40V): 445 (M+H)$^+$;
NMR (DMSO-d$_6$): δ 11.17 (s, 1H), 9.92 (s, 1H), 7.89 (d, J=1.2 Hz, 1H), 7.60-7.54 (m, 1H), 7.30-7.09 (m, 9H), 6.82-6.77 (m, 2H), 3.88 (t, J=6.6 Hz, 2H), 2.82 (t, J=7.5 Hz, 2H), 2.59-2.53 (m, 4H), 2.10 (s, 3H), 1.73-1.54 (m, 4H), 1.44-1.34 (m, 2H).

EXAMPLE 9-23

[(2S)-1-(3-{4-[(5-phenylpentyl)oxy]phenyl}propanoyl)pyrrolidin-2-yl]methanol

TLC: Rf 0.30 (hexane:ethyl acetate=1:3);
NMR: δ 7.32-7.09 (m, 7H), 6.85-6.78 (m, 2H), 4.27-4.15 (m, 1H), 3.92 (t, J=6.4 Hz, 2H), 3.65 (dd, J=11.4, 3.0 Hz, 1H), 3.55 (dd, J=11.2, 8.0 Hz, 1H), 3.45-3.23 (m, 2H), 2.93 (t, J=8.2 Hz, 2H), 2.68-2.53 (m, 4H), 2.08-1.42 (m, 10H).

EXAMPLE 9-24

[(2R)-1-(3-{4-[(5-phenylpentyl)oxy]phenyl}propanoyl)pyrrolidin-2-yl]methanol

TLC: Rf 0.32 (hexane:ethyl acetate=1:3);
NMR: δ 7.32-7.09 (m, 7H), 6.85-6.78 (m, 2H), 4.27-4.15 (m, 1H), 3.92 (t, J=6.4 Hz, 2H), 3.65 (dd, J=11.4, 3.0 Hz, 1H), 3.55 (dd, J=11.4, 8.0 Hz, 1H), 3.45-3.23 (m, 2H), 2.93 (t, J=8.2 Hz, 2H), 2.68-2.53 (m, 4H), 2.08-1.41 (m, 10H).

EXAMPLE 10-1 TO EXAMPLE 10-2

The procedure of Example 9 was followed but using a corresponding sulfonic acid compound as a substitute for 4-(4-phenylbutoxy)cinnamic acid while using a corresponding amine compound as a substitute for (2S)-prolinol. Thus, the compound of the present invention having the following physical properties was obtained.

EXAMPLE 10-1

{(2S)-1-[2-{4-[(5-phenylpentyl)oxy]phenyl}ethyl)sulfonyl]pyrrolidin-2-yl]methanol TLC: Rf 0.35 (hexane:ethyl acetate=1:1);
MS (MALDI, Pos.): 470 (M+K)$^+$, 454 (M+Na)$^+$, 432 (M+H)$^+$;
NMR: δ 7.30-7.10 (m, 7H), 6.84 (m, 2H), 3.93 (t, J=6.6 Hz, 2H), 3.87 (m, 1H), 3.72-3.56 (m, 2H), 3.50-3.34 (m, 2H), 3.24-3.16 (m, 2H), 3.14-3.04 (m, 2H), 2.64 (t, J=7.5 Hz, 2H), 2.48 (br, 1H), 2.08-1.64 (m, 8H), 1.52 (m, 2H).

EXAMPLE 10-2

2-({(2S)-2-[(benzyloxy)methyl]pyrrolidin-1-yl}sulfonyl)-1-{4-[(5-phenylpentyl)oxy]phenyl}ethanol TLC: Rf 0.45 (hexane:ethyl acetate=3:2);
MS (MALDI, Pos.): 576 (M+K)$^+$, 560 (M+Na)$^+$;

NMR: δ 7.36-7.16 (m, 12H), 6.88-6.84 (m, 2H), 5.25-5.16 (m, 1H), 4.61-4.49 (m, 2H), 4.16-4.08 (m, 1H), 3.94 (t, J=6.6 Hz, 2H), 3.64-3.16 (m, 6H), 2.64 (t, J=7.5 Hz, 2H), 2.06-1.62 (m, 8H), 1.54-1.46 (m, 2H).

EXAMPLE 11

7-(benzyloxy)-4-methyl-1,2-dihydronaphthalene

Procedure (1):

To a solution of 6-hydroxy-3,4-dihydronaphthalen-1(2H)-one (24.3 g) in acetone (160 mL), benzyl bromide (29.4 mL) and potassium carbonate (31.1 g) were added at room temperature, followed by stirring at 40° C. for 3.5 hours. After filtering off the insoluble matters and concentrating the filtrate, the residue was washed with a mixed solvent of tert-butyl methyl ether-hexane (1:4) to thereby give 6-(benzyloxy)-3,4-dihydronaphthalen-1(2H)-one (34.5 g).

Procedure (2):

To a solution of the obtained 6-(benzyloxy)-3,4-dihydronaphthalen-1(2H)-one (34.5 g) in tetrahydrofuran (300 mL), methyl magnesium bromide (3M diethyl ether solution, 55 mL) was added at 0° C., followed by stirring at room temperature for 1 hour. The reaction mixture was cooled to 0° C. and poured into ice-saturated aqueous ammonium chloride solution. After adding 2N hydrochloric acid, the mixture was stirred at room temperature for 3 hours. Then, the resultant was extracted with ethyl acetate and the organic layer was successively washed with water and brine, dried and concentrated. The obtained residue was purified by silica gel column chromatography (hexane:ethyl acetate=10:1) to thereby give the title compound (24.8 g) having the following physical properties.

TLC: Rf 0.71 (hexane:ethyl acetate=3:1);
MS: 251 (M+H)$^+$;
NMR: δ 7.26-7.49 (m, 5H), 7.09-7.21 (m, 1H), 6.67-6.90 (m, 2H), 5.60-5.81 (m, 1H), 5.07 (s, 2H), 2.74 (t, J=7.96 Hz, 2H), 2.17-2.31 (m, 2H), 1.94-2.08 (m, 3H).

EXAMPLE 12

6-(benzyloxy)-1-methyl-3,4-dihydro-2-naphthalenecarbaldehyde

To phosphorus oxychloride (26.7 g), N,N-dimethylformamide (60 mL) was dropped at 0° C., followed by stirring for 20 minutes. Then, a solution of the compound (24.8 g) prepared in Example 11 in dichloromethane (60 mL) was slowly dropped thereto, followed by stirring at room temperature for 90 minutes. The reaction mixture was cooled to 0° C., poured into ice and then allowed to stand for a while. Next, the resultant was extracted with a mixed solvent of hexane-ethyl acetate (1:2). The organic layer was successively washed with water and brine, dried and concentrated. The obtained solid was washed with tert-butyl methyl ether to thereby give the title compound (19.9 g) having the following physical properties.

TLC: Rf 0.50 (hexane:ethyl acetate=3:1);
MS: 279 (M+H)$^+$;
NMR: δ 10.31 (s, 1H), 7.29-7.62 (m, 6H), 6.70-6.98 (m, 2H), 5.11 (s, 2H), 2.63-2.80 (m, 2H), 2.38-2.61 (m, 5H).

EXAMPLE 13

6-hydroxy-1-methyl-3,4-dihydro-2-naphthalenecarbaldehyde

To thioanisole (35 mL), trifluoroacetic acid (140 mL) was added at 0° C. Then, the compound (9.17 g) prepared in Example 12 was added in portions thereto, followed by stirring at room temperature for 4 hours. The reaction mixture was poured into ice, followed by adding a 5N aqueous sodium hydroxide solution. After washing with tert-butyl methyl ether, 1N hydrochloric acid was added to the aqueous layer, followed by extracting with ethyl acetate. The organic layer was dried and concentrated. The obtained residue was purified by silica gel column chromatography (hexane:ethyl acetate=5:1 to 2:1) to thereby give the title compound (6.03 g) having the following physical properties.

TLC: Rf 0.26 (hexane:ethyl acetate=3:1);
MS: 189 (M+H)$^+$;
NMR: δ 10.31 (s, 1H), 7.45 (d, J=8.4 Hz, 1H), 6.76 (dd, J=8.4, 2.6 Hz, 1H), 6.70 (d, J=2.6 Hz, 1H), 2.66-2.75 (m, 2H), 2.50 (s, 3H), 2.46-2.55 (m, 2H).

EXAMPLE 14

6-[3-(4-fluorophenyl)propoxy]-1-methyl-3,4-dihydro-2-naphthalenecarbaldehyde

The procedure (1) of Example 1 was followed but using the compound prepared in Example 13 as a substitute for 6-hydroxy-3,4-dihydronaphthalen-1(2H)-one while using 1-bromo-3-(4-fluorophenyl)propane as a substitute for benzyl bromide to thereby give the title compound having the following physical properties.

TLC: Rf 0.40 (hexane:ethyl acetate=3:1);
MS (EI, Pos.): 324 (M$^+$), 109;
NMR: δ 10.32 (s, 1H), 7.48 (d, J=8.50 Hz, if), 7.16 (dd, J=8.50, 5.50 Hz, 2H), 6.97 (t, J=8.50 Hz, 2H), 6.78 (dd, J=8.50, 2.50 Hz, 1H), 6.73 (d, J=2.50 Hz, 1H), 3.99 (t, J=6.00 Hz, 2H), 2.79 (t, J=7.50 Hz, 2H), 2.69-2.75 (m, 2H), 2.47-2.56 (m, 5H), 2.04-2.14 (m, 2H).

EXAMPLE 15

N-({6-[3-(4-fluorophenyl)propoxy]-1-methyl-3,4-dihydro-2-naphthalenyl}methyl)ethanamine The procedure of Example 5 was followed but using the compound prepared in Example 14 as a substitute for 6-(4-(phenylbutoxy)-2-formylnaphthalene while using ethylamine as a substitute for piperidine. Thus, the compound of the present invention having the following physical properties was obtained.

TLC: Rf 0.23 (chloroform:methanol:aqueous ammonia=80:10:1);
MS: 821 (2M+CF$_3$CO$_2$H+H)$^+$, 707 (2M+H)$^+$, 354 (M+H)$^+$, 352, 309, 156;
NMR (CD$_3$OD): δ 7.15-7.24 (m, 3H), 6.92-7.02 (m, 2H), 6.64-6.73 (m, 2H), 3.93 (t, J=6.13 Hz, 2H), 3.43 (s, 2H), 2.62-2.83 (m, 6H), 2.21-2.32 (m, 2H), 2.06 (s, 3H), 1.97-2.09 (m, 2H), 1.16 (t, J=7.14 Hz, 3H).

EXAMPLE 16

(4R)-4-benzyl-3-propionyl-1,3-oxazolidin-2-one

To a solution of (4R)-4-benzyl-1,3-oxazolidin-2-one (60 g) in tetrahydrofuran (600 mL), n-butyllithium-hexane solution (1.54M, 230 mL) was slowly dropped at −78° C., followed by stirring for 30 minutes. Then, propionyl chloride (30.9 mL) was added in portions thereto, followed by stirring for 30 minutes. The reaction mixture was added with water and was raised to room temperature. Then, the mixture was extracted with ethyl acetate. The organic layer was successively washed with water and brine, dried and concentrated. Thus, the title compound (79.4 g) having the following physical properties was obtained.

TLC: Rf 0.52 (hexane:ethyl acetate=3:1);
NMR: δ 7.13-7.42 (m, 5H), 4.60-4.76 (m, 1H), 4.08-4.30 (m, 2H), 3.31 (dd, J=13.20, 3.20 Hz, 1H), 2.86-3.09 (m, 2H), 2.77 (dd, J=13.20, 9.70 Hz, 1H), 1.21 (t, J=7.30 Hz, 3H).

EXAMPLE 17

(4R)-4-benzyl-3-[(2S)-3-(4-chlorophenyl)-2-methyl-propanoyl]-1,3-oxazolidin-2-one To a solution of the compound (10 g) prepared in Example 16 in tetrahydrofuran (80 mL), a solution of sodium hexamethyldisilazide in tetrahydrofuran (1M, 49.3 mL) was dropped at −78° C., followed by stirring for 1 hour. Then, chlorobenzyl bromide (10.6 g) was dropped thereto, followed by stirring at −78° C. for 7 hours. The reaction mixture was added with a saturated aqueous ammonium chloride solution and the mixture was extracted with ethyl acetate. The organic layer was washed with brine, dried and concentrated. Then, the obtained solid was washed with hexane to thereby give the title compound (12.8 g) having the following physical properties.

TLC: Rf 0.57 (toluene:acetone=20:1);
MS: 360, 358 (M+H)$^+$, 178;
NMR: δ 7.13-7.40 (m, 7H), 6.97-7.16 (m, 2H), 4.56-4.79 (m, 1H), 4.00-4.25 (m, 3H), 3.05-3.18 (m, 2H), 2.52-2.69 (m, 2H), 1.18 (d, J=6.8 Hz, 3H).

EXAMPLE 18

(2S)-3-(4-chlorophenyl)-2-methyl-1-propanol

To a solution of the lithium borohydride (1.35 g) in tetrahydrofuran (30 mL), a solution of the compound (10.1 g) prepared in Example 17 in tetrahydrofuran (100 mL) was dropped at 0° C., followed by stirring for 4 hours. The reaction mixture was added with a 1N aqueous sodium hydroxide solution and the mixture was extracted with ethyl acetate. The organic layer was washed with brine. After drying, the solvent was concentrated. Then, the obtained residue was purified by silica gel column chromatography (hexane:ethyl acetate=3:1) to thereby give the title compound (4.80 g) having the following physical properties.

TLC: Rf 0.37 (hexane:ethyl acetate=3:1);
MS (EI, Pos.): 186, 184 (M+H)$^+$, 168, 166, 153, 151, 131, 125;
NMR: δ 7.25 (d, J=8.8 Hz, 2H), 7.10 (d, J=8.8 Hz, 2H), 3.43-3.57 (m, 2H), 2.75 (dd, J=13.5, 6.1 Hz, 1H), 2.39 (dd, J=13.5, 8.1 Hz, 1H), 1.82-2.00 (m, 1H), 1.30 (t, J=5.5 Hz, 1H), 0.90 (d, J=6.8 Hz, 3H).

EXAMPLE 19

6-{[(2S)-3-(4-chlorophenyl)-2-methylpropyl]oxy}-1-methyl-3,4-dihydro-2-naphthalenecarbaldehyde To a solution of the compound (2.00 g) prepared in Example 18, the compound (2.03 g) prepared in Example 13, and triphenylphosphine (3.38 g) in tetrahydrofuran (35 mL), 1,1'-azobis (N,N-dimethylformamide) (2.23 g) was added at 0° C., followed by stirring at room temperature for 12 hours. After filtering off the insoluble matters, the filtrate was concentrated. Then, the obtained residue was purified by silica gel column chromatography (hexane:ethyl acetate=4:1 to 3:1) to thereby give the title compound (3.90 g) having the following physical properties.

TLC: Rf 0.33 (hexane:ethyl acetate=3:1);
MS: 357, 355 (M+H)$^+$;
NMR: δ 10.32 (s, 1H), 7.47 (d, J=8.6 Hz, 1H), 7.25 (d, J=8.4 Hz, 2H), 7.10 (d, J=8.4 Hz, 2H), 6.77 (dd, J=8.6, 2.7 Hz, 1H), 6.73 (d, J=2.7 Hz, 1H), 3.80 (d, J=5.8 Hz, 2H), 2.84 (dd, J=13.1, 6.7 Hz, 1H), 2.66-2.77 (m, 2H), 2.44-2.62 (m, 6H), 2.14-2.32 (m, 1H), 1.02 (d, J=6.8 Hz, 3H).

EXAMPLE 20 methyl 3-[({6-[(2S)-3-(4-chlorophenyl)-2-methyl-propoxy]-1-methyl-3,4-dihydro-2-naphthalenyl}methyl)amino]propanoate The procedure of Example 5 was followed but using the compound prepared in Example 19 as a substitute for 6-(4-(phenylbutoxy)-2-formylnaphthalene while using β-alanine methyl ester as a substitute for piperidine. Thus, the compound of the present invention having the following physical properties was obtained.

TLC: Rf 0.62 (chloroform:methanol:aqueous ammonia=80:10:1)

EXAMPLE 21 methyl 3-{(t-butoxycarbonyl)[(6-{[(2S)-3-(4-chlorophenyl)-2-methylpropyl]oxy}-1-methyl-3,4-dihydro-2-naphthalenyl)methyl]amino}propanoate To a suspension of the compound (300 mg) prepared in Example 20 in dichloromethane (3 mL), triethylamine (0.15 mL) and di-t-butyl dicarbonate (Boc$_2$O) (192 mg) were added, followed by stirring at room temperature for 1 hour. The reaction mixture was added with a saturated aqueous sodium hydrogen carbonate solution and the mixture was extracted with dichloromethane. The organic layer was dried and concentrated. Then, the obtained residue was purified by silica gel column chromatography (hexane:ethyl acetate=8:1 to 6:1) to thereby give the compound of the present invention (295 mg) having the following physical properties.

TLC: Rf 0.37 (hexane:ethyl acetate=6:1);
MS: 544, 542 (M+H)$^+$, 488, 486, 341, 339;
NMR: δ 7.24 (d, J=8.2 Hz, 2H), 7.20 (d, J=8.4 Hz, 1H), 7.11 (d, J=8.2 Hz, 2H), 6.65-6.74 (m, 2H), 4.13-4.23 (m, 2H), 3.76 (d, J=5.9 Hz, 2H), 3.66 (s, 3H), 3.33-3.50 (m, 2H), 2.85 (dd, J=13.5, 6.4 Hz, 1H), 2.68 (t, J=7.0 Hz, 2H), 2.46-2.64 (m, 3H), 2.11-2.29 (m, 3H), 2.08 (s, 3H), 1.48 (s, 9H), 1.00 (d, J=6.8 Hz, 3H).

EXAMPLE 22

3-{(t-butoxycarbonyl)[6-{[(2S)-3-(4-chlorophenyl)-2-methylpropyl]oxy}-1-methyl-3,4-dihydro-2-naphthalenyl)methyl]amino}propanoic acid To a solution of the compound (295 mg) prepared in Example 21 in tetrahydrofuran (2 mL), methanol (4 mL) and a 5N aqueous sodium hydroxide solution (2 mL) were added, followed by stirring at room temperature for 1 hour. The reaction mixture was added with 1N hydrochloric acid and the mixture was extracted with ethyl acetate. The organic layer was dried and then concentrated to thereby give the compound of the present invention (280 mg) having the following physical properties.

TLC: Rf 0.20 (hexane:ethyl acetate=2:1);

MS: 530, 529 (M+H)⁺, 474, 472, 341, 339;

NMR: δ 7.24 (d, J=8.4 Hz, 2H), 7.19 (d, J=8.4 Hz, 1H), 7.10 (d, J=8.4 Hz, 2H), 6.64-6.74 (m, 2H), 4.18 (s, 2H), 3.76 (d, J=5.9 Hz, 2H), 3.36-3.48 (m, 2H), 2.85 (dd, J=13.4, 6.6 Hz, 1H), 2.58-2.74 (m, 4H), 2.52 (dd, J=13.4, 7.5 Hz, 1H), 2.11-2.28 (m, 3H), 2.05 (s, 3H), 1.48 (s, 9H), 1.00 (d, J=6.8 Hz, 3H).

EXAMPLE 23

N-(3-{[(6-{[(2S)-3-(4-chlorophenyl)-2-methylpropyl]oxy}-1-methyl-3,4-dihydro-2-naphthalenyl)methyl]amino}propanoyl)methanesulfonamide The procedure of Example 4 was followed but using the compound prepared in Example 22 as a substitute for the compound prepared in Example 3 while using methanesulfonamide as a substitute for benzenesulfonamide. Thus, the compound of the present invention having the following physical properties was obtained.

TLC: Rf 0.42 (chloroform:methanol:aqueous ammonia=80:20:4);

MS (FAB, Neg.): 505, 503 (4-H)⁻;

NMR (CD₃OD): δ 7.29 (d, J=8.4 Hz, 1H), 7.24 (d, J=8.4 Hz, 2H), 7.16 (d, J=8.4 Hz, 2H), 6.67-6.77 (m, 2H), 3.90 (s, 2H), 3.78 (d, J=5.9 Hz, 2H), 3.22 (t, J=6.1 Hz, 2H), 3.00 (s, 3H), 2.84 (dd, J=13.5, 6.5 Hz, 1H), 2.71-2.80 (m, 2H), 2.48-2.62 (m, 3H), 2.30-2.40 (m, 2H), 2.10-2.25 (m, 4H), 1.00 (d, J=6.8 Hz, 3H).

EXAMPLE 23-1 TO EXAMPLE 23-2

The procedure of Example 23 was followed but using a corresponding sulfonamide as a substitute for methanesulfonamide. Thus, the compound of the present invention having the following physical properties was obtained.

EXAMPLE 23-1

N-(3-{(6-{[(2S)-3-(4-chlorophenyl)-2-methylpropyl]oxy}-1-methyl-3,4-dihydro-2-naphthalenyl)methyl]amino}propanoyl)benzenesulfonamide TLC: Rf 0.52 (chloroform:methanol:aqueous ammonia=80:20:4);

MS (FAB, Pos.): 569, 567 (M+H)⁺, 341, 339;

NMR (CD₃OD): δ 7.90 (dd, J=8.1, 1.6 Hz, 2H), 7.37-7.51 (m, 3H), 7.21-7.31 (m, 3H), 7.16 (d, J=8.4 Hz, 2H), 6.74 (dd, J=8.8, 2.7 Hz, 1H), 6.70 (d, J=2.7 Hz, 1H), 3.84 (s, 2H), 3.79 (d, J=5.9 Hz, 2H), 3.16 (t, J=6.1 Hz, 2H), 2.80-2.89 (m, 1H), 2.73 (t, J=7.3 Hz, 2H), 2.52-2.60 (m, 1H), 2.49 (t, J=6.1 Hz, 2H), 2.26-2.36 (m, 2H), 2.13-2.25 (m, 1H), 2.12 (s, 3H), 1.01 (d, J=6.8 Hz, 3H).

EXAMPLE 23-2

N-(3-{[(6-{[(2S)-3-(4-chlorophenyl)-2-methylpropyl]oxy}-1-methyl-3,4-dihydro-2-naphthalenyl)methyl]amino}propanoyl)-3,5-dimethyl-4-isoxazolesulfonamide TLC: Rf 0.50 (chloroform:methanol:aqueous ammonia=80:20:4);

MS (FAB, Neg.): 586, 584 (M−H)⁻;

NMR (CD₃OD): δ 7.29 (d, J=8.6 Hz, 1H), 7.24 (d, J=8.4 Hz, 2H), 7.15 (d, J=8.4 Hz, 2H), 6.67-6.78 (m, 2H), 3.88 (s, 2H), 3.79 (d, J=5.9 Hz, 2H), 3.18 (t, J=6.1 Hz, 2H), 2.84 (dd, J=13.4, 6.6 Hz, 1H), 2.70-2.79 (m, 2H), 2.54-2.62 (m, 4H), 2.51 (t, J=6.1 Hz, 2H), 2.25-2.39 (m, 5H), 2.07-2.26 (m, 4H), 1.00 (d, J=6.8 Hz, 3H).

EXAMPLE 24

6-{[(2S)-3-(4-fluorophenyl)-2-methylpropyl]oxy}-1-methyl-3,4-dihydro-2-naphthalenecarbaldehyde The procedures of Example 17, Example 18, and Example 19 were followed but using 4-fluorobenzyl bromide as a substitute for 4-chlorobenzyl bromide. Thus, the title compound having the following physical properties was obtained.

TLC: Rf 0.86 (hexane:ethyl acetate=1:1);

MS: 339 (M+H)⁺;

NMR: δ 10.32 (s, 1H), 7.47 (d, J=8.42 Hz, 1H), 7.07-7.16 (m, 2H), 6.90-7.02 (m, 2H), 6.77 (dd, J=8.42, 2.56 Hz, 1H), 6.73 (d, J=2.56 Hz, 1H), 3.80 (d, J=5.85 Hz, 2H), 2.84 (dd, J=13.63, 6.50 Hz, 1H), 2.67-2.76 (m, 2H), 2.50 (s, 3H), 2.41-2.62 (m, 3H), 2.09-2.33 (m, 1H), 1.02 (d, J=6.77 Hz, 3H).

EXAMPLE 25

N-[6-{[(2S)-3-(4-fluorophenyl)-2-methylpropyl]oxy}-1-methyl-3,4-dihydro-2-naphthalenyl)methyl]ethanamine The procedure of Example 5 was followed but using the compound prepared in Example 24 as a substitute for 6-(4-phenylbutoxy)-2-formylnaphthalene while using ethylamine as a substitute for piperidine. Thus, the compound of the present invention having the following physical properties was obtained.

TLC: Rf 0.34 (chloroform:methanol:aqueous ammonia=80:10:1);

MS: 849 (2M+CF₃CO₂H+H)⁺, 735 (2M+H)⁺, 368 (M+H)⁺, 366, 356, 323;

NMR (CD₃OD): δ 7.13-7.23 (m, 3H), 6.92-7.02 (m, 2H), 6.65-6.73 (m, 2H), 3.77 (d, J=6.04 Hz, 2H), 3.46 (s, 2H), 2.84 (dd, J=13.36, 6.40 Hz, 1H), 2.65-2.73 (m, 2H), 2.70 (q, J=7.23 Hz, 2H), 2.54 (dd, J=13.36, 7.68 Hz, 1H), 2.09-2.31 (m, 3H), 2.06 (t, J=1.46 Hz, 3H), 1.16 (t, J=7.23 Hz, 3H), 1.00 (d, J=6.77 Hz, 3H).

EXAMPLE 25-1 TO EXAMPLE 25-10

The procedure of Example 25 was followed but using a corresponding amine compound as a substitute for ethylamine. Thus, the compound of the present invention having the following physical properties was obtained.

EXAMPLE 25-1

1-(6-{[(2S)-3-(4-fluorophenyl)-2-methylpropyl]oxy}-1-methyl-3,4-dihydro-2-naphthalenyl)-N,N-dimethylmethanamine TLC: Rf 0.44 (chloroform:methanol:aqueous ammonia=80:10:1);

MS: 849 (2M+CF₃CO₂H+H)⁺, 368 (M+H)⁺, 323;

NMR (CD₃OD): δ 7.08-7.25 (m, 3H), 6.90-7.03 (m, 2H), 6.61-6.74 (m, 2H), 3.76 (d, J=5.85 Hz, 2H), 3.15 (s, 2H), 2.83 (dd, J=13.36, 6.40 Hz, 1H), 2.61-2.73 (m, 2H), 2.53 (dd, J=13.36, 7.87 Hz, 1H), 2.27 (s, 6H), 2.09-2.30 (m, 3H), 2.05 (s, 3H), 0.99 (d, J=6.77 Hz, 3H).

EXAMPLE 25-2

1-[(6-{[(2S)-3-(4-fluorophenyl)-2-methylpropyl]oxy}-1-methyl-3,4-dihydro-2-naphthalenyl)methyl]azetidine TLC: Rf 0.37 (chloroform:methanol:aqueous ammonia=80:10:1);
MS: 873 (2M+CF$_3$CO$_2$H+H)$^+$, 380 (M+H)$^+$, 368, 323;
NMR (CD$_3$OD): δ 7.13-7.23 (m, 3H), 6.93-7.01 (m, 2H), 6.64-6.72 (m, 2H), 3.76 (d, J=6.40 Hz, 2H), 3.34-3.42 (m, 6H), 2.84 (dd, J=13.54, 6.59 Hz, 1H), 2.61-2.69 (m, 2H), 2.54 (dd, J=13.54, 7.68 Hz, 1H), 2.10-2.26 (m, 4H), 2.09 (t, J=1.56 Hz, 3H), 0.99 (d, J=6.77 Hz, 3H).

EXAMPLE 25-3

1-[(6-{[(2S)-3-(4-fluorophenyl)-2-methylpropyl]oxy}-1-methyl-3,4-dihydro-2-naphthalenyl)methyl]pyrrolidine TLC: Rf 0.44 (chloroform:methanol:aqueous ammonia=80:10:1);
MS: 901 (2M+CF$_3$CO$_2$H+H)$^+$, 823, 394 (M+H)$^+$, 323;
NMR (CD$_3$OD): δ 7.11-7.23 (m, 3H), 6.88-7.05 (m, 2H), 6.61-6.75 (m, 2H), 3.76 (d, J=5.49 Hz, 2H), 3.41 (s, 2H), 2.47-2.90 (m, 8H), 2.08 (s, 3H), 2.01-2.36 (m, 3H), 1.77-1.92 (m, 4H), 0.99 (d, J=6.77 Hz, 3H).

EXAMPLE 25-4

(3R)-1-[(6-{[(2S)-3-(4-fluorophenyl)-2-methylpropyl]oxy}-1-methyl-3,4-dihydro-2-naphthalenyl)methyl]-3-pyrrolidinol TLC: Rf 0.31 (chloroform:methanol:aqueous ammonia=80:10:1);
MS: 933 (2M+CF$_3$CO$_2$H+H)$^+$, 410 (M+H)$^+$, 323;
NMR (CD$_3$OD): δ 7.13-7.23 (m, 3H), 6.93-7.02 (m, 2H), 6.65-6.73 (m, 2H), 4.31-4.39 (m, 1H), 3.77 (d, J=6.22 Hz, 2H), 3.34 (s, 2H), 2.48-2.93 (m, 8H), 2.24-2.35 (m, 2H), 2.10-2.24 (m, 2H), 2.07 (t, J=1.46 Hz, 3H), 1.66-1.78 (m, 1H), 1.00 (d, J=6.77 Hz, 3H).

EXAMPLE 25-5

(3S)-1-[(6-{[(2S)-3-(4-fluorophenyl)-2-methylpropyl]oxy}-1-methyl-3,4-dihydro-2-naphthalenyl)methyl]-3-pyrrolidinol TLC: Rf 0.31 (chloroform:methanol:aqueous ammonia=80:10:1);
MS: 933 (2M+CF$_3$CO$_2$H+H)$^+$, 410 (M+H)$^+$, 323;
NMR (CD$_3$OD): δ 7.13-7.22 (m, 3H), 6.92-7.01 (m, 2H), 6.64-6.72 (m, 2H), 4.31-4.39 (m, 1H), 3.77 (d, J=5.67 Hz, 2H), 3.36 (s, 2H), 2.49-2.94 (m, 8H), 2.25-2.35 (m, 2H), 2.09-2.24 (m, 2H), 2.08 (s, 3H), 1.65-1.80 (m, 1H), 1.00 (d, J=6.77 Hz, 3H).

EXAMPLE 25-6 t-butyl {1-[(6-{[(2S)-3-(4-fluorophenyl)-2-methylpropyl]oxy}-1-methyl-3,4-dihydro-2-naphthalenyl)methyl]-3-pyrrolidinyl}carbamate TLC: Rf 0.45 (chloroform:methanol:aqueous ammonia=80:10:1);
MS: 509 (M+H)$^+$, 497, 323, 187;
NMR: δ 7.08-7.21 (m, 3H), 6.92-7.01 (m, 2H), 6.66-6.73 (m, 2H), 4.73-4.94 (m, 1H), 4.08-4.23 (m, 1H), 3.76 (d, J=6.04 Hz, 2H), 3.23 (s, 2H), 2.45-2.92 (m, 6H), 2.11-2.39 (m, 4H), 2.05 (s, 3H), 1.54-1.69 (m, 2H), 1.43 (s, 9H), 1.00 (d, J=6.77 Hz, 3H).

EXAMPLE 25-7

{(2S)-1-[(6-{[(2S)-3-(4-fluorophenyl)-2-methylpropyl]oxy}-1-methyl-3,4-dihydro-2-naphthalenyl)methyl]-2-pyrrolidinyl}methanol TLC: Rf 0.43 (chloroform:methanol:aqueous ammonia=80:10:1);
MS: 424 (M+H)$^+$, 323, 114;
NMR (CD$_3$OD): δ 7.11-7.24 (m, 3H), 6.91-7.04 (m, 2H), 6.63-6.74 (m, 2H), 3.76 (d, J=5.85 Hz, 1H), 3.45-3.65 (m, 3H), 3.20-3.26 (m, 1H), 3.02-3.12 (m, 1H), 2.84 (dd, J=13.45, 6.31 Hz, 1H), 2.61-2.76 (m, 3H), 2.53 (dd, J=13.45, 7.87 Hz, 1H), 2.08 (s, 3H), 1.91-2.45 (m, 6H), 1.63-1.81 (m, 3H), 0.99 (d, J=6.77 Hz, 3H).

EXAMPLE 25-8

{(2R)-1-[(6-{[(2S)-3-(4-fluorophenyl)-2-methylpropyl]oxy}-1-methyl-3,4-dihydro-2-naphthalenyl)methyl]-2-pyrrolidinyl}methanol TLC: Rf 0.43 (chloroform:methanol:aqueous ammonia=80:10:1);
MS: 424 (M+H)$^+$, 323, 114;
NMR (CD$_3$OD): δ 7.10-7.24 (m, 3H), 6.89-7.03 (m, 2H), 6.61-6.74 (m, 2H), 3.77 (d, J=6.04 Hz, 2H), 3.45-3.67 (m, 3H), 3.03-3.13 (m, 1H), 2.84 (dd, J=13.45, 6.50 Hz, 1H), 2.63-2.77 (m, 3H), 2.54 (dd, J=13.45, 7.50 Hz, 1H), 2.09 (s, 3H), 1.91-2.48 (m, 6H), 1.64-1.82 (m, 3H), 1.00 (d, J=6.77 Hz, 3H).

EXAMPLE 25-9

(2S)-1-[(6-{[(2S)-3-(4-fluorophenyl)-2-methylpropyl]oxy}-1-methyl-3,4-dihydro-2-naphthalenyl)methyl]-2-(1-pyrrolidinylmethyl)pyrrolidine TLC: Rf 0.45 (chloroform:methanol:aqueous ammonia=80:10:1);
MS: 477 (M+H)$^+$, 323;
NMR (CD$_3$OD): δ 7.13-7.21 (m, 3H), 6.92-7.01 (m, 2H), 6.64-6.72 (m, 2H), 3.76 (d, J=5.85 Hz, 2H), 3.63 (d, J=12.44 Hz, 1H), 3.30 (s, 2H), 3.22 (d, J=12.26 Hz, 1H), 3.01-3.13 (m, 1H), 2.09 (s, 3H), 2.00-2.89 (m, 14H), 1.59-1.88 (m, 7H), 0.99 (d, J=6.77 Hz, 3H).

EXAMPLE 25-10

1-[(6-{[(2S)-3-(4-fluorophenyl)-2-methylpropyl]oxy}-1-methyl-3,4-dihydro-2-naphthalenyl)methyl]-4-methyl-1,4-diazepane TLC: Rf 0.32 (chloroform:methanol:aqueous ammonia=80:10:1);
MS: 987 (2M+CF$_3$CO$_2$H+H)$^+$, 437 (M+H)$^+$, 323, 115;
NMR (CD$_3$OD): δ 7.09-7.22 (m, 3H), 6.89-7.04 (m, 2H), 6.60-6.74 (m, 2H), 3.76 (d, J=6.40 Hz, 2H), 3.27 (s, 2H), 2.71-2.88 (m, 9H), 2.60-2.68 (m, 2H), 2.53 (dd, J=13.54, 7.87

Hz, 1H), 2.45 (s, 3H), 2.23-2.34 (m, 2H), 2.09-2.22 (m, 1H), 2.04 (s, 3H), 1.82-1.93 (m, 2H), 0.99 (d, J=6.77 Hz, 3H).

EXAMPLE 26

6-{[(2R)-3-(4-fluorophenyl)-2-methylpropyl]oxy}-1-methyl-3,4-dihydro-2-naphthalenecarbaldehyde The procedures of Example 16 to Example 24 were followed but using (4S)-4-benzyl-1,3-oxazolidin-2-one as a substitute for (4R)-4-benzyl-1,3-oxazolidin-2-one. Thus, the title compound having the following physical properties was obtained.

TLC: Rf 0.36 (hexane:ethyl acetate=3:1);
MS: 339 (M+H)$^+$;
NMR: δ 10.32 (s, 1H), 7.47 (d, J=8.60 Hz, 1H), 7.08-7.17 (m, 2H), 6.92-7.01 (m, 2H), 6.78 (dd, J=8.60, 2.56 Hz, 1H), 6.73 (d, J=2.56 Hz, 1H), 3.80 (d, J=5.85 Hz, 2H), 2.84 (dd, J=13.63, 6.50 Hz, 1H), 2.67-2.76 (m, 2H), 2.50 (s, 3H), 2.46-2.60 (m, 3H), 2.14-2.30 (m, 1H), 1.02 (d, J=6.77 Hz, 3H).

EXAMPLE 27

N-({6-[3-(4-fluorophenyl)-2-methylpropoxy]-1-methyl-3,4-dihydro-2-naphthalenyl}methyl)ethanamine The procedure of Example 5 was followed but using the compound prepared in Example 26 as a substitute for 6-(4-phenylbutoxy)-2-formylnaphthalene while using ethylamine as a substitute for piperidine. Thus, the compound of the present invention having the following physical properties was obtained.

TLC: Rf 0.23 (chloroform:methanol:aqueous ammonia=80:10:1);
MS: 849 (2M+CF$_3$CO$_2$H+H)$^+$, 735 (2M+H)$^+$, 368 (M+H)$^+$, 366, 323;
NMR (CD$_3$OD): δ 7.13-7.22 (m, 3H), 6.92-7.01 (m, 2H), 6.64-6.72 (m, 2H), 3.76 (d, J=5.67 Hz, 2H), 3.44 (s, 2H), 2.84 (dd, J=13.54, 6.40 Hz, 1H), 2.64-2.73 (m, 4H), 2.54 (dd, J=13.54, 7.78 Hz, 1H), 2.10-2.31 (m, 3H), 2.06 (s, 3H), 1.16 (t, J=7.23 Hz, 3H), 1.00 (d, J=6.77 Hz, 3H).

EXAMPLE 28

1-chloro-6-methoxy-3,4-dihydro-2-naphthalenecarbaldehyde

To a solution of 6-methoxy-3,4-dihydronaphthalen-1(2H)-one (300 mg) in toluene (3 mL), N,N-dimethylformamide (0.39 mL) and phosphorous oxychloride (0.49 mL) were dropped at 0° C., followed by stirring at 70° C. for 6 hours. The reaction mixture was poured into ice and the mixture was extracted with ethyl acetate. The organic layer was washed with brine, dried and concentrated. Thus, the obtained residue was purified by silica gel column chromatography (hexane:ethyl acetate 20:1 to 10:1) to thereby give the title compound (285 mg) having the following physical properties.

TLC: Rf 0.53 (hexane:ethyl acetate=3:1);
MS (EI, Pos.): 224, 222 (M$^+$), 193, 158, 115;
NMR: δ 10.34 (s, 1H), 7.81 (d, J=8.8 Hz, 1H), 6.84 (dd, J=8.8, 2.7 Hz, 1H), 6.75 (d, J=2.7 Hz, 1H), 3.86 (s, 3H), 2.82 (t, J=7.9 Hz, 2H), 2.63 (t, J=7.9 Hz, 2H).

EXAMPLE 29

1-chloro-6-hydroxy-3,4-dihydro-2-naphthalenecarbaldehyde

To a solution of the compound (1.50 g) prepared in Example 28 in dichloromethane (20 mL), aluminum chloride (4.46 g) was added at 0° C., followed by stirring at 50° C. for 6 hours. The reaction mixture was poured into ice and the mixture was extracted with ethyl acetate. The organic layer was dried and then concentrated. Thus, the obtained residue was purified by silica gel column chromatography (hexane:tetrahydrofuran=5:1 to 3:1) to thereby give the title compound (842 mg) having the following physical properties.

TLC: Rf 0.26 (hexane:ethyl acetate=3:1);
NMR: δ 10.33 (s, 1H), 7.77 (d, J=8.40 Hz, 1H), 6.79 (dd, J=8.40, 2.60 Hz, 1H), 6.71 (d, J=2.60 Hz, 1H), 5.45 (s, 1H), 2.75-2.85 (m, 2H), 2.58-2.68 (m, 2H).

EXAMPLE 30

1-chloro-6-{[(2S)-3-(4-chlorophenyl)-2-methylpropyl]oxy}-3,4-dihydro-2-naphthalenecarbaldehyde The procedure of Example 19 was followed but using the compound prepared in Example 29 as a substitute for the compound prepared in Example 13. Thus, the title compound having the following physical properties was obtained.

TLC: Rf 0.50 (hexane:ethyl acetate=6:1);
MS: 377, 375 (M+H)$^+$;
NMR: δ 10.33 (s, 1H), 7.79 (d, J=8.8 Hz, 1H), 7.20-7.30 (m, J=8.4 Hz, 2H), 7.10 (d, J=8.4 Hz, 2H), 6.80 (dd, J=8.8, 2.7 Hz, 1H), 6.72 (d, J=2.7 Hz, 1H), 3.81 (d, J=5.9 Hz, 2H), 2.75-2.90 (m, 3H), 2.50-2.68 (m, 3H), 2.15-2.31 (m, 1H), 1.03 (d, J=6.8 Hz, 3H).

EXAMPLE 31

N-({1-[(1-chloro-6-{[(2S)-3-(4-chlorophenyl)-2-methylpropyl]oxy}-3,4-dihydro-2-naphthalenyl)methyl]-3-azetidinyl}carbonyl)methanesulfonamide The procedure of Example 6 was followed but using the compound prepared in Example 30 as a substitute for 6-(3-phenylpropoxy)-2-formylnaphthalene while using methanesulfonamide as a substitute for benzenesulfonamide. Thus, the compound of the present invention having the following physical properties was obtained.

TLC: Rf 0.35 (chloroform:methanol:aqueous ammonia=80:10:1);
MS: 539, 537 (M+H)$^+$, 361, 359;
NMR (CD$_3$OD): δ 7.54 (d, J=8.40 Hz, 1H), 7.25 (d, J=8.60 Hz, 2H), 7.15 (d, J=8.60 Hz, 2H), 6.78 (dd, J=8.40, 2.60 Hz, 1H), 6.74 (d, J=2.60 Hz, 1H), 4.13 (d, J=8.20 Hz, 4H), 4.08 (s, 2H), 3.81 (d, J=5.70 Hz, 2H), 3.36-3.51 (m, 1H), 3.01 (s, 3H), 2.77-2.89 (m, 3H), 2.55 (dd, J=13.50, 7.80 Hz, 1H), 2.39-2.49 (m, 2H), 2.12-2.27 (m, 1H), 1.00 (d, J=6.80 Hz, 3H).

EXAMPLE 31-1 TO EXAMPLE 31-2

The procedure of Example 31 was followed but using a corresponding sulfonamide compound as a substitute for methanesulfonamide. Thus, the compound of the present invention having the following physical properties was obtained.

EXAMPLE 31-1

N-({1-[(1-chloro-6-{[(2S)-3-(4-chlorophenyl)-2-methylpropyl]oxy}-3,4-dihydro-2-naphthalenyl)methyl]-3-azetidinyl}carbonyl)-2,6-difluorobenzenesulfonamide TLC: Rf 0.43 (chloroform:methanol:aqueous ammonia=80:10:1);

MS: 637, 635 (M+H)⁺, 361, 359;

NMR (CD₃OD): δ 7.54 (d, J=8.60 Hz, 1H), 7.42-7.52 (m, 1H), 7.24 (d, J=8.60 Hz, 2H), 7.15 (d, J=8.60 Hz, 2H), 7.00 (t, J=8.70 Hz, 2H), 6.79 (dd, J=8.60, 2.60 Hz, 1H), 6.74 (d, J=2.60 Hz, 1H), 4.23-4.33 (m, 4H), 4.21 (s, 2H), 3.81 (d, J=5.90 Hz, 2H), 3.40-3.56 (m, 1H), 2.77-2.90 (m, 3H), 2.55 (dd, J=13.50, 7.80 Hz, 1H), 2.43 (t, J=8.50 Hz, 2H), 2.11-2.27 (m, 1H), 1.00 (d, J=6.80 Hz, 3H).

EXAMPLE 31-2

N-({1-[(1-chloro-6-{[(2S)-3-(4-chlorophenyl)-2-methylpropyl]oxy}-3,4-dihydro-2-naphthalenyl)methyl]-3-azetidinyl}carbonyl)-3,5-dimethyl-4-isoxazolesulfonamide TLC: Rf 0.43 (chloroform:methanol:aqueous ammonia=80:20:4);

MS: 620, 618 (M+H)⁺, 361, 359;

NMR (CD₃OD): δ 7.54 (d, J=8.60 Hz, 1H), 7.25 (d, J=8.60 Hz, 2H), 7.15 (d, J=8.60 Hz, 2H), 6.79 (dd, J=8.60, 2.60 Hz, 1H), 6.74 (d, J=2.60 Hz, 1H), 4.03-4.22 (m, 6H), 3.81 (d, J=5.90 Hz, 2H), 3.35-3.50 (m, 1H), 2.75-2.90 (m, 3H), 2.62 (s, 3H), 2.55 (dd, J=13.50, 7.80 Hz, 1H), 2.42 (t, J=8.40 Hz, 2H), 2.36 (s, 3H), 2.11-2.29 (m, 1H), 1.01 (d, J=6.80 Hz, 3H).

EXAMPLE 32

3-methoxyphenyl trifluoromethanesulfonate

To a solution of 3-methoxyphenol (5 g) in dichloromethane (30 mL), pyridine (15.6 mL) and trifluoromethanesulfonic anhydride (8.08 mL) were dropped at 0° C., followed by stirring for 30 minutes. The reaction mixture was poured into a saturated aqueous sodium hydrogen carbonate solution and the mixture was extracted with dichloromethane. The organic layer was successively washed with a saturated aqueous sodium hydrogen carbonate solution, water, and brine, and was concentrated. The obtained residue was added with t-butyl methyl ether and then the mixture was successively washed with 1 N hydrochloric acid, a saturated aqueous sodium hydrogen carbonate solution, water, and brine, dried and concentrated. Thus, the title compound (10.0 g) having the following physical properties.

TLC: Rf 0.59 (hexane:ethyl acetate=6:1);

MS: (EI, Pos.): 256 (M⁺), 123;

NMR: δ 7.35 (t, J=8.32 Hz, 1H), 6.93 (dd, J=8.32, 2.38 Hz, 1H), 6.87 (dd, J=8.32, 2.38 Hz, 1H), 6.81 (t, J=2.38 Hz, 1H), 3.83 (s, 3H).

EXAMPLE 33

1-isobutyl-3-methoxybenzene

To a solution of the compound (2 g) prepared in Example 32 in tetrahydrofuran (35 mL), 1-methyl-2-pyrrolidone (5.2 mL), tris(2,4-pentanedionato)iron(III) (413.5 mg), and isobutyl magnesium bromide (2M diethyl ether solution, 4.68 mL) were added thereto, followed by stirring at room temperature for 4 hours. The reaction mixture was added with a saturated aqueous ammonium chloride solution and the mixture was extracted with t-butyl methyl ether. The organic layer was successively washed with a saturated aqueous ammonium chloride solution, water, and brine, dried and concentrated. Thus, the obtained residue was purified by silica gel column chromatography (hexane:tetrahydrofuran=50:1 to 20:1) to thereby give the title compound (922.5 mg) having the following physical properties.

TLC: Rf 0.48 (hexane:ethyl acetate=20:1);

MS (EI, Pos.): 164 (M⁺), 121, 107;

NMR: δ 7.17 (t, J=7.78 Hz, 1H), 6.67-6.75 (m, 3H), 3.79 (s, 3H), 2.44 (d, J=7.32 Hz, 2H), 1.78-1.94 (m, 1H), 0.90 (d, J=6.59 Hz, 6H).

EXAMPLE 34

4-isobutyl-2-methoxybenzaldehyde

To a solution of N,N,N',N'-tetramethylethylenediamine (389 mg) in hexane (15 mL), a solution of t-butyllithium in pentane (1.6M, 2.09 mL) was dropped at −78° C., followed by stirring. Then, a solution of the compound (500 mg) prepared in Example 33 in hexane (6 mL) was dropped thereto, followed by stirring for 6 hours. To a solution of N,N-dimethylformamide (5 mL) in tetrahydrofuran (30 mL), the reaction mixture was dropped at 0° C. Then, the reaction mixture was poured into a saturated aqueous ammonium chloride solution. The solvent was concentrated and was added with water. Then, the mixture was extracted with ethyl acetate. The organic layer was successively washed with a saturated aqueous ammonium chloride solution, water, and brine. After the organic layer was dried, the solvent was concentrated. Thus, the obtained residue was purified by silica gel column chromatography (hexane:ethyl acetate=30:1) to thereby give the title compound (183 mg) having the following physical properties.

TLC: Rf 0.66 (hexane:ethyl acetate=3:1);

MS (EI, Pos.): 192 (M⁺), 174, 150, 149, 121, 91;

NMR: δ 10.39 (s, 1H), 7.73 (d, J=7.87 Hz, 1H), 6.81 (d, J=7.87 Hz, 1H), 6.73 (d, J=0.91 Hz, 1H), 3.91 (s, 3H), 2.51 (d, J=7.32 Hz, 2H), 1.83-1.98 (m, 1H), 0.92 (d, J=6.59 Hz, 6H).

EXAMPLE 35

(4-isobutyl-2-methoxyphenyl)methanol

To a solution of the compound (171 mg) prepared in Example 34 in methanol (10 mL), sodium borohydride (100 mg) was added, followed by stirring for 1.5 hours. The reaction mixture was concentrated and the obtained residue was added with a saturated aqueous ammonium chloride solution. Then, the mixture was extracted with t-butyl methyl ether. The organic layer was successively washed with a saturated aqueous ammonium chloride solution, a saturated aqueous sodium hydrogencarbonate solution, water, and brine. After the organic layer was dried, the solvent was concentrated. Thus, the obtained residue was purified by silica gel column chromatography (hexane:ethyl acetate=30:1 to 10:1) to thereby give the title compound (175 mg) having the following physical properties.

TLC: Rf 0.44 (hexane:ethyl acetate=3:1);

MS (EI, Pos.): 194 (M⁺), 151, 137, 123, 91;

NMR: δ 7.15 (d, J=7.50 Hz, 1H), 6.72 (dd, J=7.50, 1.40 Hz, 1H), 6.67 (d, J=1.40 Hz, 1H), 4.65 (s, 2H), 3.86 (s, 3H), 2.47 (d, J=7.14 Hz, 2H), 2.27 (s, 1H), 1.79-1.94 (m, 1H), 0.91 (d, J=6.59 Hz, 6H).

EXAMPLE 36

6-[(4-isobutyl-2-methoxybenzyl)oxy]-1-methyl-3,4-dihydro-2-naphthalenecarbaldehyde The procedure of Example 19 was followed but using the compound prepared in Example 35 as a substitute for the compound prepared in Example 13. Thus, the title compound having the following physical properties was obtained.

TLC: Rf 0.54 (hexane:ethyl acetate=3:1);
MS: 365 (M+H)$^+$, 177;
NMR: δ 10.32 (s, 1H), 7.48 (d, J=8.60 Hz, 1H), 7.32 (d, J=7.68 Hz, 1H), 6.84-6.93 (m, 2H), 6.74-6.79 (m, 1H), 6.69-6.72 (m, 1H), 5.11 (s, 2H), 3.86 (s, 3H), 2.67-2.78 (m, 2H), 2.50 (s, 3H), 2.46-2.55 (m, 2H), 2.48 (d, J=7.14 Hz, 2H), 1.80-1.97 (m, 1H), 0.92 (d, J=6.59 Hz, 6H).

EXAMPLE 37

1-{6-[(4-isobutyl-2-methoxybenzyl)oxy]-1-methyl-3,4-dihydro-2-naphthalenyl}-N,N-dimethylmethanamine The procedure of Example 5 was followed but using the compound prepared in Example 36 as a substitute for 6-(4-phenylbutoxy)-2-formylnaphthalene while using dimethylamine as a substitute for piperidine. Thus, the compound of the present invention having the following physical properties was obtained.

TLC: Rf 0.49 (chloroform:methanol:aqueous ammonia=80:10:1);
MS: 901 (2M+CF$_3$CO$_2$H+H)$^+$, 787 (2M+H)$^+$, 394 (M+H)$^+$, 349, 323, 177;
NMR (CD$_3$OD): δ 7.27 (d, J=7.68 Hz, 1H), 7.21 (d, J=8.23 Hz, 1H), 6.71-6.82 (m, 4H), 5.03 (s, 2H), 3.84 (s, 3H), 3.15 (s, 2H), 2.63-2.72 (m, 2H), 2.48 (d, J=7.14 Hz, 2H), 2.21-2.30 (m, 8H), 2.06 (s, 3H), 1.80-1.95 (m, 1H), 0.91 (d, J=6.59 Hz, 6H).

EXAMPLE 37-1 TO EXAMPLE 37-5

The procedure of Example 37 was followed but using a corresponding amine compound as a substitute for dimethylamine. Thus, the compound of the present invention having the following physical properties was obtained.

EXAMPLE 37-1

[1-({6-[(4-isobutyl-2-methoxybenzyl)oxy]-1-methyl-3,4-dihydro-2-naphthalenyl}methyl)-3-azetidinyl]methanol TLC: Rf 0.29 (chloroform:methanol:aqueous ammonia=80:10:1);
MS: 985 (2M+CF$_3$CO$_2$H+H)$^+$, 871 (2M+H)$^+$, 436 (M+H)$^+$, 349, 177;
NMR (CD$_3$OD): δ 7.23-7.29 (m, 2H), 6.71-6.83 (m, 4H), 5.01-5.06 (m, 2H), 3.84 (s, 3H), 3.78 (t, J=8.97 Hz, 2H), 3.70 (s, 2H), 3.63 (d, J=5.12 Hz, 2H), 3.53 (t, J=7.96 Hz, 2H), 2.77-2.93 (m, 1H), 2.64-2.73 (m, 2H), 2.48 (d, J=7.32 Hz, 2H), 2.18-2.28 (m, 2H), 2.15 (s, 3H), 1.82-1.96 (m, 1H), 0.91 (d, J=6.59 Hz, 6H).

EXAMPLE 37-2

1-({6-[(4-isobutyl-2-methoxybenzyl)oxy]-1-methyl-3,4-dihydro-2-naphthalenyl}methyl)pyrrolidine TLC: Rf 0.49 (chloroform:methanol:aqueous ammonia=80:10:1);
MS: 953 (2M+CF$_3$CO$_2$H+H)$^+$, 839 (2M+H)$^+$, 420 (M+H)$^+$, 349, 177;
NMR (CD$_3$OD): δ 7.26 (d, J=7.68 Hz, 1H), 7.20 (d, J=8.23 Hz, 1H), 6.71-6.80 (m, 4H), 5.02 (s, 2H), 3.84 (s, 3H), 3.36 (s, 2H), 2.59-2.72 (m, 6H), 2.47 (d, J=7.32 Hz, 2H), 2.26-2.34 (m, 2H), 2.07 (s, 3H), 1.78-1.96 (m, 5H), 0.91 (d, J=6.59 Hz, 6H).

EXAMPLE 37-3

1-({6-[(4-isobutyl-2-methoxybenzyl)oxy]-1-methyl-3,4-dihydro-2-naphthalenyl}methyl)-2,5-dihydro-1H-pyrrole TLC: Rf 0.49 (chloroform:methanol:aqueous ammonia=80:10:1);
MS: 949 (2M+CF$_3$CO$_2$H+H)$^+$, 835 (2M+H)$^+$, 418 (M+H)$^+$, 349, 177;
NMR (CD$_3$OD): δ 7.13-7.32 (m, 2H), 6.61-6.85 (m, 4H), 5.82 (s, 2H), 5.02 (s, 2H), 3.84 (s, 3H), 3.45-3.57 (m, 6H), 2.62-2.75 (m, 2H), 2.48 (d, J=7.14 Hz, 2H), 2.22-2.35 (m, 2H), 2.08 (s, 3H), 1.79-1.97 (m, 1H), 0.91 (d, J=6.59 Hz, 6H).

EXAMPLE 37-4

3-({6-[(4-isobutyl-2-methoxybenzyl)oxy]-1-methyl-3,4-dihydro-2-naphthalenyl}methyl)-1,3-thiazolidine TLC: Rf 0.34 (chloroform:methanol:aqueous ammonia=80:10:1);
MS: 875 (2M+H)$^+$, 438 (M+H)$^+$, 349, 177;
NMR: δ 7.32 (d, J=7.50 Hz, 1H), 7.20 (d, J=8.23 Hz, 1H), 6.79-6.85 (m, 2H), 6.75 (dd, J=7.50, 1.37 Hz, 1H), 6.68 (d, J=1.37 Hz, 1H), 5.06 (s, 2H), 4.10 (s, 2H), 3.84 (s, 3H), 3.19 (s, 2H), 3.12 (t, J=6.22 Hz, 2H), 2.95 (t, J=6.22 Hz, 2H), 2.69-2.77 (m, 2H), 2.47 (d, J=7.14 Hz, 2H), 2.34-2.43 (m, 2H), 2.06 (s, 3H), 1.82-1.95 (m, 1H), 0.92 (d, J=6.59 Hz, 6H).

EXAMPLE 37-5

1-({6-[(4-isobutyl-2-methoxybenzyl)oxy]-1-methyl-3,4-dihydro-2-naphthalenyl}methyl)azocane TLC: Rf 0.49 (chloroform:methanol:aqueous ammonia=80:10:1);
MS: 462 (M+H)$^+$, 349, 177;
NMR (CD$_3$OD): δ 7.26 (d, J=7.68 Hz, 1H), 7.16 (d, J=8.42 Hz, 1H), 6.69-6.82 (m, 4H), 5.02 (s, 2H), 3.84 (s, 3H), 3.17-3.24 (m, 2H), 2.61-2.71 (m, 2H), 2.51-2.61 (m, 4H), 2.48 (d, J=7.14 Hz, 2H), 2.27-2.38 (m, 2H), 2.04 (s, 3H), 1.81-1.97 (m, 1H), 1.48-1.75 (m, 10H), 0.91 (d, J=6.59 Hz, 6H).

EXAMPLE 38

N-[2-({[6-(3-phenylpropoxy)-2-naphthyl]methyl}amino)ethyl]benzenesulfonamide

The procedure of Example 5 was followed but using N-benzenesulfonyl-1,2-ethylenediamine as a substitute for piperidine. Thus, the compound of the present invention having the following physical properties was obtained.

TLC: Rf 0.46 (chloroform:methanol=10:1);
MS: 949 (2M+H)$^+$, 475 (M+H)$^+$, 275;
NMR (CD$_3$OD): δ 7.77-7.83 (m, 2H), 7.61-7.73 (m, 3H), 7.44-7.58 (m, 3H), 7.31-7.38 (m, 1H), 7.10-7.29 (m, 7H), 4.07 (t, J=6.22 Hz, 2H), 3.80 (s, 2H), 3.00 (t, J=6.40 Hz, 2H), 2.80-2.88 (m, 2H), 2.65 (t, J=6.40 Hz, 2H), 2.08-2.19 (m, 2H).

EXAMPLE 38-1 TO EXAMPLE 38-3

The procedure of Example 38 was followed but using a corresponding amine compound as a substitute for N-benze-

EXAMPLE 38-1

1-{[6-(3-phenylpropoxy)-2-naphthyl]methyl}-3-azetidinecarboxamide

TLC: Rf 0.23 (chloroform:methanol:aqueous ammonia=80:20:1);
MS: 749 (2M+H)$^+$, 375 (M+H)$^+$, 275;
NMR (CD$_3$OD): δ 7.62-7.81 (m, 3H), 7.08-7.44 (m, 8H), 4.07 (t, J=6.22 Hz, 2H), 3.89 (s, 2H), 3.67 (t, J=8.51 Hz, 2H), 3.52-3.60 (m, 2H), 3.30-3.43 (m, 1H), 2.79-2.88 (m, 2H), 2.07-2.18 (m, 2H).

EXAMPLE 38-2

N-methyl-1-{[6-(3-phenylpropoxy)-2-naphthyl]methyl}-3-azetidinecarboxamide

TLC: Rf 0.34 (chloroform:methanol:aqueous ammonia=90:10:1);
MS: 389 (M+H)$^+$, 275;
NMR: δ 7.60-7.74 (m, 3H), 7.04-7.42 (m, 8H) 6.04-6.23 (m, 1H), 4.07 (t, J=6.31 Hz, 2H), 3.73 (s, 2H), 3.46 (t, J=7.59 Hz, 2H), 3.38 (dd, J=7.59, 6.15 Hz, 2H), 3.03-3.15 (m, 1H), 2.82-2.89 (m, 5H), 2.11-2.23 (m, 2H).

EXAMPLE 38-3

3-({[6-(3-phenylpropoxy)-2-naphthyl]methyl}amino)propanenitrile

TLC: Rf 0.48 (hexane:ethyl acetate=1:3);
MS (EI): 344 (M$^+$), 275, 157, 91;
NMR (CD$_3$OD): δ 7.64-7.77 (m, 3H), 7.38-7.47 (m, 1H), 7.06-7.32 (m, 7H), 4.07 (t, J=6.22 Hz, 2H), 3.90 (s, 2H), 2.78-2.92 (m, 4H), 2.61 (t, J=6.95 Hz, 2H), 2.07-2.19 (m, 2H).

EXAMPLE 39 t-butyl (2-cyanoethyl) {[6-(3-phenylpropoxy)-2-naphthyl]methyl}carbamate

The procedure of Example 21 was followed but using the compound prepared in Example 38-3 as a substitute for the compound prepared in Example 20. Thus, the compound of the present invention having the following physical properties was obtained.
TLC: Rf 0.77 (hexane:ethyl acetate=1:1);
MS (EI): 444 (M$^+$), 388, 343, 275, 157;
NMR (CD$_3$OD): δ 7.58-7.79 (m, 3H), 7.11-7.38 (m, 8H), 4.64 (s, 2H), 4.07 (t, J=6.22 Hz, 2H), 3.46-3.60 (m, 2H), 2.81-2.87 (m, 2H), 2.53-2.72 (m, 2H), 2.07-2.19 (m, 2H), 1.40-1.64 (m, 9H).

EXAMPLE 40 t-butyl [3-(hydroxyamino)-3-iminopropyl]{[6-(3-phenylpropoxy)-2-naphthyl]methyl}carbamate (compound 40a) and t-butyl [3-(hydroxyamino)-3-(hydroxyimino)propyl]{[6-(3-phenylpropoxy)-2-naphthyl]methyl}carbamate (compound 40b)

To a solution of the compound (510 mg) prepared in Example 39 in mixed solution of diethyl ether (10 mL) and tetrahydrofuran (6 mL), triethylamine (0.32 mL) and hydroxylamine hydrochloride (159.4 mg) were added, followed by stirring at 60° C. for 11 hours and at 80° C. for 16 hours. The reaction mixture was concentrated and the obtained residue was purified by silica gel column chromatography (hexane:ethyl acetate=4:1) to thereby give the compound 40a (46.3 mg) and the compound 40b (169.5 mg) of the present invention having the following physical properties.

Compound 40a:

TLC: Rf 0.19 (chloroform:methanol=10:1);
MS: 955 (2M+H)$^+$, 478 (M+H)$^+$, 422, 378, 275;
NMR: δ 7.50-7.76 (m, 3H), 7.02-7.36 (m, 8H), 4.70-4.94 (m, 1H), 4.54 (s, 2H), 4.06 (t, J=6.31 Hz, 2H), 3.30-3.55 (m, 2H), 2.85 (t, J=7.60 Hz, 2H), 2.23-2.42 (m, 2H), 2.10-2.23 (m, 2H), 1.48 (s, 9H).

Compound 40b:

TLC: Rf 0.29 (chloroform:methanol=10:1);
MS: 987 (2M+H)$^+$, 494 (M+H)$^+$, 438, 394, 275;
NMR: δ 7.50-7.75 (m, 3H), 7.03-7.35 (m, 8H), 4.54 (s, 2H), 4.06 (t, J=6.31 Hz, 2H), 3.35-3.65 (m, 2H), 2.85 (t, J=7.60 Hz, 2H), 2.54-2.66 (m, 2H), 2.10-2.24 (m, 2H), 1.46 (s, 9H).

EXAMPLE 41 t-butyl [2-(5-oxo-4,5-dihydro-1,2,4-oxadiazol-3-yl)ethyl]{[6-(3-phenylpropoxy)-2-naphthyl]methyl}carbamate To a solution of the compound 40a (46 mg) prepared in Example 40 in tetrahydrofuran (1 mL), carbonyldiimidazole (23.4 mg) was added, followed by stirring at room temperature for 1.5 hours. The reaction mixture was added with water and the mixture was extracted with ethyl acetate. The organic layer was successively washed with water and brine, dried and concentrated. A solution of the obtained residue in toluene (1.5 mL) was stirred at 80° C. for 1.5 hours. Thus, the obtained residue was purified by silica gel column chromatography (hexane:ethyl acetate=3:1 to 1:1) to thereby give the compound of the present invention (5.7 mg) having the following physical properties.
TLC: Rf 0.26 (hexane:ethyl acetate=1:1);
MS: 907 (2M+H)$^+$, 504 (M+H)$^+$, 404;
NMR (CD$_3$OD): δ 7.57-7.76 (m, 3H), 7.08-7.35 (m, 8H), 4.58 (s, 2H), 4.07 (t, J=6.22 Hz, 2H), 3.46-3.63 (m, 2H), 2.84 (t, J=7.60 Hz, 2H), 2.64-2.77 (m, 2H), 2.07-2.19 (m, 2H), 1.39-1.53 (m, 9H).

EXAMPLE 42

3-[2-({[6-(3-phenylpropoxy)-2-naphthyl]methyl}amino)ethyl]-1,2,4-oxadiazol-5(4H)-one hydrochloride To a solution of the compound (5.7 mg) prepared in Example 41 in dioxane (0.5 mL), a 4N hydrogen chloride in dioxane (1 mL) was added at 0° C., followed by stirring at room temperature for 1 hour. The reaction mixture was concentrated and added with diethyl ether. Then, the precipitated solid was washed to thereby give the compound of the present invention (3.3 mg) having the following physical properties.
TLC: Rf 0.33 (chloroform:methanol:aqueous ammonia=20:5:1);

MS: 807 (2M+H)$^+$, 404 (M+H)$^+$, 360, 275;

NMR (CD$_3$OD): δ 7.75-7.95 (m, 3H), 7.44-7.56 (m, 1H), 7.13-7.30 (m, 7H), 4.38 (s, 2H), 4.09 (t, J=6.22 Hz, 2H), 3.45 (t, J=7.04 Hz, 2H), 3.00 (t, J=7.04 Hz, 2H), 2.81-2.88 (m, 2H), 2.08-2.21 (m, 2H).

EXAMPLE 42-1

N,N'-dihydroxy-3-({[6-(3-phenylpropoxy)-2-naphthyl]methyl}amino)propanimidamide dihydrochloride The procedure of Example 42 was followed but using the compound prepared in Example 40b as a substitute for the compound prepared in Example 41. Thus, the compound of the present invention having the following physical properties was obtained.

TLC: Rf 0.25 (chloroform:methanol:aqueous ammonia=80:10:1);

MS: 787 (2M+H)$^+$, 394 (M+H)$^+$, 275;

NMR (CD$_3$OD): δ 7.94-7.97 (m, 1H), 7.80-7.87 (m, 2H), 7.52-7.58 (m, 1H), 7.12-7.29 (m, 7H), 4.40 (s, 2H), 4.09 (t, J=6.22 Hz, 2H), 3.43-3.51 (m, 2H), 3.02-3.10 (m, 2H), 2.80-2.88 (m, 2H), 2.08-2.20 (m, 2H).

EXAMPLE 43

4-methyl-7-(4-phenylbutoxy)-1,2-dihydronaphthalene

The procedure of Example 11 was followed but using 1-bromo-4-phenylbutane as a substitute for benzyl bromide. Thus, the title compound having the following physical properties was obtained.

TLC: Rf 0.61 (dichloromethane:hexane=2:5);

MS (EI): 292 (M$^+$), 160, 145, 91;

NMR: δ 7.05-7.35 (m, 6H), 6.58-6.76 (m, 2H), 5.60-5.76 (m, 1H), 3.84-4.04 (m, 2H), 2.57-2.79 (m, 4H), 2.13-2.29 (m, 2H), 1.98-2.04 (m, 3H), 1.75-1.85 (m, 4H).

EXAMPLE 44

N-methyl-N-{2-[6-(4-phenylbutoxy)-3,4-dihydro-1 (2H)-naphthalenylidene]ethylidene}methanaminium chloride The procedure of Example 12 was followed but using the compound prepared in Example 43 as a substitute for the compound prepared in Example 11. The insoluble matter generated in extraction during the procedure was filtered and dried, to give the compound of the present invention having the following physical properties.

TLC: Rf 0.41 (hexane:ethyl acetate=3:1);

MS: 348 (M+H)$^+$;

NMR (CD$_3$OD): δ 8.78 (d, J=11.16 Hz, 1H), 8.07 (d, J=9.15 Hz, 1H), 7.10-7.29 (m, 5H), 7.01 (d, J=11.16 Hz, 1H), 6.89 (dd, J=9.15, 2.56 Hz, 1H), 6.82 (d, J=2.56 Hz, 1H), 4.04-4.12 (m, 2H), 3.66 (s, 3H), 3.56 (s, 3H), 3.07 (t, J=6.13 Hz, 2H), 2.91 (t, J=6.22 Hz, 2H), 2.63-2.74 (m, 2H), 1.90-2.03 (m, 2H), 1.75-1.87 (m, 4H).

EXAMPLE 45

N,N-dimethyl-2-[6-(4-phenylbutoxy)-3,4-dihydro-1 (2H)-naphthalenylidene]ethanamine To a solution of the compound (20 mg) prepared in Example 44 in methanol (1 mL), polymer supported-borohydride (manufactured by Aldrich Corporation, Cat. No 32,864-2) was added at −78° C., followed by stirring at room temperature for 30 minutes. After filtering off the reaction mixture and concentrating the filtrate, the resultant was dried to thereby give the compound of the present invention (18.5 mg) having the following physical properties.

TLC: Rf 0.33 (chloroform:methanol=10:1);

MS: 813 (2M+CF$_3$CO$_2$H+H)$^+$, 699 (2M+H)$^+$, 350 (M+H)$^+$, 305, 173;

NMR (CD$_3$OD): δ 7.50 (d, J=8.78 Hz, 1H), 7.08-7.29 (m, 5H), 6.68 (dd, J=8.78, 2.56 Hz, 1H), 6.59 (d, J=2.56 Hz, 1H), 5.85-5.94 (m, 1H), 3.89-3.98 (m, 2H), 3.15 (d, J=7.14 Hz, 2H), 2.61-2.76 (m, 4H), 2.44-2.53 (m, 2H), 2.29 (s, 6H), 1.71-1.84 (m, 6H).

EXAMPLE 53

N'-hydroxy-4-(hydroxymethyl)benzenecarboximidamide

A solution of hydroxylamine hydrochloride (5.2 g), 4-(hydroxymethyl)benzonitrile (5.0 g), and sodium hydrogen carbonate (12.6 g) in methanol (50 mL) was heated to reflux for 20 hours. The reaction mixture was filtered through Celite (trade name). Thus, the filtrate was concentrated to thereby give the title compound having the following physical properties. The product was used for next reaction without further purification.

TLC: Rf 0.21 (chloroform:methanol:aqueous ammonia=80:10:1);

NMR: δ 7.61 (d, J=8.10 Hz, 2H), 7.37 (d, J=8.10 Hz, 2H), 4.61 (s, 2H).

EXAMPLE 54

{4-[5-(4-isobutylphenyl)-1,2,4-oxadiazol-3-yl] phenyl}methanol

To a solution of the compound prepared in Example 53 in N,N-dimethylformamide (60 mL), 4-isobutylbenzoic acid (6.7 g), 1-ethyl-3-(3-dimethylaminoprophyl)carbodiimide hydrochloride (7.28 g), and 1-hydroxybenzotriazole monohydrate (5.1 g) were added, followed by stirring at room temperature for 30 minutes and then by stirring at 140° C. for 2 hours. The reaction mixture was added with water (50 mL) and the mixture was extracted with a mixed solution of ethyl acetate-hexane (10:1). The extract was successively washed with 0.5N hydrochloric acid, a saturated aqueous sodium hydrogen carbonate solution, and water, and dried and concentrated. Thus, the obtained residue was purified by silica gel column chromatography (hexane:ethyl acetate=1:0 to 1:1) to thereby give the title compound (4.14 g) having the following physical properties.

TLC: Rf 0.54 (hexane:ethyl acetate=1:1);

MS: 309 (M+H)$^+$, 161;

NMR (CD$_3$OD): δ 8.13 (d, J=8.60 Hz, 2H), 8.11 (d, J=8.42 Hz, 2H), 7.53 (d, J=8.60 Hz, 2H), 7.41 (d, J=8.42 Hz, 2H), 4.69 (s, 2H), 2.61 (d, J=7.14 Hz, 2H), 1.86-2.04 (m, 1H), 0.94 (d, J=6.59 Hz, 6H).

EXAMPLE 55

4-[5-(4-isobutylphenyl)-1,2,4-oxadiazol-3-yl]benzaldehyde

To a solution of oxalyl chloride (1.74 mL) in methylene chloride (40 mL), dimethyl sulfoxide (2.13 mL) was added at −78° C. After the reaction mixture was stirred at −78° C. for 10 minutes, the resultant was added with the compound (2.14 g) prepared in Example 54 and N,N-diisopropylethylamine (14.6 mL) at −78° C., followed by stirring for 3 hours. The reaction mixture was concentrated and the obtained residue was diluted with ethyl acetate. The organic layer was successively washed with 0.5 mol/L aqueous potassium hydrogen sulfate solution, 1 mol/L hydrochloric acid, a saturated aqueous sodium hydrogen carbonate solution, and water, dried and concentrated. Thus, the obtained residue was purified by silica gel column chromatography (hexane:ethyl acetate 5:1) to thereby give the title compound (1.4 g) having the following physical properties.

TLC: Rf 0.61 (hexane:ethyl acetate=3:1);
MS (FAB, Pos.): 307 (M+H)$^+$;
NMR: δ 10.11 (s, 1H), 8.36 (d, J=8.23 Hz, 2H), 8.13 (d, J=8.42 Hz, 2H), 8.03 (d, J=8.42 Hz, 2H), 7.34 (d, J=8.23 Hz, 2H), 2.59 (d, J=7.32 Hz, 2H), 1.82-2.07 (m, 1H), 0.94 (d, J=6.59 Hz, 6H).

EXAMPLE 56

5-(4-isobutylphenyl)-3-[4-(1-pyrrolidinylmethyl) phenyl]-1,2,4-oxadiazole

The procedure of Example 5 was followed but using the compound prepared in Example 55 as a substitute for 6-(4-phenylbutoxy)-2-formylnaphthalene while using pyrrolidine as a substitute for piperidine. Thus, the compound of the present invention having the following physical properties was obtained.

TLC: Rf 0.76 (chloroform:methanol:aqueous ammonia=80:10:1);
MS: 723 (2M+H)$^+$, 362 (M+H)$^+$;
NMR (CD$_3$OD): δ 8.11 (d, J=8.42 Hz, 2H), 8.10 (d, J=8.60 Hz, 2H), 7.53 (d, J=8.60 Hz, 2H), 7.40 (d, J=8.42 Hz, 2H), 3.76 (s, 2H), 2.61-2.68 (m, 4H), 2.59 (d, J=7.32 Hz, 2H), 1.88-2.02 (m, 1H), 1.77-1.88 (m, 4H), 0.94 (d, J=6.59 Hz, 6H).

EXAMPLE 57

1,2,3,4-tetrahydro-6-isoquinolinol hydrochloride

To a solution of 3-hydroxyphenethylamine hydrochloride (3.0 g) in methanol (6 mL), formaldehyde (37% aqueous solution, 2.7 mL) and a catalytic amount of concentrated hydrochloric acid were added, followed by stirring at 45° C. for 18 hours. The reaction mixture was concentrated and the obtained solid was washed with a mixed solvent of diisopropyl ether-methanol (1:2) to thereby give the title compound (2.8 g) having the following physical properties.

TLC: Rf 0.59 (chloroform:methanol:aqueous ammonia=80:20:4);
MS (FAB, Pos.): 150 (M+H)$^+$;
NMR (CD$_3$OD): δ 7.02 (d, J=8.42 Hz, 1H), 6.70 (dd, J=8.42, 2.47 Hz, 1H), 6.64 (d, J=2.47 Hz, 1H), 4.23 (s, 2H), 3.44 (t, J=6.40 Hz, 2H), 3.03 (t, J=6.40 Hz, 2H).

EXAMPLE 58 t-butyl 6-hydroxy-3,4-dihydro-2(1H)-isoquinolinecarboxylate

The procedure of Example 21 was followed but using the compound prepared in Example 57 as a substitute for the compound prepared in Example 20. Thus, the title compound having the following physical properties was obtained.

TLC: Rf 0.33 (hexane:ethyl acetate=3:1);
MS (FAB, Pos., Glycerin+m-NBA): 250 (M+H)$^+$, 194;
NMR: δ 6.96 (d, J=8.23 Hz, 1H), 6.67 (dd, J=8.23, 2.58 Hz, 1H), 6.62 (d, J=2.58 Hz, 1H), 4.86-5.26 (m, 1H), 4.49 (s, 2H), 3.61 (t, J=5.95 Hz, 2H), 2.77 (t, J=5.95 Hz, 2H), 1.49 (s, 9H).

EXAMPLE 59 t-butyl 6-{[(trifluoromethyl)sulfonyl]oxy}-3,4-dihydro-2(1H)-isoquinolinecarboxylate The procedure of Example 32 was followed but using the compound prepared in Example 58 as a substitute for 3-methoxyphenol. Thus, the title compound having the following physical properties was obtained.

TLC: Rf 0.51 (hexane:ethyl acetate=3:1);
MS (FAB, Pos., Glycerin+m-NBA): 382 (M+H)$^+$, 380, 326;
NMR: δ 7.13-7.21 (m, 1H), 7.00-7.13 (m, 2H), 4.58 (s, 2H), 3.66 (t, J=5.85 Hz, 2H), 2.85 (t, J=5.85 Hz, 2H), 1.49 (s, 9H).

EXAMPLE 60 t-butyl 6-cyano-3,4-dihydro-2(1H)-isoquinolinecarboxylate

To a solution of the compound (0.56 g) prepared in Example 59 in N,N-dimethylformamide (3 mL), zinc cyanide (173 mg) and tetrakis(triphenyl)phosphine palladium (173 mg) were added, followed by stirring at 80° C. for 18 hours. The reaction mixture was added with a saturated aqueous sodium hydrogen carbonate solution and the mixture was extracted with t-butyl methyl ether. The organic layer was washed with water, dried and concentrated. Thus, the obtained residue was purified by silica gel column chromatography (hexane:ethyl acetate=1:0 to 3:1) to thereby give the title compound (130 mg) having the following physical properties.

TLC: Rf 0.36 (hexane:ethyl acetate=3:1)

EXAMPLE 61 t-butyl 6-[5-(4-isobutylphenyl)-1,2,4-oxadiazol-3-yl]-3,4-dihydro-2(1H)-isoquinolinecarboxylate The procedures of Examples 53 and 54 were followed but using the compound prepared in Example 60 as a substitute for 4-(hydroxymethyl)benzonitrile. Thus, the compound of the present invention having the following physical properties was obtained.

TLC: Rf 0.53 (hexane:ethyl acetate=3:1);
MS (FAB, Pos., Glycerin+m-NBA): 434 (M+H)$^+$, 378, 376;
NMR: δ 8.12 (d, J=8.05 Hz, 2H), 7.93-8.03 (m, 2H), 7.33 (d, J=8.05 Hz, 2H), 7.21-7.27 (m, 1H), 4.64 (s, 2H), 3.69 (t, J=5.76 Hz, 2H), 2.94 (t, J=5.76 Hz, 2H), 2.58 (d, J=7.14 Hz, 2H), 1.81-2.05 (m, 1H), 1.51 (s, 9H), 0.94 (d, J=6.77 Hz, 6H).

EXAMPLE 62

6-[5-(4-isobutylphenyl)-1,2,4-oxadiazol-3-yl]-1,2,3,4-tetrahydroisoquinoline hydrochloride The procedure of Example 42 was followed but using the compound prepared in Example 61 as a substitute for the compound prepared in Example 41. Thus, the compound of the present invention having the following physical properties was obtained.

TLC: Rf 0.58 (chloroform:methanol:aqueous ammonia=80:10:1);

MS (FAB, Pos., Glycerin+m-NBA): 487 (M+H+m-NBA)$^+$, 426 (M+H+Glycerin)$^+$, 334 (M+H)$^+$;

NMR (CD$_3$OD): δ 8.13 (d, J=8.42 Hz, 2H), 7.99-8.07 (m, 2H), 7.36-7.48 (m, 3H), 4.44 (s, 2H), 3.55 (t, J=6.50 Hz, 2H), 3.23 (t, J=6.50 Hz, 2H), 2.61 (d, J=7.50 Hz, 2H), 1.83-2.06 (m, 1H), 0.94 (d, J=6.59 Hz, 6H).

EXAMPLE 63-1

2-[[(1-methyl-1H-pyrrol-2-yl)methyl]({6-[5-phenyl-pentyl)oxy]-2-naphthyl}methyl)amino]ethanol A solution of the compound prepared in Example 5-12 in 5% acetic acid-dichloroethane (0.2M, 0.06 m mL), a solution of N-methylpyrrole-2-carbaldehyde in dichloroethane (0.5M, 0.072 mL), and triacetoxy sodium borohydride (7.6 g) were mixed, followed by stirring at room temperature for 20 hours. The reaction mixture was diluted with methanol (0.1 mL) and dichloroethane (0.3 mL) and was added with polystyrene sulfonyl hydrazide (2.74 mmol/g, 90 mg, manufactured by Argonaut Technology; Cat. No 800272), followed by stirring for 18 hours. Then, the resultant was added with D-series lanthanum sulfonic acid (0.150 mmol/pin, 1 pin, manufactured by MIMOTOPE; Cat. No MIL1025), followed by stirring for 2 hours. D-series lanthanum sulfonic acid was extracted and successively washed with dichloromethane, tetrahydrofuran, and methanol. Then, the resultant was soaked into a 10% triethylamine-methanol solution (0.4 mL), followed by stirring for 1 hour. The eluate was combined and D-series lanthanum sulfonic acid was soaked into a 10% triethylamine-methanol solution (0.4 mL) once again, followed by stirring for 1 hour. Both elutes were combined and concentrated to thereby give the compound of the present invention having the following physical properties.

HPLC retention time (minute): 3.89;
MS: 457 (M+H)$^+$.

EXAMPLE 63-2 TO EXAMPLE 63-61

The procedure of Example 63-1 was followed but using a corresponding aldehyde compound as a substitute for N-methylpyrrole-2-carbaldehyde. Thus, the compound of the present invention having the following physical properties was obtained.

EXAMPLE 63-2

2-[[(5-methyl-2-furyl)methyl]({6-[(5-phenylpentyl)oxy]-2-naphthyl}methyl)amino]ethanol HPLC retention time (minute): 3.88;
MS: 458 (M+H)$^+$, 303.

EXAMPLE 63-3

2-[{[5-(hydroxymethyl)-2-furyl]methyl}({6-[(5-phenylpentyl)oxy]-2-naphthyl}methyl)amino]ethanol HPLC retention time (minute): 3.75;
MS: 474 (M+H)$^+$, 303.

EXAMPLE 63-4

2-[benzyl({6-[(5-phenylpentyl)oxy]-2-naphthyl}methyl)amino]ethanol

HPLC retention time (minute): 3.93;
MS: 454 (M+H)$^+$, 303.

EXAMPLE 63-5

2-[(2,3-dimethoxybenzyl)({6-[(5-phenylpentyl)oxy]-2-naphthyl}methyl)amino]ethanol HPLC retention time (minute): 4.00;
MS: 514 (M+H)$^+$

EXAMPLE 63-6

2-[(2,4-dimethoxybenzyl)({6-[(5-phenylpentyl)oxy]-2-naphthyl}methyl)amino]ethanol HPLC retention time (minute): 4.02;
MS: 514 (M+H)$^+$.

EXAMPLE 63-7

2-[({6-[(5-phenylpentyl)oxy]-2-naphthyl}methyl)(2,4,6-trimethoxybenzyl)amino]ethanol HPLC retention time (minute): 4.06;
MS: 544 (M+H)$^+$, 181.

EXAMPLE 63-8

2-[(2,5-dimethoxybenzyl)({6-[(5-phenylpentyl)oxy]-2-naphthyl}methyl)amino]ethanol HPLC retention time (minute): 4.00;
MS: 514 (M+H)$^+$.

EXAMPLE 63-9

2-{({6-[(5-phenylpentyl)oxy]-2-naphthyl}methyl)[2-(trifluoromethyl)benzyl]amino}ethanol HPLC retention time (minute): 4.04;
MS: 522 (M+H)$^+$, 303.

EXAMPLE 63-10

2-[(2-methylbenzyl)({6-[(5-phenylpentyl)oxy]-2-naphthyl}methyl)amino]ethanol

HPLC retention time (minute): 4.00;
MS: 468 (M+H)$^+$, 303.

EXAMPLE 63-11

3-{[(2-hydroxyethyl)({6-[(5-phenylpentyl)oxy]-2-naphthyl}methyl)amino]methyl}benzonitrile HPLC retention time (minute): 3.89;
MS: 479 (M+H)$^+$, 303.

EXAMPLE 63-12

2-[(3-fluorobenzyl)({6-[(5-phenylpentyl)oxy]-2-naphthyl}methyl)amino]ethanol

HPLC retention time (minute): 3.97;
MS: 472 (M+H)+, 303.

EXAMPLE 63-13

2-[(3-fluoro-4-methoxybenzyl)({6-[(5-phenylpentyl)oxy]-2-naphthyl}methyl)amino]ethanol HPLC retention time (minute): 3.97;
MS: 502 (M+H)+, 303.

EXAMPLE 63-14

2-[(3-phenoxybenzyl)({6-[(5-phenylpentyl)oxy]-2-naphthyl}methyl)amino]ethanol

HPLC retention time (minute): 4.13;
MS: 546 (M+H)+.

EXAMPLE 63-15

2-[(3-methoxybenzyl)({6-[(5-phenylpentyl)oxy]-2-naphthyl}methyl)amino]ethanol

HPLC retention time (minute): 3.97;
MS: 484 (M+H)+, 303.

EXAMPLE 63-16

2-[({6-[(5-phenylpentyl)oxy]-2-naphthyl}methyl)(3,4,5-trimethoxybenzyl)amino]ethanol HPLC retention time (minute): 3.91;
MS: 544 (M+H)+.

EXAMPLE 63-17

2-[[4-(benzyloxy)-3-methoxybenzyl]({6-[(5-phenylpentyl)oxy]-2-naphthyl}methyl)amino]ethanol HPLC retention time (minute): 4.11;
MS: 590 (M+H)+.

EXAMPLE 63-18

2-[[3-(benzyloxy)benzyl]({6-[(5-phenylpentyl)oxy]-2-naphthyl}methyl)amino]ethanol HPLC retention time (minute): 4.15;
MS: 560 (M+H)+.

EXAMPLE 63-19

2-[[(2-chloro-3-quinolinyl)methyl]({6-[(5-phenylpentyl)oxy]-2-naphthyl}methyl)amino]ethanol HPLC retention time (minute): 3.99;
MS: 541, 539 (M+H)+, 303.

EXAMPLE 63-20

2-{[(2-hydroxyethyl)({6-[(5-phenylpentyl)oxy]-2-naphthyl}methyl)amino]methyl}-8-quinolinole HPLC retention time (minute): 3.99;
MS: 521 (M+H)+, 303.

EXAMPLE 63-21

2-[(3-methylbenzyl)({6-[(5-phenylpentyl)oxy]-2-naphthyl}methyl)amino]ethanol

HPLC retention time (minute): 4.00;
MS: 468 (M+H)+, 303.

EXAMPLE 63-22

4-{[(2-hydroxyethyl)({6-[(5-phenylpentyl)oxy]-2-naphthyl}methyl)amino]methyl}benzonitrile HPLC retention time (minute): 3.89;
MS: 479 (M+H)+, 303.

EXAMPLE 63-23

2-[(4-fluorobenzyl)({6-[(5-phenylpentyl)oxy]-2-naphthyl}methyl)amino]ethanol

HPLC retention time (minute): 3.97;
MS: 472 (M+H)+, 303.

EXAMPLE 63-24

2-[(4-phenoxybenzyl)({6-[(5-phenylpentyl)oxy]-2-naphthyl}methyl)amino]ethanol

HPLC retention time (minute): 4.13;
MS: 546 (M+H)+, 303.

EXAMPLE 63-25

2-[(4-methoxybenzyl)({6-[(5-phenylpentyl)oxy]-2-naphthyl}methyl)amino]ethanol

HPLC retention time (minute): 3.97;
MS: 484 (M+H)+, 303, 214.

EXAMPLE 63-26

2-[[4-(benzyloxy)benzyl]({6-[(5-phenylpentyl)oxy]-2-naphthyl}methyl)amino]ethanol HPLC retention time (minute): 4.15;
MS: 560 (M+H)+, 303.

EXAMPLE 63-27

2-[(1-naphthylmethyl)({6-[(5-phenylpentyl)oxy]-2-naphthyl}methyl)amino]ethanol

HPLC retention time (minute): 4.06;
MS: 504 (M+H)+, 303.

EXAMPLE 63-28

2-[[(4-methoxy-1-naphthyl)methyl]({6-[(5-phenyl-pentyl)oxy]-2-naphthyl}methyl)amino]ethanol HPLC retention time (minute): 4.11;
MS: 534 (M+H)+, 171.

EXAMPLE 63-29

2-[[3,4-bis(benzyloxy)benzyl]({6-[(5-phenylpentyl)oxy]-2-naphthyl}methyl)amino]ethanol HPLC retention time (minute): 4.28;
MS: 666 (M+H)+.

EXAMPLE 63-30

2-[({6-[(5-phenylpentyl)oxy]-2-naphthyl}methyl)(1H-pyrrol-2-ylmethyl)amino]ethanol HPLC retention time (minute): 3.89;
MS: 364 (M+H)+, 303.

EXAMPLE 63-31

2-[[(3-methyl-2-thienyl)methyl]({6-[(5-phenylpentyl)oxy]-2-naphthyl}methyl)amino]ethanol HPLC retention time (minute): 3.97;
MS: 474 (M+H)+, 303.

EXAMPLE 63-32

2-{({6-[(5-phenylpentyl)oxy]-2-naphthyl}methyl)[4-(trifluoromethyl)benzyl]amino}ethanol HPLC retention time (minute): 4.04;
MS: 522 (M+H)+, 303.

EXAMPLE 63-33

2-[[(2Z)-3,7-dimethyl-2,6-octadienyl]({6-[(5-phenyl-pentyl)oxy]-2-naphthyl}methyl)amino]ethanol HPLC retention time (minute): 4.21;
MS: 500 (M+H)+, 303.

EXAMPLE 63-34

2-[({6-[(5-phenylpentyl)oxy]-2-naphthyl}methyl)(propyl)amino]ethanol

HPLC retention time (minute): 3.84;
MS: 406 (M+H)+, 303.

EXAMPLE 63-35

2-[butyl({6-[(5-phenylpentyl)oxy]-2-naphthyl}methyl)amino]ethanol

HPLC retention time (minute): 3.91;
MS: 420 (M+H)+, 303.

EXAMPLE 63-36

2-[(3-furylmethyl)({6-[(5-phenylpentyl)oxy]-2-naphthyl}methyl)amino]ethanol

HPLC retention time (minute): 3.89;
MS: 444 (M+H)+, 303.

EXAMPLE 63-37

2-[(2,6-dimethoxybenzyl)({6-[(5-phenylpentyl)oxy]-2-naphthyl}methyl)amino]ethanol HPLC retention time (minute): 4.04;
MS: 514 (M+H)+.

EXAMPLE 63-38

2-[[4-(allyloxy)benzyl]({6-[(5-phenylpentyl)oxy]-2-naphthyl}methyl)amino]ethanol HPLC retention time (minute): 4.04;
MS: 510 (M+H)+, 303.

EXAMPLE 63-39

2-[[4-(octyloxy)benzyl]({6-[(5-phenylpentyl)oxy]-2-naphthyl}methyl)amino]ethanol HPLC retention time (minute): 4.50;
MS: 582 (M+H)+.

EXAMPLE 63-40

2-[[4-(heptyloxy)benzyl]({6-[(5-phenylpentyl)oxy]-2-naphthyl}methyl)amino]ethanol HPLC retention time (minute): 4.43;
MS: 568 (M+H)+, 303.

EXAMPLE 63-41

2-[(1,3-benzodioxol-4-ylmethyl)({6-[(5-phenylpentyl)oxy]-2-naphthyl}methyl)amino]ethanol HPLC retention time (minute): 3.95;
MS: 498 (M+H)+, 303.

EXAMPLE 63-42

2-[(2-hydroxyethyl)({6-[(5-phenylpentyl)oxy]-2-naphthyl}methyl)amino]ethanol

HPLC retention time (minute): 3.75;
MS: 406 (M+H)+, 303.

EXAMPLE 63-43

2-[(3,7-dimethyl-6-octenyl)({6-[(5-phenylpentyl)oxy]-2-naphthyl}methyl)amino]ethanol HPLC retention time (minute): 4.22;
MS: 502 (M+H)+, 303.

EXAMPLE 63-44

2-[[2-(t-butylsulfanyl)benzyl]({6-[(5-phenylpentyl)oxy]-2-naphthyl}methyl)amino]ethanol HPLC retention time (minute): 4.17;
MS: 542 (M+H)⁺.

EXAMPLE 63-45

2-{({6-[(5-phenylpentyl)oxy]-2-naphthyl}methyl)[4-(trifluoromethoxy)benzyl]amino}ethanol HPLC retention time (minute): 4.08;
MS: 538 (M+H)⁺, 303.

EXAMPLE 63-46

2-[{2-[(4-chlorophenyl)sulfanyl]benzyl}({6-[(5-phenylpentyl)oxy]-2-naphthyl}methyl)amino]ethanol HPLC retention time (minute): 4.22;
MS: 596 (M+H)⁺, 303.

EXAMPLE 63-47

2-[[(3-methyl-1-benzothien-2-yl)methyl]({6-[(5-phenylpentyl)oxy]-2-naphthyl}methyl)amino]ethanol HPLC retention time (minute): 3.71;
MS: 524 (M+H)⁺, 303

EXAMPLE 63-48

2-[({4-[(2E)-4-methyl-2-pentenyl]-3-cyclohexen-1-yl}methyl)({6-[(5-phenylpentyl)oxy]-2-naphthyl}methyl)amino]ethanol HPLC retention time (minute): 4.33;
MS: 540 (M+H)⁺, 303.

EXAMPLE 63-49

2-[({6-[(5-phenylpentyl)oxy]-2-naphthyl}methyl)(1,3-thiazol-2-ylmethyl)amino]ethanol HPLC retention time (minute): 3.86;
MS: 461 (M+H)⁺, 303.

EXAMPLE 63-50

2-[[2-(benzyloxy)ethyl]({6-[(5-phenylpentyl)oxy]-2-naphthyl}methyl)amino]ethanol HPLC retention time (minute): 4.00;
MS: 498 (M+H)⁺, 303.

EXAMPLE 63-51

2-[[3-(5-methyl-2-furyl)butyl]({6-[(5-phenylpentyl)oxy]-2-naphthyl}methyl)amino]ethanol HPLC retention time (minute): 4.06;
MS: 500 (M+H)⁺, 303.

EXAMPLE 63-52

2-[({6-[(5-phenylpentyl)oxy]-2-naphthyl}methyl)({5-[2-(trifluoromethyl)phenyl]-2-furyl}methyl)amino]ethanol HPLC retention time (minute): 4.15;
MS: 588 (M+H)⁺, 303.

EXAMPLE 63-53

2-[({5-[2-chloro-5-(trifluoromethyl)phenyl]-2-furyl}methyl)({6-[(5-phenylpentyl)oxy]-2-naphthyl}methyl)amino]ethanol HPLC retention time (minute): 4.24;
MS: 622 (M+H)⁺, 303.

EXAMPLE 63-54

2-[({6-[(5-phenylpentyl)oxy]-2-naphthyl}methyl)({5-[2-(trifluoromethoxy)phenyl]-2-furyl}methyl)amino]ethanol HPLC retention time (minute): 4.21;
MS: 604 (M+H)⁺, 303.

EXAMPLE 63-55

2-[[4-(dimethylamino)benzyl]({6-[(5-phenylpentyl)oxy]-2-naphthyl}methyl)amino]ethanol HPLC retention time (minute): 3.82;
MS: 497 (M+H)⁺, 353, 304, 195, 134.

EXAMPLE 63-56

2-[({6-[(5-phenylpentyl)oxy]-2-naphthyl}methyl)(4-pyridinylmethyl)amino]ethanol

HPLC retention time (minute): 3.56;
MS: 455 (M+H)⁺, 303, 153.

EXAMPLE 63-57

2-[({6-[(5-phenylpentyl)oxy]-2-naphthyl}methyl)(2-quinolinylmethyl)amino]ethanol HPLC retention time (minute): 4.04;
MS: 505 (M+H)⁺.

EXAMPLE 63-58

2-[[(3,5-dimethyl-1-phenyl-1H-pyrazol-4-yl)methyl]({6-[(5-phenylpentyl)oxy]-2-naphthyl}methyl)amino]ethanol HPLC retention time (minute): 3.99;
MS: 548 (M+H)⁺, 185

EXAMPLE 63-59

2-[[(4-methyl-1H-imidazol-5-yl)methyl]({6-[(5-phenylpentyl)oxy]-2-naphthyl}methyl)amino]ethanol HPLC retention time (minute): 3.56;
MS: 458 (M+H)$^+$, 364, 303.

EXAMPLE 63-60

2-[[(2-phenyl-1H-imidazol-5-yl)methyl]({6-[(5-phenylpentyl)oxy]-2-naphthyl}methyl)amino]ethanol HPLC retention time (minute): 3.71;
MS: 520 (M+H)$^+$.

EXAMPLE 63-61

2-{({6-[(5-phenylpentyl)oxy]-2-naphthyl}methyl)[(3-phenyl-1H-pyrazol-4-yl)methyl]amino}ethanol HPLC retention time (minute): 3.86;
MS: 520 (M+H)$^+$.

EXAMPLE 64-1 TO EXAMPLE 64-39

The procedure of Example 4 was followed but using a corresponding sulfonamide compound as a substitute for benzenesulfonamide. Thus, the compound of the present invention having the following physical properties was obtained.

EXAMPLE 64-1

3-methyl-N-[3-({3-[4-(3-phenylpropoxy)phenyl]propyl}amino)propanoyl]benzenesulfonamide HPLC retention time (minute): 3.74;
MS: 989 (2M+H)$^+$, 495 (M+H)$^+$.

EXAMPLE 64-2

4-methyl-N-[3-({3-[4-(3-phenylpropoxy)phenyl]propyl}amino)propanoyl]benzenesulfonamide HPLC retention time (minute): 3.76;
MS: 989 (2M+H)$^+$, 495 (M+H)$^+$.

EXAMPLE 64-3

2-chloro-N-[3-({3-[4-(3-phenylpropoxy)phenyl]propyl}amino)propanoyl]benzenesulfonamide HPLC retention time (minute): 3.71;
MS: 517, 515 (M+H)$^+$.

EXAMPLE 64-4

3-chloro-N-[3-({3-[4-(3-phenylpropoxy)phenyl]propyl}amino)propanoyl]benzenesulfonamide HPLC retention time (minute): 3.78;
MS: 517, 515 (M+H)$^+$.

EXAMPLE 64-5

4-chloro-N-[3-({3-[4-(3-phenylpropoxy)phenyl]propyl}amino)propanoyl]benzenesulfonamide HPLC retention time (minute): 3.79;
MS: 517, 515 (M+H)$^+$.

EXAMPLE 64-6

2-fluoro-N-[3-({3-[4-(3-phenylpropoxy)phenyl]propyl}amino)propanoyl]benzenesulfonamide HPLC retention time (minute): 3.69;
MS: 997 (2M+H)$^+$, 499 (M+H)$^+$.

EXAMPLE 64-7

3-fluoro-N-[3-({3-[4-(3-phenylpropoxy)phenyl]propyl}amino)propanoyl]benzenesulfonamide HPLC retention time (minute): 3.75;
MS: 997 (2M+H)$^+$, 499 (M+H)$^+$.

EXAMPLE 64-8

4-fluoro-N-[3-({3-[4-(3-phenylpropoxy)phenyl]propyl}amino)propanoyl]benzenesulfonamide HPLC retention time (minute): 3.73;
MS: 997 (2M+H)$^+$, 499 (M+H)$^+$.

EXAMPLE 64-9

N-[3-({3-[4-(3-phenylpropoxy)phenyl]propyl}amino)propanoyl]-2-(trifluoromethyl)benzenesulfonamide HPLC retention time (minute): 3.76;
MS: 549 (M+H)$^+$.

EXAMPLE 64-10

N-[4-({[3-({3-[4-(3-phenylpropoxy)phenyl]propyl}amino)propanoyl]amino}sulfonyl)phenyl]acetamide HPLC retention time (minute): 3.59;
MS: 538 (M+H)$^+$.

EXAMPLE 64-11

N-[3-({3-[4-(3-phenylpropoxy)phenyl]propyl}amino)propanoyl]methanesulfonamide

HPLC retention time (minute): 3.53;
MS: 837 (2M+H)$^+$, 419 (M+H)$^+$.

EXAMPLE 64-12

N-[3-({3-[4-(3-phenylpropoxy)phenyl]propyl}amino)propanoyl]ethanesulfonamide

HPLC retention time (minute): 3.58;
MS: 865 (2M+H)$^+$, 433 (M+H)$^+$.

EXAMPLE 64-13

5-methyl-N-[3-({3-[4-(3-phenylpropoxy)phenyl]propyl}amino)propanoyl]-2-pyridinesulfonamide HPLC retention time (minute): 3.65;
MS: 991 (2M+H)$^+$, 496 (M+H)$^+$.

EXAMPLE 64-14

5-chloro-N-[3-({3-[4-(3-phenylpropoxy)phenyl]propyl}amino)propanoyl]-2-thiophenesulfonamide HPLC retention time (minute): 3.78;
MS: 523, 521 (M+H)$^+$.

EXAMPLE 64-15

N-[3-({3-[4-(3-phenylpropoxy)phenyl]propyl}amino)propanoyl]-2-(trifluoromethoxy)benzenesulfonamide HPLC retention time (minute): 3.78;
MS: 565 (M+H)$^+$.

EXAMPLE 64-16

3-cyano-N-[3-({3-[4-(3-phenylpropoxy)phenyl]propyl}amino)propanoyl]benzenesulfonamide HPLC retention time (minute): 3.71;
MS: 506 (M+H)$^+$, 370.

EXAMPLE 64-17

N-[3-({3-[4-(3-phenylpropoxy)phenyl]propyl}amino)propanoyl]-3-(trifluoromethyl)benzenesulfonamide HPLC retention time (minute): 3.83;
MS: 549 (M+H)$^+$.

EXAMPLE 64-18

4-t-butyl-N-[3-({3-[4-(3-phenylpropoxy)phenyl]propyl}amino)propanoyl]benzenesulfonamide HPLC retention time (minute): 3.93;
MS: 537 (M+H)$^+$.

EXAMPLE 64-19

N-[3-({3-[4-(3-phenylpropoxy)phenyl]propyl}amino)propanoyl]-4-vinylbenzenesulfonamide HPLC retention time (minute): 3.78;
MS: 507 (M+H)$^+$.

EXAMPLE 64-20

2-methyl-N-[3-({3-[4-(3-phenylpropoxy)phenyl]propyl}amino)propanoyl]-2-propanesulfonamide HPLC retention time (minute): 3.62;
MS: 921 (2M+H)$^+$, 461 (M+H)$^+$.

EXAMPLE 64-21

(+)-1-(7,7-dimethyl-2-oxobicyclo[2.2.1]hept-1-yl)-N-[3-({3-[4-(3-phenylpropoxy)phenyl]propyl}amino)propanoyl]methanesulfonamide HPLC retention time (minute): 3.77;
MS: 555 (M+H)$^+$.

EXAMPLE 64-22

(−)-1-(7,7-dimethyl-2-oxobicyclo[2.2.1]hept-1-yl)-N-[3-({3-[4-(3-phenylpropoxy)phenyl]propyl}amino)propanoyl]methanesulfonamide HPLC retention time (minute): 3.77;
MS: 555 (M+H)$^+$.

EXAMPLE 64-23

3-chloro-2-methyl-N-[3-({3-[4-(3-phenylpropoxy)phenyl]propyl}amino)propanoyl]benzenesulfonamide HPLC retention time (minute): 3.81;
MS: 531, 529 (M+H)$^+$.

EXAMPLE 64-24

3-fluoro-4-methyl-N-[3-({3-[4-(3-phenylpropoxy)phenyl]propyl}amino)propanoyl]benzenesulfonamide HPLC retention time (minute): 3.79;
MS: 513 (M+H)$^+$.

EXAMPLE 64-25

3,5-difluoro-N-[3-({3-[4-(3-phenylpropoxy)phenyl]propyl}amino)propanoyl]benzenesulfonamide HPLC retention time (minute): 3.78;
MS: 517 (M+H)$^+$.

EXAMPLE 64-26

2,4-difluoro-N-[3-({3-[4-(3-phenylpropoxy)phenyl]propyl}amino)propanoyl]benzenesulfonamide HPLC retention time (minute): 3.72;
MS: 517 (M+H)$^+$.

EXAMPLE 64-27

2,5-difluoro-N-[3-({3-[4-(3-phenylpropoxy)phenyl]propyl}amino)propanoyl]benzenesulfonamide HPLC retention time (minute): 3.73;
MS: 517 (M+H)$^+$.

EXAMPLE 64-28

2,6-difluoro-N-[3-({3-[4-(3-phenylpropoxy)phenyl]propyl}amino)propanoyl]benzenesulfonamide HPLC retention time (minute): 3.69;
MS: 517 (M+H)$^+$.

EXAMPLE 64-29

3,4-difluoro-N-[3-({3-[4-(3-phenylpropoxy)phenyl]propyl}amino)propanoyl]benzenesulfonamide HPLC retention time (minute): 3.76;
MS: 517 (M+H)$^+$.

EXAMPLE 64-30

2-methoxy-4-methyl-N-[3-({3-[4-(3-phenylpropoxy)phenyl]propyl}amino)propanoyl]benzenesulfonamide HPLC retention time (minute): 3.74;
MS: 525 (M+H)$^+$, 370.

EXAMPLE 64-31

3-chloro-4-methyl-N-[3-({3-[4-(3-phenylpropoxy)phenyl]propyl}amino)propanoyl]benzenesulfonamide HPLC retention time (minute): 3.84;
MS: 531, 529 (M+H)$^+$.

EXAMPLE 64-32

2,5-dimethoxy-N-[3-({3-[4-(3-phenylpropoxy)phenyl]propyl}amino)propanoyl]benzenesulfonamide HPLC retention time (minute): 3.70;
MS: 541 (M+H)$^+$, 370.

EXAMPLE 64-33

5-chloro-2-fluoro-N-[3-({3-[4-(3-phenylpropoxy)phenyl]propyl}amino)propanoyl]benzenesulfonamide HPLC retention time (minute): 3.80;
MS: 535, 533 (M+H)$^+$.

EXAMPLE 64-34

3-chloro-2-fluoro-N-[3-({3-[4-(3-phenylpropoxy)phenyl]propyl}amino)propanoyl]benzenesulfonamide HPLC retention time (minute): 3.77;
MS: 535, 533 (M+H)$^+$.

EXAMPLE 64-35

2,6-dichloro-N-[3-({3-[4-(3-phenylpropoxy)phenyl]propyl}amino)propanoyl]benzenesulfonamide HPLC retention time (minute): 3.76;
MS: 551, 549 (M+H)$^+$.

EXAMPLE 64-36

N-[3-({3-[4-(3-phenylpropoxy)phenyl]propyl}amino)propanoyl]-3-thiophenesulfonamide HPLC retention time (minute): 3.66;
MS: 973 (2M+H)$^+$, 487 (M+H)$^+$, 370.

EXAMPLE 64-37

5-chloro-N-[3-({3-[4-(3-phenylpropoxy)phenyl]propyl}amino)propanoyl]-3-thiophenesulfonamide HPLC retention time (minute): 3.79;
MS: 523, 521 (M+H)$^+$.

EXAMPLE 64-38

6-chloro-N-[3-({3-[4-(3-phenylpropoxy)phenyl]propyl}amino)propanoyl]-3-pyridinesulfonamide HPLC retention time (minute): 3.73;
MS: 518, 516 (M+H)$^+$.

EXAMPLE 64-39

3,5-dimethyl-N-[3-({3-[4-(3-phenylpropoxy)phenyl]propyl}amino)propanoyl]-4-isoxazolesulfonamide HPLC retention time (minute): 3.71;
MS: 500 (M+H)$^+$.

EXAMPLE 65-1 TO EXAMPLE 65-54

The procedure of Example 5 was followed but using 6-(4-phenylpentyloxy)-2-formylnaphthalene as a substitute for 6-(4-phenylbutoxy)-2-formylnaphthalene while using a corresponding amine compound as a substitute for piperidine. Thus, the compound of the present invention having the following physical properties was obtained.

EXAMPLE 65-1

1-({6-[(5-phenylpentyl)oxy]-2-naphthyl}methyl)azocane

HPLC retention time (minute): 4.02;
MS: 416 (M+H)$^+$.

EXAMPLE 65-2

3-({6-[(5-phenylpentyl)oxy]-2-naphthyl}methyl)-1,3-thiazolidine

HPLC retention time (minute): 3.89;
MS: 392 (M+H)$^+$, 303.

EXAMPLE 65-3

1-({6-[(5-phenylpentyl)oxy]-2-naphthyl}methyl)-2,5-dihydro-1H-pyrrole

HPLC retention time (minute): 3.86;
MS: 372 (M+H)$^+$, 303.

EXAMPLE 65-4

[(2S)-1-({6-[(5-phenylpentyl)oxy]-2-naphthyl}methyl)-2-pyrrolidinyl]methanol

HPLC retention time (minute): 3.80;
MS: 404 (M+H)$^+$, 303.

EXAMPLE 65-5

1-({6-[(5-phenylpentyl)oxy]-2-naphthyl}methyl)-3-pyrrolidinol

HPLC retention time (minute): 3.78;
MS: 390 (M+H)+, 303.

EXAMPLE 65-6

[1-({6-[(5-phenylpentyl)oxy]-2-naphthyl}methyl)-2-piperidinyl]methanol

HPLC retention time (minute): 3.86;
MS: 418 (M+H)+, 303.

EXAMPLE 65-7

1-({6-[(5-phenylpentyl)oxy]-2-naphthyl}methyl)-3-piperidinecarboxamide

HPLC retention time (minute): 3.77;
MS: 431 (M+H)+, 303.

EXAMPLE 65-8

3-methyl-1-({6-[(5-phenylpentyl)oxy]-2-naphthyl}methyl)piperidine

HPLC retention time (minute): 3.95;
MS: 402 (M+H)+.

EXAMPLE 65-9

3,5-dimethyl-1-({6-[(5-phenylpentyl)oxy]-2-naphthyl}methyl)piperidine

HPLC retention time (minute): 4.02;
MS: 416 (M+H)+.

EXAMPLE 65-10

[1-({6-[(5-phenylpentyl)oxy]-2-naphthyl}methyl)-3-piperidinyl]methanol

HPLC retention time (minute): 3.78;
MS: 418 (M+H)+.

EXAMPLE 65-11

4-methyl-1-({6-[(5-phenylpentyl)oxy]-2-naphthyl}methyl)piperidine

HPLC retention time (minute): 3.97;
MS: 402 (M+H)+.

EXAMPLE 65-12

2-[1-({6-[(5-phenylpentyl)oxy]-2-naphthyl}methyl)-4-piperidinyl]ethanol

HPLC retention time (minute): 3.80;
MS: 432 (M+H)+.

EXAMPLE 65-13

1-({6-[(5-phenylpentyl)oxy]-2-naphthyl}methyl)-4-(2-pyridinyl)piperazine

HPLC retention time (minute): 3.60;
MS: 466 (M+H)+, 303.

EXAMPLE 65-14

1-({6-[(5-phenylpentyl)oxy]-2-naphthyl}methyl)azepane

HPLC retention time (minute): 3.97;
MS: 402 (M+H)+.

EXAMPLE 65-15

(2S)-2-(methoxymethyl)-1-({6-[(5-phenylpentyl)oxy]-2-naphthyl}methyl)pyrrolidine HPLC retention time (minute): 3.91;
MS: 418 (M+H)+, 303.

EXAMPLE 65-16

2-({6-[(5-phenylpentyl)oxy]-2-naphthyl}methyl)decahydroisoquinoline

HPLC retention time (minute): 4.10;
MS: 442 (M+H)+.

EXAMPLE 65-17

(2S)-1-({6-[(5-phenylpentyl)oxy]-2-naphthyl}methyl)-2-(1-pyrrolidinylmethyl)pyrrolidine HPLC retention time (minute): 3.58;
MS: 457 (M+H)+, 303, 159.

EXAMPLE 65-18

1-({6-[(5-phenylpentyl)oxy]-2-naphthyl}methyl)-3-piperidinol

HPLC retention time (minute): 3.78;
MS: 404 (M+H)+, 303.

EXAMPLE 65-19

1-({6-[(5-phenylpentyl)oxy]-2-naphthyl}methyl)-4-piperidinecarboxamide

HPLC retention time (minute): 3.73;
MS: 431 (M+H)+, 303.

EXAMPLE 65-20

2-[4-({6-[(5-phenylpentyl)oxy]-2-naphthyl}methyl)-1-piperazinyl]pyrimidine

HPLC retention time (minute): 3.91;
MS: 467 (M+H)+, 303, 165.

EXAMPLE 65-21

N-[1-({6-[(5-phenylpentyl)oxy]-2-naphthyl}methyl)-3-pyrrolidinyl]acetamide

HPLC retention time (minute): 3.75;
MS: 431 (M+H)$^+$, 303.

EXAMPLE 65-22

N-methyl-N-[1-({6-[(5-phenylpentyl)oxy]-2-naphthyl}methyl)-3-pyrrolidinyl]acetamide HPLC retention time (minute): 3.82;
MS: 445 (M+H)$^+$, 303.

EXAMPLE 65-23

N-ethyl-N-[1-({6-[(5-phenylpentyl)oxy]-2-naphthyl}methyl)-3-pyrrolidinyl]acetamide HPLC retention time (minute): 3.89;
MS: 459 (M+H)$^+$.

EXAMPLE 65-24

1-({6-[(5-phenylpentyl)oxy]-2-naphthyl}methyl)-3-pyrrolidinamine

HPLC retention time (minute): 3.55;
MS: 389 (M+H)$^+$, 303.

EXAMPLE 65-25

1-methyl-4-({6-[(5-phenylpentyl)oxy]-2-naphthyl}methyl)-1,4-diazepane

HPLC retention time (minute): 3.55;
MS: 417 (M+H)$^+$, 303.

EXAMPLE 65-26

1-ethyl-4-({6-[(5-phenylpentyl)oxy]-2-naphthyl}methyl)piperazine

HPLC retention time (minute): 3.60;
MS: 417 (M+H)$^+$, 303.

EXAMPLE 65-27

[(2R)-1-({6-[(5-phenylpentyl)oxy]-2-naphthyl}methyl)-2-pyrrolidinyl]methanol

HPLC retention time (minute): 3.80;
MS: 404 (M+H)$^+$, 303.

EXAMPLE 65-28

(2R)-2-(methoxymethyl)-1-({6-[(5-phenylpentyl)oxy]-2-naphthyl}methyl)pyrrolidine HPLC retention time (minute): 3.93;
MS: 418 (M+H)$^+$, 303.

EXAMPLE 65-29

N-[(3R)-1-({6-[(5-phenylpentyl)oxy]-2-naphthyl}methyl)-3-pyrrolidinyl]acetamide

HPLC retention time (minute): 3.75;
MS: 431 (M+H)$^+$, 303.

EXAMPLE 65-30

N-[(3S)-1-({6-[(5-phenylpentyl)oxy]-2-naphthyl}methyl)-3-pyrrolidinyl]acetamide

HPLC retention time (minute): 3.75;
MS: 431 (M+H)$^+$.

EXAMPLE 65-31 cis-2-({6-[(5-phenylpentyl)oxy]-2-naphthyl}methyl)decahydroisoquinoline

HPLC retention time (minute): 4.08;
MS: 442 (M+H)$^+$.

EXAMPLE 65-32

(3R)-1-({6-[(5-phenylpentyl)oxy]-2-naphthyl}methyl)-3-pyrrolidinamine

HPLC retention time (minute): 3.55;
MS: 389 (M+H)$^+$.

EXAMPLE 65-33

(3S)-1-({6-[(5-phenylpentyl)oxy]-2-naphthyl}methyl)-3-pyrrolidinamine

HPLC retention time (minute): 3.55;
MS: 389 (M+H)$^+$.

EXAMPLE 65-34

(3S)-N,N-dimethyl-1-({6-[(5-phenylpentyl)oxy]-2-naphthyl}methyl)-3-pyrrolidinamine HPLC retention time (minute): 3.56;
MS: 417 (M+H)$^+$, 303.

EXAMPLE 65-35

N-methyl-1-({6-[(5-phenylpentyl)oxy]-2-naphthyl}methyl)-3-pyrrolidinamine

HPLC retention time (minute): 3.58;
MS: 403 (M+H)$^+$, 303.

EXAMPLE 65-36

N,N-dimethyl-1-({6-[(5-phenylpentyl)oxy]-2-naphthyl}methyl)-3-pyrrolidinamine

MS: 417 (M+H)$^+$, 303.

EXAMPLE 65-37

3-[1-({6-[(5-phenylpentyl)oxy]-2-naphthyl}methyl)-4-piperidinyl]phenol

HPLC retention time (minute): 3.97;
MS: 480 (M+H)+, 303.

EXAMPLE 65-38

N,N-diethyl-1-({6-[(5-phenylpentyl)oxy]-2-naphthyl}methyl)-3-pyrrolidinamine

HPLC retention time (minute): 3.62;
MS: 445 (M+H)+, 303.

EXAMPLE 65-39

2,5-dimethyl-1-({6-[(5-phenylpentyl)oxy]-2-naphthyl}methyl)pyrrolidine

HPLC retention time (minute): 3.95;
MS: 402 (M+H)+.

EXAMPLE 65-40

1-({6-[(5-phenylpentyl)oxy]-2-naphthyl}methyl)-1,2,3,6-tetrahydropyridine

HPLC retention time (minute): 3.89;
MS: 386 (M+H)+, 303.

EXAMPLE 65-41

N,N-diethyl-1-({6-[(5-phenylpentyl)oxy]-2-naphthyl}methyl)-3-piperidinecarboxamide HPLC retention time (minute): 3.99;
MS: 487 (M+H)+.

EXAMPLE 65-42

2-methyl-1-({6-[(5-phenylpentyl)oxy]-2-naphthyl}methyl)pyrrolidine

HPLC retention time (minute): 3.91;
MS: 388 (M+H)+.

EXAMPLE 65-43

(3R)-1-({6-[(5-phenylpentyl)oxy]-2-naphthyl}methyl)-3-pyrrolidinol

HPLC retention time (minute): 3.77;
MS: 390 (M+H)+, 303.

EXAMPLE 65-44

[1-({6-[(5-phenylpentyl)oxy]-2-naphthyl}methyl)-4-piperidinyl]methanol

HPLC retention time (minute): 3.78;
MS: 418 (M+H)+.

EXAMPLE 65-45

1-({6-[(5-phenylpentyl)oxy]-2-naphthyl}methyl)-1,4-diazepane

HPLC retention time (minute): 3.55;
MS: 403 (M+H)+, 303.

EXAMPLE 65-46

(1R,4R)-2-({6-[(5-phenylpentyl)oxy]-2-naphthyl}methyl)-2,5-diazabicyclo[2.2.1]heptane HPLC retention time (minute): 3.55;
MS: 401 (M+H)+, 303.

EXAMPLE 65-47

2-[4-({6-[(5-phenylpentyl)oxy]-2-naphthyl}methyl)-1-piperazinyl]benzonitrile

HPLC retention time (minute): 3.99;
MS: 490 (M+H)+, 303.

EXAMPLE 65-48

4-({6-[(5-phenylpentyl)oxy]-2-naphthyl}methyl)-1,4-diazepane-1-carbaldehyde

HPLC retention time (minute): 3.69;
MS: 431 (M+H)+, 303.

EXAMPLE 65-49

4-({6-[(5-phenylpentyl)oxy]-2-naphthyl}methyl)-2-piperazinone

HPLC retention time (minute): 3.67;
MS: 805 (2M+H)+, 403 (M+H)+, 303.

EXAMPLE 65-50

(2S)-N,N-dimethyl-1-({6-[(5-phenylpentyl)oxy]-2-naphthyl}methyl)-2-pyrrolidinecarboxamide HPLC retention time (minute): 3.77;
MS: 445 (M+H)+, 303.

EXAMPLE 65-51

2-methyl-3-({6-[(5-phenylpentyl)oxy]-2-naphthyl}methyl)-1,3-thiazolidine

HPLC retention time (minute): 3.89;
MS: 406 (M+H)+, 303.

EXAMPLE 65-52

2-[4-({6-[(5-phenylpentyl)oxy]-2-naphthyl}methyl)-1,4-diazepan-1-yl]ethanol

HPLC retention time (minute): 3.47;
MS: 447 (M+H)+, 303, 145.

EXAMPLE 65-53

3-[1-({6-[(5-phenylpentyl)oxy]-2-naphthyl}methyl)-4-piperidinyl]-1H-indole

HPLC retention time (minute): 4.02;
MS: 503 (M+H)$^+$.

EXAMPLE 65-54

2-[4-({6-[(5-phenylpentyl)oxy]-2-naphthyl}methyl)-1,4-diazepan-1-yl]nicotinonitrile HPLC retention time (minute): 3.97;
MS: 505 (M+H)$^+$.

EXAMPLE 66-1 TO EXAMPLE 66-118

The procedure of Example 37 was followed but using a corresponding amine compound as a substitute for piperidine. Thus, the compound of the present invention having the following physical properties was obtained.

EXAMPLE 66-1

[(2S)-1-({6-[(4-isobutyl-2-methoxybenzyl)oxy]-1-methyl-3,4-dihydro-2-naphthalenyl}methyl)-2-pyrrolidinyl]methanol HPLC retention time (minute): 3.85;
MS: 899 (2M+H)$^+$, 450 (M+H)$^+$, 349, 177.

EXAMPLE 66-2

1-({6-[(4-isobutyl-2-methoxybenzyl)oxy]-1-methyl-3,4-dihydro-2-naphthalenyl}methyl)-3-pyrrolidinol HPLC retention time (minute): 3.80;
MS: 871 (2M+H)$^+$, 436 (M+H)$^+$, 349, 177.

EXAMPLE 66-3

1-({6-[(4-isobutyl-2-methoxybenzyl)oxy]-1-methyl-3,4-dihydro-2-naphthalenyl}methyl)-4-phenylpiperazine HPLC retention time (minute): 4.06;
MS: 511 (M+H)$^+$, 349, 177.

EXAMPLE 66-4

1-({6-[(4-isobutyl-2-methoxybenzyl)oxy]-1-methyl-3,4-dihydro-2-naphthalenyl}methyl)-4-(2-methoxyphenyl)piperazine HPLC retention time (minute): 4.06;
MS: 541 (M+H)$^+$, 349, 177.

EXAMPLE 66-5

4-({6-[(4-isobutyl-2-methoxybenzyl)oxy]-1-methyl-3,4-dihydro-2-naphthalenyl}methyl)-1-piperazinecarbaldehyde HPLC retention time (minute): 3.75;
MS: 925 (2M+H)$^+$, 349, 177

EXAMPLE 66-6 ethyl 4-({6-[(4-isobutyl-2-methoxybenzyl)oxy]-1-methyl-3,4-dihydro-2-naphthalenyl}methyl)-1-piperazinecarboxylate HPLC retention time (minute): 3.92;
MS: 507 (M+H)$^+$, 349, 177.

EXAMPLE 66-7

1-({6-[(4-isobutyl-2-methoxybenzyl)oxy]-1-methyl-3,4-dihydro-2-naphthalenyl}methyl)-4-methylpiperazine HPLC retention time (minute): 3.57;
MS: 897 (2M+H)$^+$, 449 (M+H)$^+$, 349, 177.

EXAMPLE 66-9

4-({6-[(4-isobutyl-2-methoxybenzyl)oxy]-1-methyl-3,4-dihydro-2-naphthalenyl}methyl)morpholine HPLC retention time (minute): 3.85;
MS: 871 (2M+H)$^+$, 349, 177.

EXAMPLE 66-10

4-({6-[(4-isobutyl-2-methoxybenzyl)oxy]-1-methyl-3,4-dihydro-2-naphthalenyl}methyl)thiomorpholine HPLC retention time (minute): 3.93;
MS: 903 (2M+H)$^+$, 349, 177.

EXAMPLE 66-11

1-({6-[(4-isobutyl-2-methoxybenzyl)oxy]-1-methyl-3,4-dihydro-2-naphthalenyl}methyl)piperidine HPLC retention time (minute): 3.94;
MS: 867 (2M+H)$^+$, 434 (M+H)$^+$, 349, 177.

EXAMPLE 66-13

[1-({6-[(4-isobutyl-2-methoxybenzyl)oxy]-1-methyl-3,4-dihydro-2-naphthalenyl}methyl)-2-piperidinyl]methanol HPLC retention time (minute): 3.89;
MS: 464 (M+H)$^+$, 349, 177.

EXAMPLE 66-16

1-({6-[(4-isobutyl-2-methoxybenzyl)oxy]-1-methyl-3,4-dihydro-2-naphthalenyl}methyl)-3-piperidinecarboxamide HPLC retention time (minute): 3.79;
MS: 953 (2M+H)$^+$, 477 (M+H)$^+$, 349, 177.

EXAMPLE 66-17

1-({6-[(4-isobutyl-2-methoxybenzyl)oxy]-1-methyl-3,4-dihydro-2-naphthalenyl}methyl)-3-methylpiperidine HPLC retention time (minute): 4.00;
MS: 895 (2M+H)$^+$, 448 (M+H)$^+$, 349, 177.

EXAMPLE 66-18

1-({6-[(4-isobutyl-2-methoxybenzyl)oxy]-1-methyl-3,4-dihydro-2-naphthalenyl}methyl)-3,5-dimethylpiperidine HPLC retention time (minute): 4.06;
MS: 923 (2M+H)$^+$, 462 (M+H)$^+$, 349, 177.

EXAMPLE 66-20

1-({6-[(4-isobutyl-2-methoxybenzyl)oxy]-1-methyl-3,4-dihydro-2-naphthalenyl}methyl)-4-piperidinol HPLC retention time (minute): 3.79;
MS: 899 (2M+H)$^+$, 450 (M+H)$^+$, 349, 177.

EXAMPLE 66-21

1-({6-[(4-isobutyl-2-methoxybenzyl)oxy]-1-methyl-3,4-dihydro-2-naphthalenyl}methyl)-4-methylpiperidine HPLC retention time (minute): 4.00;
MS: 895 (2M+H)$^+$, 448 (M+H)$^+$, 349, 177.

EXAMPLE 66-22

4-benzyl-1-({6-[(4-isobutyl-2-methoxybenzyl)oxy]-1-methyl-3,4-dihydro-2-naphthalenyl}methyl)piperidine HPLC retention time (minute): 4.15;
MS: 524 (M+H)$^+$, 349, 177.

EXAMPLE 66-24

1-({6-[(4-isobutyl-2-methoxybenzyl)oxy]-1-methyl-3,4-dihydro-2-naphthalenyl}methyl)-4-(2-pyridinyl)piperazine HPLC retention time (minute): 3.63;
MS: 512 (M+H)$^+$, 349, 177.

EXAMPLE 66-25

1-({6-[(4-isobutyl-2-methoxybenzyl)oxy]-1-methyl-3,4-dihydro-2-naphthalenyl}methyl)decahydroquinoline HPLC retention time (minute): 4.12;
MS: 975 (2M+H)$^+$, 488 (M+H)$^+$, 349, 177.

EXAMPLE 66-26

2-({6-[(4-isobutyl-2-methoxybenzyl)oxy]-1-methyl-3,4-dihydro-2-naphthalenyl}methyl)-1,2,3,4-tetrahydroisoquinoline HPLC retention time (minute): 4.04;
MS: 963 (2M+H)$^+$, 482 (M+H)$^+$, 349, 177.

EXAMPLE 66-27

1-({6-[(4-isobutyl-2-methoxybenzyl)oxy]-1-methyl-3,4-dihydro-2-naphthalenyl}methyl)azepane HPLC retention time (minute): 4.00;
MS: 895 (2M+H)$^+$, 448 (M+H)$^+$, 349, 177.

EXAMPLE 66-28

(2S)-1-({6-[(4-isobutyl-2-methoxybenzyl)oxy]-1-methyl-3,4-dihydro-2-naphthalenyl}methyl)-2-(methoxymethyl)pyrrolidine HPLC retention time (minute): 3.97;
MS: 464 (M+H)$^+$, 349, 177.

EXAMPLE 66-29

2-({6-[(4-isobutyl-2-methoxybenzyl)oxy]-1-methyl-3,4-dihydro-2-naphthalenyl}methyl)decahydroisoquinoline HPLC retention time (minute): 4.12;
MS: 975 (2M+H)$^+$, 488 (M+H)$^+$, 349, 177.

EXAMPLE 66-30

(2S)-1-({6-[(4-isobutyl-2-methoxybenzyl)oxy]-1-methyl-3,4-dihydro-2-naphthalenyl}methyl)-2-(1-pyrrolidinylmethyl)pyrrolidine HPLC retention time (minute): 3.59;
MS: 503 (M+H)$^+$, 349, 177.

EXAMPLE 66-32

N-{[(2S)-1-({6-[(4-isobutyl-2-methoxybenzyl)oxy]-1-methyl-3,4-dihydro-2-naphthalenyl}methyl)-2-pyrrolidinyl]methyl}aniline HPLC retention time (minute): 4.11;
MS: 525 (M+H)$^+$, 349, 177.

EXAMPLE 66-33

1-({6-[(4-isobutyl-2-methoxybenzyl)oxy]-1-methyl-3,4-dihydro-2-naphthalenyl}methyl)-4-piperidinecarboxamide HPLC retention time (minute): 3.74;
MS: 953 (2M+H)$^+$, 477 (M+H)$^+$, 349, 177.

EXAMPLE 66-34

1-(2-chlorophenyl)-4-({6-[(4-isobutyl-2-methoxybenzyl)oxy]-1-methyl-3,4-dihydro-2-naphthalenyl}methyl)piperazine HPLC retention time (minute): 4.15;
MS: 545 (M+H)$^+$, 349, 177.

EXAMPLE 66-35

2-[4-({6-[(4-isobutyl-2-methoxybenzyl)oxy]-1-methyl-3,4-dihydro-2-naphthalenyl}methyl)-1-piperazinyl]pyrimidine HPLC retention time (minute): 3.95;
MS: 513 (M+H)$^+$, 349, 177.

EXAMPLE 66-36

1-({6-[(4-isobutyl-2-methoxybenzyl)oxy]-1-methyl-3,4-dihydro-2-naphthalenyl}methyl)azonane HPLC retention time (minute): 4.11;
MS: 476 (M+H)$^+$, 349, 177.

EXAMPLE 66-37

1-acetyl-4-({6-[(4-isobutyl-2-methoxybenzyl)oxy]-1-methyl-3,4-dihydro-2-naphthalenyl}methyl)piperazine HPLC retention time (minute): 3.76;
MS: 953 (2M+H)$^+$, 349, 177.

EXAMPLE 66-38

N-[1-({6-[(4-isobutyl-2-methoxybenzyl)oxy]-1-methyl-3,4-dihydro-2-naphthalenyl}methyl)-3-pyrrolidinyl]acetamide HPLC retention time (minute): 3.78;
MS: 953 (2M+H)$^+$, 477 (M+H)$^+$, 349, 177.

EXAMPLE 66-39

N-[1-({6-[(4-isobutyl-2-methoxybenzyl)oxy]-1-methyl-3,4-dihydro-2-naphthalenyl}methyl)-3-pyrrolidinyl]-N-methylacetamide HPLC retention time (minute): 3.86;
MS: 491 (M+H)$^+$, 349, 177.

EXAMPLE 66-40

N-ethyl-N-[1-({6-[(4-isobutyl-2-methoxybenzyl)oxy]-1-methyl-3,4-dihydro-2-naphthalenyl}methyl)-3-pyrrolidinyl]acetamide HPLC retention time (minute): 3.95;
MS: 505 (M+H)$^+$, 349, 177.

EXAMPLE 66-41 t-butyl [1-({6-[(4-isobutyl-2-methoxybenzyl)oxy]-1-methyl-3,4-dihydro-2-naphthalenyl}methyl)-3-pyrrolidinyl]carbamate HPLC retention time (minute): 4.04;
MS: 535 (M+H)$^+$, 349, 177.

EXAMPLE 66-42

1-({6-[(4-isobutyl-2-methoxybenzyl)oxy]-1-methyl-3,4-dihydro-2-naphthalenyl}methyl)-4-methyl-1,4-diazepane HPLC retention time (minute): 3.55;
MS: 463 (M+H)$^+$, 349, 177.

EXAMPLE 66-43

1-ethyl-4-({6-[(4-isobutyl-2-methoxybenzyl)oxy]-1-methyl-3,4-dihydro-2-naphthalenyl}methyl)piperazine HPLC retention time (minute): 3.59;
MS: 925 (2M+H)$^+$, 463 (M+H)$^+$, 349, 177.

EXAMPLE 66-44

[(2R)-1-({6-[(4-isobutyl-2-methoxybenzyl)oxy]-1-methyl-3,4-dihydro-2-naphthalenyl}methyl)-2-pyrrolidinyl]methanol HPLC retention time (minute): 3.85;
MS: 450 (M+H)$^+$, 349, 177.

EXAMPLE 66-45

4-[4-({6-[(4-isobutyl-2-methoxybenzyl)oxy]-1-methyl-3,4-dihydro-2-naphthalenyl}methyl)-1-piperazinyl]phenol HPLC retention time (minute): 3.91;
MS: 527 (M+H)$^+$, 349, 177.

EXAMPLE 66-46

(2R)-1-({6-[(4-isobutyl-2-methoxybenzyl)oxy]-1-methyl-3,4-dihydro-2-naphthalenyl}methyl)-2-(methoxymethyl)pyrrolidine HPLC retention time (minute): 3.97;
MS: 886 (2M+H)$^+$, 420 (M+H)$^+$, 349, 177.

EXAMPLE 66-48 rel-(4aR,8aS)-2-({6-[(4-isobutyl-2-methoxybenzyl)oxy]-1-methyl-3,4-dihydro-2-naphthalenyl}methyl)decahydroisoquinoline HPLC retention time (minute): 4.12;
MS: 975 (2M+H)$^+$, 488 (M+H)$^+$, 349, 177.

EXAMPLE 66-50 rel-(2R,6S)-4-({6-[(4-isobutyl-2-methoxybenzyl)oxy]-1-methyl-3,4-dihydro-2-naphthalenyl}methyl)-2,6-dimethylmorpholine HPLC retention time (minute): 3.96;
MS: 927 (2M+H)$^+$, 464 (M+H)$^+$, 349, 177.

EXAMPLE 66-51

N-[(3R)-1-({6-[(4-isobutyl-2-methoxybenzyl)oxy]-1-methyl-3,4-dihydro-2-naphthalenyl}methyl)-3-pyrrolidinyl]acetamide HPLC retention time (minute): 3.79;
MS: 953 (2M+H)$^+$, 477 (M+H)$^+$, 349, 177.

EXAMPLE 66-52

N-[(3S)-1-({6-[(4-isobutyl-2-methoxybenzyl)oxy]-1-methyl-3,4-dihydro-2-naphthalenyl}methyl)-3-pyrrolidinyl]acetamide HPLC retention time (minute): 3.79;
MS: 953 (2M+H)$^+$, 477 (M+H)$^+$, 349, 177.

EXAMPLE 66-53 t-butyl [(3R)-1-({6-[(4-isobutyl-2-methoxybenzyl)oxy]-1-methyl-3,4-dihydro-2-naphthalenyl}methyl)-3-pyrrolidinyl]carbamate HPLC retention time (minute): 4.05;
MS: 535 (M+H)$^+$, 349, 177.

EXAMPLE 66-54 t-butyl [(3S)-1-({6-[(4-isobutyl-2-methoxybenzyl)oxy]-1-methyl-3,4-dihydro-2-naphthalenyl}methyl)-3-pyrrolidinyl]carbamate HPLC retention time (minute): 4.05;
MS: 535 (M+H)$^+$, 349, 177.

EXAMPLE 66-55

(3R)-1-({6-[(4-isobutyl-2-methoxybenzyl)oxy]-1-methyl-3,4-dihydro-2-naphthalenyl}methyl)-N,N-dimethyl-3-pyrrolidinamine HPLC retention time (minute): 3.59;
MS: 925 (2M+H)$^+$, 463 (M+H)$^+$, 349, 177.

EXAMPLE 66-56

(3S)-1-({6-[(4-isobutyl-2-methoxybenzyl)oxy]-1-methyl-3,4-dihydro-2-naphthalenyl}methyl)-N,N-dimethyl-3-pyrrolidinamine HPLC retention time (minute): 3.59;
MS: 925 (2M+H)$^+$, 463 (M+H)$^+$, 349, 177.

EXAMPLE 66-57

1-({6-[(4-isobutyl-2-methoxybenzyl)oxy]-1-methyl-3,4-dihydro-2-naphthalenyl}methyl)-N,N-dimethyl-3-pyrrolidinamine HPLC retention time (minute): 3.59;
MS: 925 (2M+H)$^+$, 463 (M+H)$^+$, 349, 177.

EXAMPLE 66-58

[(3S)-2-({6-[(4-isobutyl-2-methoxybenzyl)oxy]-1-methyl-3,4-dihydro-2-naphthalenyl}methyl)-1,2,3,4-tetarahydro-3-isoquinolinyl]methanol HPLC retention time (minute): 4.01;
MS: 512 (M+H)$^+$, 349, 177.

EXAMPLE 66-59

3-[1-({6-[(4-isobutyl-2-methoxybenzyl)oxy]-1-methyl-3,4-dihydro-2-naphthalenyl}methyl)-4-piperidinyl]phenol HPLC retention time (minute): 3.99;
MS: 526 (M+H)$^+$, 349, 177.

EXAMPLE 66-60

N,N-diethyl-1-({6-[(4-isobutyl-2-methoxybenzyl)oxy]-1-methyl-3,4-dihydro-2-naphthalenyl}methyl)-3-pyrrolidinamine HPLC retention time (minute): 3.63;
MS: 981 (2M+H)$^+$, 491 (M+H)$^+$, 349, 177.

EXAMPLE 66-61

2-({6-[(4-isobutyl-2-methoxybenzyl)oxy]-1-methyl-3,4-dihydro-2-naphthalenyl}methyl)-2,3,4,9-tetrahydro-1H-β-carboline HPLC retention time (minute): 4.07;
MS: 521 (M+H)$^+$, 349, 177.

EXAMPLE 66-62

1-({6-[(4-isobutyl-2-methoxybenzyl)oxy]-1-methyl-3,4-dihydro-2-naphthalenyl}methyl)azetidine HPLC retention time (minute): 3.91;
MS: 811 (2M+H)$^+$, 406 (M+H)$^+$, 349, 177.

EXAMPLE 66-63

1-({6-[(4-isobutyl-2-methoxybenzyl)oxy]-1-methyl-3,4-dihydro-2-naphthalenyl}methyl)-2,5-dimethyl-2,5-dihydro-1H-pyrrole HPLC retention time (minute): 3.97;
MS: 446 (2M+H)$^+$, 420 (M+H)$^+$, 349, 177.

EXAMPLE 66-64

(2S)-1-({6-[(4-isobutyl-2-methoxybenzyl)oxy]-1-methyl-3,4-dihydro-2-naphthalenyl}methyl)-2-pyrrolidinecarboxamide HPLC retention time (minute): 3.79;
MS: 925 (2M+H)$^+$, 463 (M+H)$^+$, 349, 177.

EXAMPLE 66-65

1-({6-[(4-isobutyl-2-methoxybenzyl)oxy]-1-methyl-3,4-dihydro-2-naphthalenyl}methyl)-2,5-dimethylpyrrolidine HPLC retention time (minute): 3.98;
MS: 448 (M+H)$^+$, 349, 177.

EXAMPLE 66-66

1-({6-[(4-isobutyl-2-methoxybenzyl)oxy]-1-methyl-3,4-dihydro-2-naphthalenyl}methyl)-1,2,3,6-tetrahydropyridine HPLC retention time (minute): 3.93;
MS: 863 (2M+H)$^+$, 432 (M+H)$^+$, 349, 177.

EXAMPLE 66-67

1-(4-fluorophenyl)-4-({6-[(4-isobutyl-2-methoxybenzyl)oxy]-1-methyl-3,4-dihydro-2-naphthalenyl}methyl)piperazine HPLC retention time (minute): 4.06;
MS: 529 (M+H)$^+$, 349, 177.

EXAMPLE 66-68

4-({6-[(4-isobutyl-2-methoxybenzyl)oxy]-1-methyl-3,4-dihydro-2-naphthalenyl}methyl)-2,6-dimethylmorpholine HPLC retention time (minute): 3.94;
MS: 927 (2M+H)$^+$, 464 (M+H)$^+$, 349, 177.

EXAMPLE 66-69

8-({6-[(4-isobutyl-2-methoxybenzyl)oxy]-1-methyl-3,4-dihydro-2-naphthalenyl}methyl)-1,4-dioxa-8-azaspiro[4.5]decane:

HPLC retention time (minute): 3.93;
MS: 983 (2M+H)$^+$, 492 (M+H)$^+$, 349, 177.

EXAMPLE 66-70

N,N-diethyl-1-({6-[(4-isobutyl-2-methoxybenzyl)oxy]-1-methyl-3,4-dihydro-2-naphthalenyl}methyl)-3-piperidinecarboxamide HPLC retention time (minute): 4.05;
MS: 533 (M+H)$^+$, 349, 177.

EXAMPLE 66-72

1'-({6-[(4-isobutyl-2-methoxybenzyl)oxy]-1-methyl-3,4-dihydro-2-naphthalenyl}methyl)-1,4'-bipiperidine HPLC retention time (minute): 3.59;
MS: 517 (M+H)$^+$, 349, 177.

EXAMPLE 66-73

1-({6-[(4-isobutyl-2-methoxybenzyl)oxy]-1-methyl-3,4-dihydro-2-naphthalenyl}methyl)-2-methylpyrrolidine HPLC retention time (minute): 3.93;
MS: 867 (2M+H)$^+$, 434 (M+H)$^+$, 349, 177.

EXAMPLE 66-74

1-({6-[(4-isobutyl-2-methoxybenzyl)oxy]-1-methyl-3,4-dihydro-2-naphthalenyl}methyl)-4-(1-pyrrolidinyl)piperidine HPLC retention time (minute): 3.57;
MS: 503 (M+H)$^+$, 349, 177.

EXAMPLE 66-75

1-(2-fluorophenyl)-4-({6-[(4-isobutyl-2-methoxybenzyl)oxy]-1-methyl-3,4-dihydro-2-naphthalenyl}methyl)piperazine HPLC retention time (minute): 4.10;
MS: 529 (M+H)$^+$, 349, 177.

EXAMPLE 66-76

1-({6-[(4-isobutyl-2-methoxybenzyl)oxy]-1-methyl-3,4-dihydro-2-naphthalenyl}methyl)-4-(3-methoxyphenyl)piperazine HPLC retention time (minute): 4.06;
MS: 541 (M+H)$^+$, 349, 177.

EXAMPLE 66-77

2-{2-[4-({6-[(4-isobutyl-2-methoxybenzyl)oxy]-1-methyl-3,4-dihydro-2-naphthalenyl}methyl)-1-piperazinyl]ethoxy}ethanol HPLC retention time (minute): 3.53;
MS: 523 (M+H)$^+$, 349, 177.

EXAMPLE 66-78 t-butyl 4-({6-[(4-isobutyl-2-methoxybenzyl)oxy]-1-methyl-3,4-dihydro-2-naphthalenyl}methyl)-1-piperazinecarboxylate HPLC retention time (minute): 4.03;
MS: 535 (M+H)$^+$, 349, 177.

EXAMPLE 66-79

(3R)-1-({6-[(4-isobutyl-2-methoxybenzyl)oxy]-1-methyl-3,4-dihydro-2-naphthalenyl}methyl)-3-pyrrolidinol HPLC retention time (minute): 3.80;
MS: 871 (2M+H)$^+$, 436 (M+H)$^+$, 349, 177.

EXAMPLE 66-80

1-allyl-4-({6-[(4-isobutyl-2-methoxybenzyl)oxy]-1-methyl-3,4-dihydro-2-naphthalenyl}methyl)piperazine HPLC retention time (minute): 3.62;
MS: 949 (2M+H)$^+$, 475 (M+H)$^+$, 349, 177.

EXAMPLE 66-82

1-(cyclohexylmethyl)-4-({6-[(4-isobutyl-2-methoxybenzyl)oxy]-1-methyl-3,4-dihydro-2-naphthalenyl}methyl)piperazine HPLC retention time (minute): 3.76;
MS: 531 (M+H)$^+$, 349, 177.

EXAMPLE 66-83

1-(2-ethoxyethyl)-4-({6-[(4-isobutyl-2-methoxybenzyl)oxy]-1-methyl-3,4-dihydro-2-naphthalenyl}methyl)piperazine HPLC retention time (minute): 3.66;
MS: 507 (M+H)$^+$, 349, 177.

EXAMPLE 66-84 t-butyl (1S,4S)-5-({6-[(4-isobutyl-2-methoxybenzyl)oxy]-1-methyl-3,4-dihydro-2-naphthalenyl}methyl)-2,5-diazabicyclo[2.2.1]heptane-2-carboxylate:

HPLC retention time (minute): 4.02;
MS: 547 (M+H)$^+$, 349, 177.

EXAMPLE 66-85

N-{[(2R)-1-({6-[(4-isobutyl-2-methoxybenzyl)oxy]-1-methyl-3,4-dihydro-2-naphthalenyl}methyl)-2-pyrrolidinyl]methyl}aniline HPLC retention time (minute): 4.12;
MS: 525 (M+H)$^+$, 349, 177.

EXAMPLE 66-87

1-(3,4-dimethylphenyl)-4-({6-[(4-isobutyl-2-methoxybenzyl)oxy]-1-methyl-3,4-dihydro-2-naphthalenyl}methyl)piperazine HPLC retention time (minute): 4.17;
MS: 539 (M+H)$^+$, 349, 177.

EXAMPLE 66-88

1-(2,5-dimethylphenyl)-4-({6-[(4-isobutyl-2-methoxybenzyl)oxy]-1-methyl-3,4-dihydro-2-naphthalenyl}methyl)piperazine HPLC retention time (minute): 4.21;
MS: 539 (M+H)$^+$, 349, 177.

EXAMPLE 66-89

1-(2-furoyl)-4-({6-[(4-isobutyl-2-methoxybenzyl)oxy]-1-methyl-3,4-dihydro-2-naphthalenyl}methyl)piperazine HPLC retention time (minute): 3.88;
MS: 529 (M+H)$^+$, 349, 177.

EXAMPLE 66-90

1-({6-[(4-isobutyl-2-methoxybenzyl)oxy]-1-methyl-3,4-dihydro-2-naphthalenyl}methyl)-4-(2-phenylethyl)piperazine HPLC retention time (minute): 3.77;
MS: 539 (M+H)$^+$, 349, 177.

EXAMPLE 66-91

1-({6-[(4-isobutyl-2-methoxybenzyl)oxy]-1-methyl-3,4-dihydro-2-naphthalenyl}methyl)-4-(4-pyridinyl)piperazine HPLC retention time (minute): 3.57;
MS: 512 (M+H)$^+$, 349, 177.

EXAMPLE 66-92

2-[4-({6-[(4-isobutyl-2-methoxybenzyl)oxy]-1-methyl-3,4-dihydro-2-naphthalenyl}methyl)-1-piperazinyl]benzonitrile HPLC retention time (minute): 4.06;
MS: 536 (M+H)$^+$, 349, 177.

EXAMPLE 66-93

3-[4-({6-[(4-isobutyl-2-methoxybenzyl)oxy]-1-methyl-3,4-dihydro-2-naphthalenyl}methyl)-1-piperazinyl]phenol HPLC retention time (minute): 3.95;
MS: 527 (M+H)$^+$, 349, 177.

EXAMPLE 66-94

1-(2,4-difluorophenyl)-4-({6-[(4-isobutyl-2-methoxybenzyl)oxy]-1-methyl-3,4-dihydro-2-naphthalenyl}methyl)piperazine HPLC retention time (minute): 4.11;
MS: 547 (M+H)$^+$, 349, 177.

EXAMPLE 66-95

1-({6-[(4-isobutyl-2-methoxybenzyl)oxy]-1-methyl-3,4-dihydro-2-naphthalenyl}methyl)-4-(trifluoromethyl)piperidine HPLC retention time (minute): 4.01;
MS: 502 (M+H)+, 349, 177.

EXAMPLE 66-96

2-[4-({6-[(4-isobutyl-2-methoxybenzyl)oxy]-1-methyl-3,4-dihydro-2-naphthalenyl}methyl)-1-piperazinyl]phenol HPLC retention time (minute): 3.98;
MS: 527 (M+H)+, 349, 177.

EXAMPLE 66-97

1-({6-[(4-isobutyl-2-methoxybenzyl)oxy]-1-methyl-3,4-dihydro-2-naphthalenyl}methyl)-4-(tetrahydro-2-furanylcarbonyl)piperazine HPLC retention time (minute): 3.83;
MS: 533 (M+H)+, 349, 177

EXAMPLE 66-99

1-benzyl-4-({6-[(4-isobutyl-2-methoxybenzyl)oxy]-1-methyl-3,4-dihydro-2-naphthalenyl}methyl)-1,4-diazepane HPLC retention time (minute): 3.68;
MS: 539 (M+H)+, 349, 177.

EXAMPLE 66-101

4-({6-[(4-isobutyl-2-methoxybenzyl)oxy]-1-methyl-3,4-dihydro-2-naphthalenyl}methyl)-1,4-diazepane-1-carbaldehyde HPLC retention time (minute): 3.76;
MS: 953 (2M+H)+, 349, 177.

EXAMPLE 66-102

2-[4-({6-[(4-isobutyl-2-methoxybenzyl)oxy]-1-methyl-3,4-dihydro-2-naphthalenyl}methyl)-1-piperazinyl]-N-isopropylacetamide HPLC retention time (minute): 3.76;
MS: 534 (M+H)+, 349, 177.

EXAMPLE 66-103

1-({6-[(4-isobutyl-2-methoxybenzyl)oxy]-1-methyl-3,4-dihydro-2-naphthalenyl}methyl)-4-phenylpiperidine HPLC retention time (minute): 4.12;
MS: 510 (M+H)+, 349, 177.

EXAMPLE 66-104

1-(2,3-dimethylphenyl)-4-({6-[(4-isobutyl-2-methoxybenzyl)oxy]-1-methyl-3,4-dihydro-2-naphthalenyl}methyl)piperazine HPLC retention time (minute): 4.21;
MS: 539 (M+H)+, 349, 177.

EXAMPLE 66-105

1-({6-[(4-isobutyl-2-methoxybenzyl)oxy]-1-methyl-3,4-dihydro-2-naphthalenyl}methyl)-4-(4-methoxyphenyl)piperazine HPLC retention time (minute): 4.05;
MS: 541 (M+H)+, 349, 177.

EXAMPLE 66-106

2-[4-({6-[(4-isobutyl-2-methoxybenzyl)oxy]-1-methyl-3,4-dihydro-2-naphthalenyl}methyl)-1-piperazinyl]pyrazine HPLC retention time (minute): 3.86;
MS: 513 (M+H)+, 349, 177.

EXAMPLE 66-107

1-cyclohexyl-4-({6-[(4-isobutyl-2-methoxybenzyl)oxy]-1-methyl-3,4-dihydro-2-naphthalenyl}methyl)piperazine HPLC retention time (minute): 3.71;
MS: 517 (M+H)+, 349, 177.

EXAMPLE 66-108

1-(4-chlorophenyl)-4-({6-[(4-isobutyl-2-methoxybenzyl)oxy]-1-methyl-3,4-dihydro-2-naphthalenyl}methyl)piperazine HPLC retention time (minute): 4.14;
MS: 545 (M+H)+, 349, 177.

EXAMPLE 66-109

1-({6-[(4-isobutyl-2-methoxybenzyl)oxy]-1-methyl-3,4-dihydro-2-naphthalenyl}methyl)-4-(2-methoxyethyl)piperazine HPLC retention time (minute): 3.60;
MS: 985 (2M+H)+, 493 (M+H)+, 349, 177.

EXAMPLE 66-110

4-{2-[4-({6-[(4-isobutyl-2-methoxybenzyl)oxy]-1-methyl-3,4-dihydro-2-naphthalenyl}methyl)-1-piperazinyl]ethyl}morpholine HPLC retention time (minute): 3.55;
MS: 548 (M+H)+, 349, 177.

EXAMPLE 66-111

(2S,5S)-1-({6-[(4-isobutyl-2-methoxybenzyl)oxy]-1-methyl-3,4-dihydro-2-naphthalenyl}methyl)-2,5-bis(methoxymethyl)pyrrolidine HPLC retention time (minute): 4.04;
MS: 508 (M+H)$^+$, 349, 177.

EXAMPLE 66-112

4-({6-[(4-isobutyl-2-methoxybenzyl)oxy]-1-methyl-3,4-dihydro-2-naphthalenyl}methyl)-2-piperazinone HPLC retention time (minute): 3.73;
MS: 897 (2M+H)$^+$, 349, 177.

EXAMPLE 66-113

(2S)-1-({6-[(4-isobutyl-2-methoxybenzyl)oxy]-1-methyl-3,4-dihydro-2-naphthalenyl}methyl)-N,N-dimethyl-2-pyrrolidinecarboxamide HPLC retention time (minute): 3.89;
MS: 491 (M+H)$^+$, 349, 177.

EXAMPLE 66-114

(2R)-1-({6-[(4-isobutyl-2-methoxybenzyl)oxy]-1-methyl-3,4-dihydro-2-naphthalenyl}methyl)-2-pyrrolidinecarboxamide HPLC retention time (minute): 3.79;
MS: 925 (2M+H)$^+$, 463 (M+H)$^+$, 349, 177.

EXAMPLE 66-115

1-({6-[(4-isobutyl-2-methoxybenzyl)oxy]-1-methyl-3,4-dihydro-2-naphthalenyl}methyl)-4-(2-methylphenyl)piperazine HPLC retention time (minute): 4.16;
MS: 525 (M+H)$^+$, 349, 177.

EXAMPLE 66-116

2-[4-({6-[(4-isobutyl-2-methoxybenzyl)oxy]-1-methyl-3,4-dihydro-2-naphthalenyl}methyl)-1-piperazinyl]nicotinonitrile HPLC retention time (minute): 4.00;
MS: 537 (M+H)$^+$, 349, 177.

EXAMPLE 66-117

3-[4-({6-[(4-isobutyl-2-methoxybenzyl)oxy]-1-methyl-3,4-dihydro-2-naphthalenyl}methyl)-1-piperazinyl]-2-pyrazinecarbonitrile HPLC retention time (minute): 3.99;
MS: 538 (M+H)$^+$, 349, 177.

EXAMPLE 66-118

6-[4-({6-[(4-isobutyl-2-methoxybenzyl)oxy]-1-methyl-3,4-dihydro-2-naphthalenyl}methyl)-1-piperazinyl]nicotinonitrile HPLC retention time (minute): 3.98;
MS: 537 (M+H)$^+$, 349, 177.

EXAMPLE 67-1 TO EXAMPLE 67-13

The procedure of Example 27 was followed but using a corresponding amine compound as a substitute for piperidine. Thus, the compound of the present invention having the following physical properties was obtained.

EXAMPLE 67-1

1-[(6-{[(2R)-3-(4-fluorophenyl)-2-methylpropyl]oxy}-1-methyl-3,4-dihydro-2-naphthalenyl)methyl]azocane HPLC retention time (minute): 3.84;
MS: 985 (2M+H)$^+$, 436 (M+H)$^+$, 323.

EXAMPLE 67-2

1-[(6-{[(2R)-3-(4-fluorophenyl)-2-methylpropyl]oxy}-1-methyl-3,4-dihydro-2-naphthalenyl)methyl]pyrrolidine HPLC retention time (minute): 3.71;
MS: 393 (M+H)$^+$, 323.

EXAMPLE 67-3

1-[(6-{[(2R)-3-(4-fluorophenyl)-2-methylpropyl]oxy}-1-methyl-3,4-dihydro-2-naphthalenyl)methyl]-3-pyrrolidinol HPLC retention time (minute): 3.60;
MS: 410 (M+H)$^+$, 323.

EXAMPLE 67-4

1-[(6-{[(2R)-3-(4-fluorophenyl)-2-methylpropyl]oxy}-1-methyl-3,4-dihydro-2-naphthalenyl)methyl]-4-phenylpiperazine HPLC retention time (minute): 3.87;
MS: 485 (M+H)$^+$, 323.

EXAMPLE 67-5

4-[(6-{[(2R)-3-(4-fluorophenyl)-2-methylpropyl]oxy}-1-methyl-3,4-dihydro-2-naphthalenyl)methyl]-1-piperazinecarbaldehyde HPLC retention time (minute): 3.58;
MS: 873 (2M+H)$^+$, 323.

EXAMPLE 67-6

1-[(6-{[(2R)-3-(4-fluorophenyl)-2-methylpropyl]oxy}-1-methyl-3,4-dihydro-2-naphthalenyl)methyl]-4-methylpiperazine HPLC retention time (minute): 3.42;
MS: 423 (M+H)+, 323.

EXAMPLE 67-7

1-benzyl-4-[(6-{[(2R)-3-(4-fluorophenyl)-2-methylpropyl]oxy}-1-methyl-3,4-dihydro-2-naphthalenyl)methyl]piperazine HPLC retention time (minute): 3.58;
MS: 499 (M+H)+, 323.

EXAMPLE 67-8

4-[(6-{[(2R)-3-(4-fluorophenyl)-2-methylpropyl]oxy}-1-methyl-3,4-dihydro-2-naphthalenyl)methyl]morpholine HPLC retention time (minute): 3.66;
MS: 410 (M+H)+, 323.

EXAMPLE 67-9

1-[(6-{[(2R)-3-(4-fluorophenyl)-2-methylpropyl]oxy}-1-methyl-3,4-dihydro-2-naphthalenyl)methyl]piperidine HPLC retention time (minute): 3.75;
MS: 408 (M+H)+, 323.

EXAMPLE 67-10

1-[(6-{[(2R)-3-(4-fluorophenyl)-2-methylpropyl]oxy}-1-methyl-3,4-dihydro-2-naphthalenyl)methyl]-4-(2-piperidinyl)piperazine HPLC retention time (minute): 3.45;
MS: 486 (M+H)+, 323.

EXAMPLE 67-11

4-[(6-{[(2R)-3-(4-fluorophenyl)-2-methylpropyl]oxy}-1-methyl-3,4-dihydro-2-naphthalenyl)methyl]-2-piperazinone HPLC retention time (minute): 3.53;
MS: 845 (2M+H)+, 323.

EXAMPLE 67-12

N-[(6-{[(2R)-3-(4-fluorophenyl)-2-methylpropyl]oxy}-1-methyl-3,4-dihydro-2-naphthalenyl)methyl]-N-methyl-1-pentanamine HPLC retention time (minute): 3.89;
MS: 424 (M+H)+, 323.

EXAMPLE 67-13

N-[(6-{[(2R)-3-(4-fluorophenyl)-2-methylpropyl]oxy}-1-methyl-3,4-dihydro-2-naphthalenyl)methyl]-N,N',N'-trimethyl-1,3-propanediamine HPLC retention time (minute): 3.40;
MS: 439 (M+H)+, 323.

BIOLOGICAL EXAMPLES

The pharmacological action of the compounds of the present invention have been confirmed by the following Biological Examples. All operations were carried out by conventional methods by preparing gene-highly expressing cells based on the fundamental genetic engineering techniques. Also, the measuring methods in the present invention for evaluating the compounds of the present invention were carried out, for example, by improving measuring methods, measuring accuracy and/or measuring sensitivity. The details are described below. The preparation of histological preparation was also carried out by conventional methods based on the fundamental genetic engineering techniques with an appropriate modification.

Biological Example 1

Measurement of inhibitory activity of the compound of the present invention on binding of [$^3$H]-PhS1P to EDG-6:
Method:

By using cell membrane fraction of an EDG-6-overexpressing Chinese Hamster Ovary (CHO) cell and 1 mg protein/mL of the membrane fraction, reaction was carried out in a 96-well plate. Into each well, 80 µL of a vehicle (DMSO) solution diluted with 2× binding buffer (100 mmol/L Tris pH 7.5, 200 mM NaCl, 30 mM NaF, 1% BSA) or a ligand solution having a twice higher concentration and 40 µL of 10 nmol/L [$^3$H]-PhS1P (5,5,6,6,-tetralithium phytosphingosine 1-phosphate: This was prepared in the following manner. A compound (anti-7-tert-butyl (4S)-4-[(1S,2R)-1-(benzyloxy)-2-hydroxyhexadec-3-yn-1-yl]-2,2-dimethyl-1,3-oxazolizine-3-carboxylate) prepared in accordance with a method reported in a document (*Tetrahedron Lett.*, 38(34), 6027-6030 (1997)) was reacted with benzyl bromide in tetrahydrofuran in the presence of potassium hexamethyldisilylamide to thereby protect the hydroxy group of the compound. Then, it was treated in hydrogen chloride/methanol solution to remove an acetonide group. The compound thus obtained was reacted with N,N-diethyl-1,5-dihydro-2,4,3-benzodioxaphosphepin-3-amine in dichloromethane in the presence of tetrazole and then oxidized with m-chloroperbenzoic acid. Then, it was reacted in the presence of ASCA-2 catalyst (manufactured by NE Chemcat, 4.5% palladium-0.5% platinum catalyst carried on active carbon, see, Fine Chemical, Oct. 1, 2002, pages 5 to 14) in methanol under a tritium atmosphere. The obtained compound was treated with a 4 N hydrogen chloride/1,4-dioxane solution in dichloromethane to thereby obtain the desired compound) were added. Further, 40 µl of the membrane fraction solution was added and reacted at room temperature for 60 minutes. After the completion of the reaction, the reaction mixture was filtered by aspiration with a 96-well Unifilter, washed with 50 mL of a washing buffer (50 mmol/L Tris pH7.5, 0.5% BSA) thrice and dried at 60° C. for 45 minutes. Then, 50 µl/well of Micro Scint 20 was added and the plate was covered with Top Seal-P. Then the radioactivity was measured with Top Count (Perkin Elmer).

Results:

The compounds of the present invention showed inhibitory activities on the binding of [$^3$H]-PhS1P to EDG-6. For example, IC$_{50}$ values of the compounds prepared in Example 27, Example 37-1, and Example 66-24 were 26, 98, and 81 nmol/L, respectively.

Biological Example 2

Counting the Number of Lymphocyte in Blood

Method:

Test compounds were orally administered to male BALB/c mice or male Sprague-Dawley rats (Charles Riber Laboratories, Japan, Ltd., 6-week-old at the time of use). Four to 72 hours after the administration, the blood was collected from the aorta abdominalis under ether anesthesia. The number of the total leucocyte count, the lymphocyte count, the neutrophil count, the erythrocyte count, the platelet count in blood and the hematocrit value were measured with a multipurpose automatic blood cell counter (SF-3000, Sysmex). Evaluation was made by setting the average blood cell count in a vehicle-administered group (vehicle group) as 100% and calculating the percentage of vehicle from the average blood cell count of each test compound-administered group. Based on the test compound doses and percentages of vehicle with the doses, the dose of the compound required for lowering the blood cell count to 50% was calculated as ED$_{50}$.

Results:

The compounds of the present invention significantly lowered the number of lymphocyte in blood in a dose of 10 mg/kg.

Biological Example 3

Evaluation of an agonistic activity against EDG of the compound of the present invention by monitoring changes in intracellular calcium ion [Ca$^{2+}$]$_i$ concentration:

Method:

Human EDG-1, EDG-3, EDG-5 or EDG-8 gene overexpressing CHO cells were cultured in Ham's F12 medium (manufactured by GIBCO BRL) containing 10% FBS (fetal bovine serum), penicillin/streptomycin and blasticidin (5 µg/ml). The cultured cells were incubated in a 5 µM Fura2-AM solution (Ham's F12 medium containing 10% of FBS, 20 mM HEPES buffer (pH7.4), and 2.5 mM probenecid) at 37° C. for 60 minutes. After washing once with Hanks solution containing 20 mM HEPES buffer (pH7.4), and 2.5 mM probenecid, the plate was soaked in the same solution until assay. Then, the plate was set on a fluorescent drug screening system (FDSS 6000; Hamamatsu Photonics) and the intracellular calcium ion concentration was measured without stimulation for 30 seconds. A test compound (final concentration: 1 nM to 10 µM, dimethylsulfoxide (DMSO) solution) was added and S1P (final concentration: 100 nM) was added 5 minutes thereafter. Then, the increase in the intracellular calcium ion concentration was measured before and after the addition of S1P at intervals of 3 seconds (excitation wavelength: 340 nm and 380 nm, fluorescence wavelength: 500 nm).

The agonistic activity of the compound against each EDG was determined by using the peak value due to S1P-stimulation in a well containing DMSO as a substitute for the evaluated compound as a control value (A), comparing the value before the addition of the evaluated compound with the increased value (B) in the fluorescent ratio after the addition, and calculating the increase ratio (%) in the intracellular calcium ion [Ca$^{2+}$]$_i$ concentration as: increase ratio (%)=(B/A)×100. Increase ratios of the compound at individual concentrations were determined and the EC$_{50}$ was calculated.

Results:

It was indicated that the compounds of the present invention showed an agonistic activity against EDG-1. For example, EC$_{50}$ values of the compounds prepared in Example 5 and Example 6 were 7.8 and 0.25 µmol/L, respectively.

Biological Example 4

Mouse Model of Dermatitis Caused by Continuous Application of Hapten

Method:

A 1% (w/v) 4-ethoxymethylene-2-phenyl-2-oxazolin-5-one (hereinafter, abbreviated as "oxalon") solution was applied (20 µL) to an ear auricle (right, both faces) of mice (male Balb/c) to perform the primary sensitization. Seven days after the sensitization, a 1% (w/v) oxalon solution was applied (20 µL) for elicitation (Day 0). The same procedure as the Day 0 was repeated on the days 2, 4, 6, 8, 10, 12, 14 and 16. A test compound was dissolved in a vehicle and then orally administered or applied to both faces of the right ear (20 µL) before the application of oxalon. To the control group, only the vehicle was applied. Immediately before the administration of the test compound and 24 hours after the oxalon application, the thickness of the mouse ear auricle was measured with Dial Thickness Gauge (Ozaki Seisakusho) as an indication of the efficacy to the mouse model of dermatitis induced by the continuous application of hapten.

Biological Example 5

Adjuvant-induced Arthritis Model

Method:

Evaluation was made by using 7 weeks male or female Lewis rats. After measuring the volume of the left hinder leg of a rat, a 500 µg/rat suspension of dry Mycobacterium butyricum cells (Difco), which was employed as an adjuvant, in liquid paraffin is subcutaneously injected into the right hinder foot pad. Thus, a rat adjuvant-induced arthritis model was constructed. By comparing a test group to which a test compound had been orally administered with a control group of to which administration is not performed, the therapeutic or preventive effect was evaluated.

Biological Example 6

EDG-6 Signaling Detecting Method Based on Measurement of Phosphorylated ERK

Method:

EDG-6 (S1P$_4$) receptor expressing CHO cells, which had been subcultured in Ham's F12 medium (manufactured by GIBCO BRL) containing 10% FCS and Geneticin (250 µg/mL) were seeded in a 6-well cell culture plate (available from Coaster) at 5×10$^5$ cell/well, and incubated overnight under conditions of 37° C. and 5% CO$_2$. After the incubation, the medium was removed from the culture plate, Ham's F12 medium containing 0.1% BSA (Fatty acid Free) was added to the culture plate, and incubated overnight under conditions of 37° C. and 5% CO$_2$. The medium was removed after the incubation, and then Ham's F12 medium containing 0.1% BSA (Fatty acid Free) in which various concentrations of test materials were dissolved was added to the culture plate, and the plate was reacted for 10 minutes at room temperature. After that, the medium was removed and cells were washed with an ice-cold PBS. 100 µL of Lysis buffer (20 mmol/L Tris-HCl pH 7.5, 1% Triton X-100, 1 mmol/L EDTA, 1 mmol/L EGTA, 0.5 mmol/L $Na_3VO_4$, 50 mmol/L NaF, 1× Complete Protease inhibitor Cocktail) was added to each well, and the plate was reacted on ice for 5 minutes to dissolve the cells. SDS-PAGE sample buffer was added to a supernatant of the cell lysate and treated at 100° C. The resultant was used as a sample for electrophoresis and separated by means of SDS-PAGE. The separated sample was transferred to a PVDF membrane (Immuno Blot PVDF membrane, trade name, manufactured by BIO-RAD). Phosphorylated ERK on the membrane was allowed to react with anti-phosphorylated ERK (p42/44 MAPK) polyclonal antibody (Phospho-p44/42 MAP Kinase (Thr202/Tyr204) Antibody, trade name, manufactured by Cell Signaling Technology), and further react with an HRP-labeled anti-rabbit IgG antibody (manufactured by Cell Signaling Technology). After that, a band developed from the resultant by using ECL plus Reagent (manufactured by Amersham) was detected by means of Science Imaging System (LAS-100, trade name, manufactured by FUJI FILM). Comparison between a group which was added with a test material and a group which was not added with a test material enables detection of EDG-6 signaling.

FORMULATION EXAMPLES

Formulation examples carried out in the present invention are shown below.

Formulation Example 1

N-[(1-{[6-(3-phenylpropoxy)-2-naphthyl]methyl}azetidin-3-yl)carbonyl]benzensulfonamide (100 g), calcium carboxymethylcellulose (disintegrant, 20.0 g), magnesium stearate (lubricant, 10.0 g) and microcrystalline cellulose (870 g) were mixed in a conventional manner, punched them out to obtain 10,000 tablets each containing 10 mg of the active ingredient.

Formulation Example 2

N-[(1-{[6-(3-phenylpropoxy)-2-naphthyl]methyl}azetidin-3-yl)carbonyl]benzensulfonamide (200 g), mannitol (2 kg) and distilled water (50 L) were mixed in a conventional manner. Then the solution was filtered through a dustproofing filter, and then 5 ml aliquots were charged into ampoules, which were autoclaved to obtain 10,000 ampoules each containing 20 mg of the active ingredient.

INDUSTRIAL APPLICABILITY

The compound of the present invention can be applied to the following medicaments.

The compound of the present invention is a compound capable of binding S1P receptor (in particular, EDG-1 and/or EDG-6). Accordingly, the compound is useful as a preventing and/or treating agent for mammals (for example, human, or non-human animals such as simian, ovine, bovine, equine, canine, feline, leporine, rat, and mouse), for: rejection in transplantation; rejection of a transplanted organ; graft versus host disease; an autoimmune disease (e.g., systemic lupus erythematosus, rheumatoid arthritis, multiple sclerosis, psoriasis, ulcerative colitis, Crohn's disease, myasthenia gravis, and autoimmune diabetes); an allergic disease (e.g., atopic dermatitis, pollen disease, and food allergy); asthma; infectious disease; ulcer; lymphoma; malignant tumor (e.g., cancer); leukemia; and a disease associated with lymphocyte infiltration into a tissue; a peripheral arterial disease including arteriosclerosis, obliterans thromboangiitis obliterans, Buerger's disease, and diabetic neuropathy; varicose vein such as hemorrhoid, anal fissure, or anal fistula; dissecting aneurysm of the aorta; sepsis; an inflammatory disease such as angiitis, nephritis, or pneumonia; various edematous disease involved in ischemia of various organs and increase of the blood permeability, for example, cerebral stroke, ischemia-reperfusion injury, cerebral infarction, myocardial infarction, angina, congestive heart failure, pleuritis, DIC, or multiple organ failure; bedsore; burn; trauma injury; inflammatory bowel disease; genetic disease; osteoporosis; arteriosclerosis; fibrosis such as pulmonary fibrosis or liver fibrosis; interstitial pneumotitis; chronic hepatitis; liver cirrhosis; chronic renal insufficiency; renal glomerular sclerosis; diabetes; and the like. In addition, the compound of the present invention is useful as a preoperative, postoperative, and/or prognostic activator for blood vessel accompanying transplantation of various organs, tissues, and/or cells, for example, as an adhesion activator of transplanted organs such as heart transplantation, renal transplantation, dermal transplantation, or liver transplantation. In addition, the compound of the present invention is useful, not only in vivo but also in vitro, as an adjusting agent such as a differentiation activator of cells or the like.

The invention claimed is:
1. A compound which is
N-({6-[3-(4-fluorophenyl)propoxy]-1-methyl-3,4-dihydro-2-naphthalenyl}methyl)ethanamine,
N-(3-{[(6-{[(2S)-3-(4-chlorophenyl)-2-methylpropyl]oxy}-1-methyl-3,4-dihydro-2-naphthalenyl)methyl]amino}propanoyl)methanesulfonamide,
N-(3-{[(6-{[(2S)-3-(4-chlorophenyl)-2-methylpropyl]oxy}-1-methyl-3,4-dihydro-2-naphthalenyl)methyl]amino}propanoyl)-3,5-dimethyl-4-isoxazolesulfonamide,
N-[(6-{[(2S)-3-(4-fluorophenyl)-2-methylpropyl]oxy}-1-methyl-3,4-dihydro-2-naphthalenyl)methyl]ethanamine,
N-({6-[3-(4-fluorophenyl)-2-methylpropoxy]-1-methyl-3,4-dihydro-2-naphthalenyl}methyl)ethanamine,
N-({1-[(1-chloro-6-{[(2S)-3-(4-chlorophenyl)-2-methylpropyl]oxy}-3,4-dihydro-2-naphthalenyl)methyl]-3-azetidinyl}carbonyl)methanesulfonamide,
N-({1-[(1-chloro-6-{[(2S)-3-(4-chlorophenyl)-2-methylpropyl]oxy}-3,4-dihydro-2-naphthalenyl)methyl]-3-azetidinyl}carbonyl)-2,6-difluorobenzenesulfonamide,
N-({1-[(1-chloro-6-{[(2S)-3-(4-chlorophenyl)-2-methylpropyl]oxy}-3,4-dihydro-2-naphthalenyl)methyl]-3-azetidinyl}carbonyl)-3,5-dimethyl-4-isoxazolesulfonamide,
1-{6-[(4-isobutyl-2-methoxybenzyl)oxy]-1-methyl-3,4-dihydro-2-naphthalenyl}-N,N-dimethylmethanamine,
[1-({6-[(4-isobutyl-2-methoxybenzyl)oxy]-1-methyl-3,4-dihydro-2-naphthalenyl}methyl)-3-azetidinyl]methanol,
1-({6-[(4-isobutyl-2-methoxybenzyl)oxy]-1-methyl-3,4-dihydro-2-naphthalenyl}methyl)-4-(2-pyridinyl)piperazine,
2-[4-({6-[(4-isobutyl-2-methoxybenzyl)oxy]-1-methyl-3,4-dihydro-2-naphthalenyl}methyl)-1-piperazinyl]pyrimidine, 2-[4-({6-[(4-isobutyl-2-methoxybenzyl)oxy]-1-methyl-3,4-dihydro-2-naphthalenyl}methyl)-1-piperazinyl]pyrazine,
N-(3-{[(6-{[(2S)-3-(4-chlorophenyl)-2-methylpropyl]oxy}-1-methyl-3,4-dihydro-2-naphthalenyl)methyl]amino}propanoyl)benzenesulfonamide,

1-(6-{[(2S)-3-(4-fluorophenyl)-2-methylpropyl]oxy}-1-methyl-3,4-dihydro-2-naphthalenyl)-N,N-dimethylmethanamine,
1-[(6-{[(2S)-3-(4-fluorophenyl)-2-methylpropyl]oxy}-1-methyl-3,4-dihydro-2-naphthalenyl)methyl]azetidine,
1-[(6-{[(2S)-3-(4-fluorophenyl)-2-methylpropyl]oxy}-1-methyl-3,4-dihydro-2-naphthalenyl)methyl]pyrrolidine,
(3R)-1-[(6-{[(2S)-3-(4-fluorophenyl)-2-methylpropyl]oxy}-1-methyl-3,4-dihydro-2-naphthalenyl)methyl]-3-pyrrolidinol,
(3S)-1-[(6-{[(2S)-3-(4-fluorophenyl)-2-methylpropyl]oxy}-1-methyl-3,4-dihydro-2-naphthalenyl)methyl]-3-pyrrolidinol,
t-butyl {1-[(6-{[(2S)-3-(4-fluorophenyl)-2-methylpropyl]oxy}-1-methyl-3,4-dihydro-2-naphthalenyl)methyl]-3-pyrrolidinyl}carbamate,
{(2S)-1-[(6-{[(2S)-3-(4-fluorophenyl)-2-methylpropyl]oxy}-1-methyl-3,4-dihydro-2-naphthalenyl)methyl]-2-pyrrolidinyl}methanol,
{(2R)-1-[(6-{[(2S)-3-(4-fluorophenyl)-2-methylpropyl]oxy}-1-methyl-3,4-dihydro-2-naphthalenyl)methyl]-2-pyrrolidinyl}methanol,
(2S)-1-[(6-{[(2S)-3-(4-fluorophenyl)-2-methylpropyl]oxy}-1-methyl-3,4-dihydro-2-naphthalenyl)methyl]-2-(1-pyrrolidinylmethyl)pyrrolidine,
1-[(6-{[(2S)-3-(4-fluorophenyl)-2-methylpropyl]oxy}-1-methyl-3,4-dihydro-2-naphthalenyl)methyl]-4-methyl-1,4-diazepane,
1-({6-[(4-isobutyl-2-methoxybenzyl)oxy]-1-methyl-3,4-dihydro-2-naphthalenyl}methyl)pyrrolidine,
1-({6-[(4-isobutyl-2-methoxybenzyl)oxy]-1-methyl-3,4-dihydro-2-naphthalenyl}methyl)-2,5-dihydro-1H-pyrrole,
3-({6-[(4-isobutyl-2-methoxybenzyl)oxy]-1-methyl-3,4-dihydro-2-naphthalenyl}methyl)-1,3-thiazolidine,
1-({6-[(4-isobutyl-2-methoxybenzyl)oxy]-1-methyl-3,4-dihydro-2-naphthalenyl}methyl)azocane,
[(2S)-1-({6-[(4-isobutyl-2-methoxybenzyl)oxy]-1-methyl-3,4-dihydro-2-naphthalenyl}methyl)-2-pyrrolidinyl]methanol,
1-({6-[(4-isobutyl-2-methoxybenzyl)oxy]-1-methyl-3,4-dihydro-2-naphthalenyl}methyl)-3-pyrrolidinol,
1-({6-[(4-isobutyl-2-methoxybenzyl)oxy]-1-methyl-3,4-dihydro-2-naphthalenyl}methyl)-4-phenylpiperazine,
1-({6-[(4-isobutyl-2-methoxybenzyl)oxy]-1-methyl-3,4-dihydro-2-naphthalenyl}methyl)-4-(2-methoxyphenyl)piperazine,
4-({6-[(4-isobutyl-2-methoxybenzyl)oxy]-1-methyl-3,4-dihydro-2-naphthalenyl}methyl)-1-piperazinecarbaldehyde,
ethyl 4-({6-[(4-isobutyl-2-methoxybenzyl)oxy]-1-methyl-3,4-dihydro-2-naphthalenyl}methyl)-1-piperazinecarboxylate,
1-({6-[(4-isobutyl-2-methoxybenzyl)oxy]-1-methyl-3,4-dihydro-2-naphthalenyl}methyl)-4-methylpiperazine,
4-({6-[(4-isobutyl-2-methoxybenzyl)oxy]-1-methyl-3,4-dihydro-2-naphthalenyl}methyl)morpholine,
4-({6-[(4-isobutyl-2-methoxybenzyl)oxy]-1-methyl-3,4-dihydro-2-naphthalenyl}methyl)thiomorpholine,
1-({6-[(4-isobutyl-2-methoxybenzyl)oxy]-1-methyl-3,4-dihydro-2-naphthalenyl}methyl)piperidine,
[1-({6-[(4-isobutyl-2-methoxybenzyl)oxy]-1-methyl-3,4-dihydro-2-naphthalenyl}methyl)-2-piperidinyl]methanol,
1-({6-[(4-isobutyl-2-methoxybenzyl)oxy]-1-methyl-3,4-dihydro-2-naphthalenyl}methyl)-3-piperidinecarboxamide,
1-({6-[(4-isobutyl-2-methoxybenzyl)oxy]-1-methyl-3,4-dihydro-2-naphthalenyl}methyl)-3-methylpiperidine,
1-({6-[(4-isobutyl-2-methoxybenzyl)oxy]-1-methyl-3,4-dihydro-2-naphthalenyl}methyl)-3,5-dimethylpiperidine,
1-({6-[(4-isobutyl-2-methoxybenzyl)oxy]-1-methyl-3,4-dihydro-2-naphthalenyl}methyl)-4-piperidinol,
1-({6-[(4-isobutyl-2-methoxybenzyl)oxy]-1-methyl-3,4-dihydro-2-naphthalenyl}methyl)-4-methylpiperidine,
4-benzyl-1-({6-[(4-isobutyl-2-methoxybenzyl)oxy]-1-methyl-3,4-dihydro-2-naphthalenyl}methyl)piperidine,
1-({6-[(4-isobutyl-2-methoxybenzyl)oxy]-1-methyl-3,4-dihydro-2-naphthalenyl}methyl)decahydroquinoline,
2-({6-[(4-isobutyl-2-methoxybenzyl)oxy]-1-methyl-3,4-dihydro-2-naphthalenyl}methyl)-1,2,3,4-tetrahydroisoquinoline,
1-({6-[(4-isobutyl-2-methoxybenzyl)oxy]-1-methyl-3,4-dihydro-2-naphthalenyl}methyl)azepane,
(2S)-1-({6-[(4-isobutyl-2-methoxybenzyl)oxy]-1-methyl-3,4-dihydro-2-naphthalenyl}methyl)-2-(methoxymethyl)pyrrolidine,
2-({6-[(4-isobutyl-2-methoxybenzyl)oxy]-1-methyl-3,4-dihydro-2-naphthalenyl}methyl)decahydroisoquinoline,
(2S)-1-({6-[(4-isobutyl-2-methoxybenzyl)oxy]-1-methyl-3,4-dihydro-2-naphthalenyl}methyl)-2-(1-pyrrolidinylmethyl)pyrrolidine,
N-{[(2S)-1-({6-[(4-isobutyl-2-methoxybenzyl)oxy]-1-methyl-3,4-dihydro-2-naphthalenyl}methyl)-2-pyrrolidinyl]methyl}aniline,
1-({6-[(4-isobutyl-2-methoxybenzyl)oxy]-1-methyl-3,4-dihydro-2-naphthalenyl}methyl)-4-piperidinecarboxamide,
1-(2-chlorophenyl)-4-({6-[(4-isobutyl-2-methoxybenzyl)oxy]-1-methyl-3,4-dihydro-2-naphthalenyl}methyl)piperazine,
1-({6-[(4-isobutyl-2-methoxybenzyl)oxy]-1-methyl-3,4-dihydro-2-naphthalenyl}methyl)azonane,
1-acetyl-4-({6-[(4-isobutyl-2-methoxybenzyl)oxy]-1-methyl-3,4-dihydro-2-naphthalenyl}methyl)piperazine,
N-[1-({6-[(4-isobutyl-2-methoxybenzyl)oxy]-1-methyl-3,4-dihydro-2-naphthalenyl}methyl)-3-pyrrolidinyl]acetamide,
N-[1-({6-[(4-isobutyl-2-methoxybenzyl)oxy]-1-methyl-3,4-dihydro-2-naphthalenyl}methyl)-3-pyrrolidinyl]-N-methylacetamide,
N-ethyl-N-[1-({6-[(4-isobutyl-2-methoxybenzyl)oxy]-1-methyl-3,4-dihydro-2-naphthalenyl}methyl)-3-pyrrolidinyl]acetamide,
t-butyl [1-({6-[(4-isobutyl-2-methoxybenzyl)oxy]-1-methyl-3,4-dihydro-2-naphthalenyl}methyl)-3-pyrrolidinyl]carbamate,
1-({6-[(4-isobutyl-2-methoxybenzyl)oxy]-1-methyl-3,4-dihydro-2-naphthalenyl}methyl)-4-methyl-1,4-diazepane, 1-ethyl-4-({6-[(4-isobutyl-2-methoxybenzyl)oxy]-1-methyl-3,4-dihydro-2-naphthalenyl}methyl)piperazine,
[(2R)-1-({6-[(4-isobutyl-2-methoxybenzyl)oxy]-1-methyl-3,4-dihydro-2-naphthalenyl}methyl)-2-pyrrolidinyl]methanol,
4-[4-({6-[(4-isobutyl-2-methoxybenzyl)oxy]-1-methyl-3,4-dihydro-2-naphthalenyl}methyl)-1-piperazinyl]phenol, (2R)-1-({6-[(4-isobutyl-2-methoxybenzyl)oxy]-1-methyl-3,4-dihydro-2-naphthalenyl}methyl)-2-(methoxymethyl)pyrrolidine,
rel-(4aR,8aS)-2-({6-[(4-isobutyl-2-methoxybenzyl)oxy]-1-methyl-3,4-dihydro-2-naphthalenyl}methyl)decahydroisoquinoline,
rel-(2R,6S)-4-({6-[(4-isobutyl-2-methoxybenzyl)oxy]-1-methyl-3,4-dihydro-2-naphthalenyl}methyl)-2,6-dimethylmorpholine,
N-[(3R)-1-({6-[(4-isobutyl-2-methoxybenzyl)oxy]-1-methyl-3,4-dihydro-2-naphthalenyl}methyl)-3-pyrrolidinyl]acetamide,
N-[(3S)-1-({6-[(4-isobutyl-2-methoxybenzyl)oxy]-1-methyl-3,4-dihydro-2-naphthalenyl}methyl)-3-pyrrolidinyl]acetamide,
t-butyl [(3R)-1-({6-[(4-isobutyl-2-methoxybenzyl)oxy]-1-methyl-3,4-dihydro-2-naphthalenyl}methyl)-3-pyrrolidinyl]carbamate,
t-butyl [(3S)-1-({6-[(4-isobutyl-2-methoxybenzyl)oxy]-1-methyl-3,4-dihydro-2-naphthalenyl}methyl)-3-pyrrolidinyl]carbamate,
(3R)-1-({6-[(4-isobutyl-2-methoxybenzyl)oxy]-1-methyl-3,4-dihydro-2-naphthalenyl}methyl)-N,N-dimethyl-3-pyrrolidinamine,
(3S)-1-({6-[(4-isobutyl-2-methoxybenzyl)oxy]-1-methyl-3,4-dihydro-2-naphthalenyl}methyl)-N,N-dimethyl-3-pyrrolidinamine,
1-({6-[(4-isobutyl-2-methoxybenzyl)oxy]-1-methyl-3,4-dihydro-2-naphthalenyl}methyl)-N,N-dimethyl-3-pyrrolidinamine,
[(3S)-2-({6-[(4-isobutyl-2-methoxybenzyl)oxy]-1-methyl-3,4-dihydro-2-naphthalenyl}methyl)-1,2,3,4-tetarahydro-3-isoquinolinyl]methanol,
3-[1-({6-[(4-isobutyl-2-methoxybenzyl)oxy]-1-methyl-3,4-dihydro-2-naphthalenyl}methyl)-4-piperidinyl]phenol,
N,N-diethyl-1-({6-[(4-isobutyl-2-methoxybenzyl)oxy]-1-methyl-3,4-dihydro-2-naphthalenyl}methyl)-3-pyrrolidinamine,
2-({6-[(4-isobutyl-2-methoxybenzyl)oxy]-1-methyl-3,4-dihydro-2-naphthalenyl}methyl)-2,3,4,9-tetrahydro-1H-β-carboline:
1-({6-[(4-isobutyl-2-methoxybenzyl)oxy]-1-methyl-3,4-dihydro-2-naphthalenyl}methyl)azetidine,
1-({6-[(4-isobutyl-2-methoxybenzyl)oxy]-1-methyl-3,4-dihydro-2-naphthalenyl}methyl)-2,5-dimethyl-2,5-dihydro-1H-pyrrole,
(2S)-1-({6-[(4-isobutyl-2-methoxybenzyl)oxy]-1-methyl-3,4-dihydro-2-naphthalenyl }methyl)-2-pyrrolidinecarboxamide,
1-({6-[(4-isobutyl-2-methoxybenzyl)oxy]-1-methyl-3,4-dihydro-2-naphthalenyl}methyl)-2,5-dimethylpyrrolidine,
1-({6-[(4-isobutyl-2-methoxybenzyl)oxy]-1-methyl-3,4-dihydro-2-naphthalenyl}methyl)-1,2,3,6-tetrahydropyridine,
1-(4-fluorophenyl)-4-({6-[(4-isobutyl-2-methoxybenzyl)oxy]-1-methyl-3,4-dihydro-2-naphthalenyl}methyl)piperazine,
4-({6-[(4-isobutyl-2-methoxybenzyl)oxy]-1-methyl-3,4-dihydro-2-naphthalenyl}methyl)-2,6-dimethylmorpholine,
8-({6-[(4-isobutyl-2-methoxybenzyl)oxy]-1-methyl-3,4-dihydro-2-naphthalenyl}methyl)-1,4-dioxa-8-azaspiro[4.5]decane,
N,N-diethyl-1-({6-[(4-isobutyl-2-methoxybenzyl)oxy]-1-methyl-3,4-dihydro-2-naphthalenyl}methyl-3-piperidinecarboxamide,
1'-({6-[(4-isobutyl-2-methoxybenzyl)oxy]-1-methyl-3,4-dihydro-2-naphthalenyl}methyl)-1,4'-bipiperidine,
1-({6-[(4-isobutyl-2-methoxybenzyl)oxy]-1-methyl-3,4-dihydro-2-naphthalenyl}methyl)-2-methylpyrrolidine,
1-({6-[(4-isobutyl-2-methoxybenzyl)oxy]-1-methyl-3,4-dihydro-2-naphthalenyl}methyl)-4-(1-pyrrolidinyl)piperidine,
1-(2-fluorophenyl)-4-({6-[(4-isobutyl-2-methoxybenzyl)oxy]-1-methyl-3,4-dihydro-2-naphthalenyl}methyl)piperazine,
1-({6-[(4-isobutyl-2-methoxybenzyl)oxy]-1-methyl-3,4-dihydro-2-naphthalenyl}methyl)-4-(3-methoxyphenyl)piperazine,
2-{2-[4-({6-[(4-isobutyl-2-methoxybenzyl)oxy]-1-methyl-3,4-dihydro-2-naphthalenyl}methyl)-1-piperazinyl]ethoxy}ethanol,
t-butyl 4-({6-[(4-isobutyl-2-methoxybenzyl)oxy]-1-methyl-3,4-dihydro-2-naphthalenyl}methyl)-1-piperazinecarboxylate,
(3R)-1-({6-[(4-isobutyl-2-methoxybenzyl)oxy]-1-methyl-3,4-dihydro-2-naphthalenyl}methyl)-3-pyrrolidinol,
1-allyl-4-({6-[(4-isobutyl-2-methoxybenzyl)oxy]-1-methyl-3,4-dihydro-2-naphthalenyl}methyl)piperazine,
1-(cyclohexylmethyl)-4-({6-[(4-isobutyl-2-methoxybenzyl)oxy]-1-methyl-3,4-dihydro-2-naphthalenyl}methyl)piperazine,
1-(2-ethoxyethyl)-4-({6-[(4-isobutyl-2-methoxybenzyl)oxy]-1-methyl-3,4-dihydro-2-naphthalenyl}methyl)piperazine,
t-butyl(1S ,4S)-5-({6-[(4-isobutyl-2-methoxybenzyl)oxy]-1-methyl-3,4-dihydro-2-naphthalenyl}methyl)-2,5-diazabicyclo [2.2.1]heptane-2-carboxylate,
N-{[(2R)-1-({6-[(4-isobutyl-2-methoxybenzyl)oxy]-1-methyl-3,4-dihydro-2-naphthalenyl}methyl)-2-pyrrolidinyl]methyl}aniline,
1-(3,4-dimethylphenyl)-4-({6-[(4-isobutyl-2-methoxybenzyl)oxy]-1-methyl-3,4-dihydro-2-naphthalenyl}methyl)piperazine,
1-(2,5-dimethylphenyl)-4-({6-[(4-isobutyl-2-methoxybenzyl)oxy]-1-methyl-3,4-dihydro-2-naphthalenyl}methyl)piperazine,
1-(2-furoyl)-4-({6-[(4-isobutyl-2-methoxybenzyl)oxy]-1-methyl-3,4-dihydro-2-naphthalenyl}methyl)piperazine,
1-({6-[(4-isobutyl-2-methoxybenzyl)oxy]-1-methyl-3,4-dihydro-2-naphthalenyl}methyl)-4-(2-phenylethyl)piperazine,
1-({6-[(4-isobutyl-2-methoxybenzyl)oxy]-1-methyl-3,4-dihydro-2-naphthalenyl}methyl)-4-(4-pyridinyl)piperazine, 2-[4-({6-[(4-isobutyl-2-methoxybenzyl)oxy]-1-methyl-3,4-dihydro-2-naphthalenyl}methyl)-1-piperazinyl]benzonitrile,
3-[4-({6-[(4-isobutyl-2-methoxybenzyl)oxy]-1-methyl-3,4-dihydro-2-naphthalenyl}methyl)-1-piperazinyl]phenol,
1-(2,4-difluorophenyl)-4-({6-[(4-isobutyl-2-methoxybenzyl)oxy]-1-methyl-3,4-dihydro-2-naphthalenyl}methyl)piperazine,
1-({6-[(4-isobutyl-2-methoxybenzyl)oxy]-1-methyl-3,4-dihydro-2-naphthalenyl}methyl)-4-(trifluoromethyl)piperidine,
2-[4-({6-[(4-isobutyl-2-methoxybenzyl)oxy]-1-methyl-3,4-dihydro-2-naphthalenyl}methyl)-1-piperazinyl]phenol,
1-({6-[(4-isobutyl-2-methoxybenzyl)oxy]-1-methyl-3,4-dihydro-2-naphthalenyl}methyl)-4-(tetrahydro-2-furanylcarbonyl)piperazine,
1-benzyl-4-({6-[(4-isobutyl-2-methoxybenzyl)oxy]-1-methyl-3,4-dihydro-2-naphthalenyl}methyl)-1,4-diazepane,
4-({6-[(4-isobutyl-2-methoxybenzyl)oxy]-1-methyl-3,4-dihydro-2-naphthalenyl}methyl)-1,4-diazepane-1-carbaldehyde,
2-[4-({6-[(4-isobutyl-2-methoxybenzyl)oxy]-1-methyl-3,4-dihydro-2-naphthalenyl}methyl)-1-piperazinyl]-N-isopropylacetamide,
1-({6-[(4-isobutyl-2-methoxybenzyl)oxy]-1-methyl-3,4-dihydro-2-naphthalenyl}methyl)-4-phenylpiperidine,
1-(2,3-dimethylphenyl)-4-({6-[(4-isobutyl-2-methoxybenzyl)oxy]-1-methyl-3,4-dihydro-2-naphthalenyl}methyl)piperazine,
1-({6-[(4-isobutyl-2-methoxybenzyl)oxy]-1-methyl-3,4-dihydro-2-naphthalenyl}methyl)-4-(4-methoxyphenyl)piperazine,
1-cyclohexyl-4-({6-[(4-isobutyl-2-methoxybenzyl)oxy]-1-methyl-3,4-dihydro-2-naphthalenyl}methyl)piperazine,
1-(4-chlorophenyl)-4-({6-[(4-isobutyl-2-methoxybenzyl)oxy]-1-methyl-3,4-dihydro-2-naphthalenyl}methyl)piperazine,
1-({6-[(4-isobutyl-2-methoxybenzyl)oxy]-1-methyl-3,4-dihydro-2-naphthalenyl}methyl)-4-(2-methoxyethyl)piperazine,
4-{2-[4-({6-[(4-isobutyl-2-methoxybenzyl)oxy]-1-methyl-3,4-dihydro-2-naphthalenyl}methyl)-1-piperazinyl]ethyl}morpholine,
(2S,5S)-1-({6-[(4-isobutyl-2-methoxybenzyl)oxy]-1-methyl-3,4-dihydro-2-naphthalenyl}methyl)-2,5-bis(methoxymethyl)pyrrolidine,
4-({6-[(4-isobutyl-2-methoxybenzyl)oxy]-1-methyl-3,4-dihydro-2-naphthalenyl}methyl)-2-piperazinone,
(2S)-1-({6-[(4-isobutyl-2-methoxybenzyl)oxy]-1-methyl-3,4-dihydro-2-naphthalenyl}methyl)-N,N-dimethyl-2-pyrrolidinecarboxamide,
(2R)-1-({6-[(4-isobutyl-2-methoxybenzyl)oxy]-1-methyl-3,4-dihydro-2-naphthalenyl}methyl)-2-pyrrolidinecarboxamide,
1-({6-[(4-isobutyl-2-methoxybenzyl)oxy]-1-methyl-3,4-dihydro-2-naphthalenyl}methyl)-4-(2-methylphenyl)piperazine,
2-[4-({6-[(4-isobutyl-2-methoxybenzyl)oxy]-1-methyl-3,4-dihydro-2-naphthalenyl}methyl)-1-piperazinyl]nicotinonitrile,
3-[4-({6-[(4-isobutyl-2-methoxybenzyl)oxy]-1-methyl-3,4-dihydro-2-naphthalenyl}methyl)-1-piperazinyl]-2-pyrazinecarbonitrile,
6-[4-({6-[(4-isobutyl-2-methoxybenzyl)oxy]-1-methyl-3,4-dihydro-2-naphthalenyl}methyl)-1-piperazinyl]nicotinonitrile,
1-[(6-{[(2R)-3-(4-fluorophenyl)-2-methylpropyl]oxy}-1-methyl-3,4-dihydro-2-naphthalenyl)methyl]azocane,
1-[(6-{[(2R)-3-(4-fluorophenyl)-2-methylpropyl]oxy}-1-methyl-3,4-dihydro-2-naphthalenyl)methyl]pyrrolidine,
1-[(6-{[(2R)-3-(4-fluorophenyl)-2-methylpropyl]oxy}-1-methyl-3,4-dihydro-2-naphthalenyl)methyl]-3-pyrrolidinol,
1-[(6-{[(2R)-3-(4-fluorophenyl)-2-methylpropyl]oxy}-1-methyl-3,4-dihydro-2-naphthalenyl)methyl]-4-phenylpiperazine,
4-[(6-{[(2R)-3-(4-fluorophenyl)-2-methylpropyl]oxy}-1-methyl-3,4-dihydro-2-naphthalenyl)methyl]-1-piperazinecarbaldehyde,
1-[(6-{[(2R)-3-(4-fluorophenyl)-2-methylpropyl]oxy}-1-methyl-3,4-dihydro-2-naphthalenyl)methyl]-4-methylpiperazine,
1-benzyl-4-[(6-{[(2R)-3-(4-fluorophenyl)-2-methylpropyl]oxy}-1-methyl-3,4-dihydro-2-naphthalenyl)methyl]piperazine,
4-[(6-{[(2R)-3-(4-fluorophenyl)-2-methylpropyl]oxy}-1-methyl-3,4-dihydro-2-naphthalenyl)methyl]morpholine,
1-[(6-{[(2R)-3-(4-fluorophenyl)-2-methylpropyl]oxy}-1-methyl-3,4-dihydro-2-naphthalenyl)methyl]piperidine,
1-[(6-{[(2R)-3-(4-fluorophenyl)-2-methylpropyl]oxy}-1-methyl-3,4-dihydro-2-naphthalenyl)methyl]-4-(2-piperidinyl)piperazine,
4-[(6-{[(2R)-3-(4-fluorophenyl)-2-methylpropyl]oxy}-1-methyl-3,4-dihydro-2-naphthalenyl)methyl]-2-piperazinone,
N-[(6-{[(2R)-3-(4-fluorophenyl)-2-methylpropyl]oxy}-1-methyl-3,4-dihydro-2-naphthalenyl)methyl]-N-methyl-1-pentanamine, or
N-[(6-{[(2R)-3-(4-fluorophenyl)-2-methylpropyl]oxy}-1-methyl-3,4-dihydro-2-naphthalenyl)methyl]-N,N',N'-trimethyl-1,3-propanediamine.

2. A pharmaceutical composition which comprises the compound according to claim 1, a salt thereof or an N-oxide form thereof, and a pharmaceutically acceptable carrier or diluent.

3. A medicament comprising the compound according to claim 1, a salt thereof or an N-oxide form thereof, in combination with one or at least two selected from the group consisting of an antimetabolite, an alkylating agent, a T cell activation inhibitor, a calcineurin inhibitor, a proliferation signal inhibitor, a steroid, an immunosuppressant agent, an antibody used in immune suppression, an agent for treating rejection, an antibiotic, an antiviral agent, and an antifungal agent.

4. A method for treatment of rejection in transplantation of an organ, tissues, and/or cells; autoimmune disease, allergic disease, or asthma, which comprises administering to the mammal an effective amount of the compound according to claim 1, a salt thereof or an N-oxide form thereof.

5. A method for causing immunosuppression in a mammal, which comprises administering to the mammal an effective amount of the compound according to claim 1, a salt thereof or an N-oxide form thereof.

6. A method for causing lymphopenia in a mammal, which comprises administering to the mammal an effective amount of the compound according to claim 1, a salt thereof or an N-oxide form thereof.

* * * * *